United States Patent
Bowles et al.

(10) Patent No.: US 12,410,428 B2
(45) Date of Patent: Sep. 9, 2025

(54) RNA-GUIDED TRANSCRIPTIONAL REGULATION AND METHODS OF USING THE SAME FOR THE TREATMENT OF BACK PAIN

(71) Applicant: University of Utah Research Foundation, Salt Lake City, UT (US)

(72) Inventors: Robert Daniel Bowles, Salt Lake City, UT (US); Niloofar Farhang, Salt Lake City, UT (US); David Ede, Salt Lake City, UT (US); Jacob Weston, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1085 days.

(21) Appl. No.: 17/284,908

(22) PCT Filed: Oct. 18, 2019

(86) PCT No.: PCT/US2019/056913
§ 371 (c)(1),
(2) Date: Apr. 13, 2021

(87) PCT Pub. No.: WO2020/081922
PCT Pub. Date: Apr. 23, 2020

(65) Prior Publication Data
US 2021/0380975 A1    Dec. 9, 2021

Related U.S. Application Data

(60) Provisional application No. 62/747,421, filed on Oct. 18, 2018.

(51) Int. Cl.
*C12N 15/11* (2006.01)
*A61K 31/7088* (2006.01)
(Continued)

(52) U.S. Cl.
CPC .......... *C12N 15/11* (2013.01); *A61K 31/7088* (2013.01); *A61K 38/465* (2013.01);
(Continued)

(58) Field of Classification Search
CPC .......... C12N 15/11; C12N 9/22; C12N 15/86; C12N 15/907; C12N 2310/20;
(Continued)

(56) References Cited

U.S. PATENT DOCUMENTS

| | | |
|---|---|---|
| 2013/0297023 A1 | 11/2013 | Sampen et al. |
| 2014/0364336 A1 | 12/2014 | Aldred et al. |

(Continued)

FOREIGN PATENT DOCUMENTS

| | | |
|---|---|---|
| EP | 16812546.6 | 6/2016 |
| EP | 20176267.1 | 5/2020 |

(Continued)

OTHER PUBLICATIONS

U.S. Appl. No. 62/230,931, filed Jun. 18, 2015, Robert D. Bowles.
(Continued)

*Primary Examiner* — Marcia S Noble
*Assistant Examiner* — Briana N Ebbinghaus
(74) *Attorney, Agent, or Firm* — BALLARD SPAHR LLP

(57) ABSTRACT

Disclosed herein are compositions and methods for treatment and prevention of low back pain. The compositions include vectors comprising nucleotide sequences encoding one or more CRISPR-Cas system guide RNAs and a RNA-directed nuclease. The methods include modulating expression of one or more genes in a cell using the compositions, introducing a CRISPR-Cas system into a cell comprising one or more vectors comprising the compositions, including site-specific DNA cleavage in a cell, and treating a subject
(Continued)

having lower back pain, and lower back pain caused by degenerative disc disease using the compositions disclosed herein.

10 Claims, 41 Drawing Sheets

Specification includes a Sequence Listing.

(51) Int. Cl.
| | |
|---|---|
| A61K 38/46 | (2006.01) |
| A61P 29/00 | (2006.01) |
| C12N 9/22 | (2006.01) |
| C12N 15/86 | (2006.01) |
| C12N 15/90 | (2006.01) |

(52) U.S. Cl.
CPC ............... *A61P 29/00* (2018.01); *C12N 9/22* (2013.01); *C12N 15/86* (2013.01); *C12N 15/907* (2013.01); *C12N 2310/20* (2017.05); *C12N 2740/15043* (2013.01); *C12N 2800/80* (2013.01)

(58) Field of Classification Search
CPC ...... C12N 2740/15043; C12N 2800/80; C12N 2740/16043; C12N 15/63; C12N 2800/40; A61K 31/7088; A61K 38/465; A61P 29/00
See application file for complete search history.

(56) References Cited

U.S. PATENT DOCUMENTS

| | | | | |
|---|---|---|---|---|
| 2017/0204407 A1* | 7/2017 | Gilbert | ............... | C12N 15/1082 |
| 2018/0073019 A1* | 3/2018 | Khalili | .................. | A61K 45/06 |
| 2018/0154462 A1 | 6/2018 | Yamamichi | | |
| 2018/0155715 A1 | 6/2018 | Bowles et al. | | |

FOREIGN PATENT DOCUMENTS

| | | | | |
|---|---|---|---|---|
| WO | WO 2002/088393 A1 | 11/2002 | | |
| WO | WO 2014/191128 A1 | 12/2014 | | |
| WO | WO 2014/197748 A2 | 12/2014 | | |
| WO | WO-2016011080 A2 * | 1/2016 | ........... | C12N 15/102 |
| WO | PCT/US2016/038137 | 6/2016 | | |
| WO | PCT/US2019/056913 | 10/2019 | | |

OTHER PUBLICATIONS

U.S. Appl. No. 62/747,421, filed Oct. 18, 2018, Robert D. Bowles.
U.S. Appl. No. 15/737,516 (U.S. Pat. No. 10,954,513), filed Dec. 18, 2017 (Mar. 23, 2021), Robert D. Bowles (Univ. of Utah Res. Found.).
Adams, M. A. & Roughley, P. J., "What is intervertebral disc degeneration, and what causes it?" Spine (Phila. Pa. 1976), 31: 2151-61 (2006).
Andrade, P. et al., "Tumor Necrosis Factor-α Levels Correlate with Postoperative Pain Severity in Lumbar Disc Hernia Patients: Opposite Clinical Effects Between Tumor Necrosis Factor Receptor 1 and 2," Pain, 152(11): 2645-52 (2011).
Andratsch, M. et al., "A key role for gp130 expressed on peripheral sensory nerves in pathological pain," J Neurosci., 29(43): 13473-83 (2009).
Aoki, Y. et al., "Expression and co-expression of VR1, CGRP, and IB4-binding glycoprotein in dorsal root ganglion neurons in rats: differences between the disc afferents and the cutaneous afferents," Spine (Phila. Pa. 1976), 30(13):1496-500 (2005).
Aoki, Y. et al., "Innervation of the lumbar intervertebral disc by nerve growth factor-dependent neurons related to inflammatory pain," Spine (Phila Pa 1976), 29(10): 1077-81 (2004).

Ashton, I.K. et al., "Neuropeptides in the human intervertebral disc," J Orthop Res., 12(2):186-92 (1994).
Barde, I. et al., "Production and titration of lentiviral vectors," Curr. Protoc. Neurosci., 53: 4.21.1-4.21.23 (2010).
Bowles, R.D. et al., "In vivo luminescent imaging of NF-κB activity and NF-κB related serum cytokine levels predict pain sensitivities in a rodent model of peripheral neuropathy," Eur. J. Pain, 20(3): 365-76 (21 pages), (2015).
Brandao, K.E. et al., "A-kinase anchoring protein 150 expression in a specific subset of TRPV1- and CaV 1.2-positive nociceptive rat dorsal root ganglion neurons,". J Comp Neurol., 520(1): 81-99 (27 pages) (2012).
Brown, N.I.F. et al., "Sensory and sympathetic innervation of the vertebral endplate in patients with degenerative disc disease," J Bone Joint Surg Br., 79(1): 147-53 (1997).
Btesh, J. et al., "Mapping the binding site of TRPV1 on AKAP79: implications for inflammatory hyperalgesia," J Neurosci., 33(21): 9184-93 (26 pages), (2013).
Burke, J.G. et al., "Human nucleus pulposis can respond to a pro-inflammatory stimulus," Spine (Phila Pa 1976), 28(24): 2685-93 (2003).
Burke, J.G. et al., "Intervertebral discs which cause low back pain secrete high levels of proinflammatory mediators," J Bone Joint Surg Br., 84(2): 196-201 (2002).
Cabal-Hierro, L. and Lazo, P.S., "Signal transduction by tumor necrosis factor receptors," Cell Signal., 24(6): 1297-305 (2012).
Caterina, M.J. et al., "The capsaicin receptor: a heat-activated ion channel in the pain pathway," Nature, 389(6653): 816-24 (1997).
Chavez, A. et al., "Highly efficient Cas9-mediated transcriptional programming," Nat. Methods, 12(4): 326-328 (2015).
Chen, E. Y. et al., "Enrichr: interactive and collaborative HTML5 gene list enrichment analysis tool," BMC Bioinformatics, 14: 128 (2013).
Chun, H.-J. et al., "Transplantation of human adipose-derived stem cells in a rabbit model of traumatic degeneration of lumbar discs," World Neurosurg., 78(3-4): 364-71 (2012).
Cissell, D. D., et al. "A modified hydroxyproline assay based on hydrochloric acid in Ehrlich's solution accurately measures tissue collagen content," Tissue Eng. Part C., Methods 23: 243-250 (2017).
Cong, L. et al., "Multiplex genome engineering using CRISPR/Cas systems," Science, 339(6121): 819-23 (9 pages), (2013).
Coppes, M.H. et al., "Innervation of annulus fibrosis in low back pain," Lancet (London, England), 336(8708): 189-90 (1990).
Cribbs, A. P., et al., "Simplified production and concentration of lentiviral vectors to achieve high transduction in primary human T cells," BMC Biotechnol., 13: 98 (2013).
Cronin, et al., "Altering the tropism of lentiviral vectors through pseudotyping," J. Curr. Gene Ther., 5(4): 387-98 (2005).
De Bari, C., et al. "Stem cell-based therapeutic strategies for cartilage defects and osteoarthritis," Current Opinion in Pharmacology, 40: 74-80 (2018).
Diekman, B. O. & Guilak, F., "Stem cell-based therapies for osteoarthritis: challenges and opportunities," Curr. Opin. Rheumatol., 25(1): 119-126 (2013).
Engler, A. J., et al., "Matrix elasticity directs stem cell lineage specification," Cell, 126(4): 677-689 (2006).
Fang, D. et al., "Interleukin-6-mediated functional upregulation of TRPV1 receptors in dorsal root ganglion neurons through the activation of JAK/PI3K signaling pathway: roles in the development of bone cancer pain in a rat model," Pain, 156(6):1124-44 (2015).
Farhang, N. et al., CRISPRi Immunomodulation for Tissue Engineering/ Stem Cell Therapies Targeting Intervertebral Disc Degeneration. Tissue Eng Part A. 2015; 21(Suppl 1):s170.
Farhang, N. et al., "CRISPR-based epigenome editing of cytokine receptors for the promotion of cell survival and tissue deposition in inflammatory environments," Tissue Eng. Part A, 23(15-16): 738-749 (2017).
Freemont, A.J. et al., "Nerve growth factor expression and innervation of the painful intervertebral disc," J Pathol., 197(3): 286-92 (2002).

(56) References Cited

OTHER PUBLICATIONS

Freemont, A.J. et al., "Nerve ingrowth into diseased intervertebral disc in chronic back pain," Lancet (London, England), 350(9072): 178-81 (1997).
Frisch, J., et al., "Current progress in stem cell-based gene therapy for articular cartilage repair," Curr. Stem Cell Res. Ther., 10: 121-31 (2015).
García-Cosamalón, J. et al., "Intervertebral disc, sensory nerves and neurotrophins: who is who in discogenic pain?" J Anat., 217(1): 1-15 (2010).
Gene Ontology Consortium, "The Gene Ontology project in 2008," Nucleic Acids Res., 36: D440-4 (2008).
Gersbach, C. A. & Perez-Pinera, P, "Activating human genes with zinc finger proteins, transcription activator-like effectors and CRISPR/Cas9 for gene therapy and regenerative medicine," Expert Opin. Ther. Targets, 18(8): 835-9 (2014).
Gilbert LA, et al., "Genome-Scale CRISPR-Mediated Control of Gene Repression and Activation, Cell," 159: 647-661 (2014).
Gilbert, L.A. et al., "Genome-Scale CRISPR-Mediated Control of Gene Repression and Activation," Cell, 159(3): 647-61 (2014), (26 pages).
Greffrath, W. et al., "Changes in cytosolic calcium in response to noxious heat and their relationship to vanilloid receptors in rat dorsal root ganglion neurons," Neuroscience, 104(2): 539-50 (2001).
Groner, A.C. et al., "KRAB-zinc finger proteins and KAP1 can mediate long-range transcriptional repression through heterochromatin spreading," PLoS Genet., 6:e1000869 (2010), (14 pages).
Heldens, G.T.H. et al., "Catabolic factors and osteoarthritis-conditioned medium inhibit chondrogenesis of human mesenchymal stem cells," Tissue Eng Part A., 18(1-2): 45-54 (2012).
Hino, K. et al., "Master regulator for chondrogenesis, Sox9, regulates transcriptional activation of the endoplasmic reticulum stress transducer BBF2H7/CREB3L2 in chondrocytes," J. Biol. Chem., 289 (20): 13810-13820 (2014).
Hoy, D. et al., "A systematic review of the global prevalence of low back pain," Arthritis Rheum., 64(6): 2028-37 (2012).
Hsu, P.D. et al., "DNA targeting specificity of RNA-guided Cas9 nucleases," Nat Biotechnol., 31(9):827-32 (2013), (17 pages).
Illien-Junger, S. et al., "Development of a bovine decellularized extracellular matrix-biomaterial for nucleus pulposus regeneration," J. Orthop. Res.. 34: 876-88 (2016).
Jara-Oseguera, A. et al., "TRPV1: On the Road to Pain Relief," Curr Mol Pharmacol., 1(3): 255-69 (2008), (34 pages).
Jeske, N.A. et al., "A-kinase anchoring protein mediates TRPV1 thermal hyperalgesia through PKA phosphorylation of TRPV1," Pain, 138(3): 604-16 (2008), (20 pages).
Jeske, N.A. et al., "A-kinase anchoring protein 150 controls protein kinase C-mediated phosphorylation and sensitization of TRPV1," Pain, 146(3): 301-7 (2009), (15 pages).
Jevotovsky, D. S., et al., "Osteoarthritis and stem cell therapy in humans: a systematic review," Osteoarthr. Cartil.. 26: 711-729 (2018).
Jinek, M. et al., "A programmable dual-RNA-guided DNA endonuclease in adaptive bacterial immunity," Science, 337(6096): 816-21 (2012).
Johnson, W.E. et al., "Immunohistochemical detection of Schwann cells in innervated and vascularized human intervertebral discs," Spine (Phila Pa 1976), 26(23): 2550-7 (2001).
Katz, J.N., "Lumbar disc disorders and low-back pain: socioeconomic factors and consequences," J Bone Joint Surg Am., 88(2): 21-4 (2006).
Kent, W.J. et al., "The human genome browser at UCSC," Genome Res., 12(6): 996-1006 (2002).
Kepler, C.K. et al., "The molecular basis of intervertebral disc degeneration," Spine J., 13(3): 318-30 (2013).
Kestell, G.R. et al., "Primary afferent neurons containing calcitonin gene related peptide but not substance P in forepaw skin, dorsal root ganglia, and spinal cord of mice," J Comp Neurol., 523(17): 2555-69 (2015).
Kim, D., et al., "HISAT: a fast spliced aligner with low memory requirements," Nat. Methods, 12(4): 357-60 (2015).

Kitano, T. et al., "Biochemical changes associated with the symptomatic human intervertebral disk," Clin Orthop Relat Res., (293): 372-7 (1993).
Kokubo, Y. et al., "Herniated and spondylotic intervertebral discs of the human cervical spine: histological and immunohistological findings in 500 en bloc surgical samples," Laboratory Investigation, J Neurosurg Spine, 9(3): 285-95 (2008).
Krebs, C.J. et al., "The KRAB zinc finger protein RSL1 regulates sex- and tissue-specific promoter methylation and dynamic hormone-responsive chromatin configuration," Mol Cell Biol., 32(18): 3732-42 (2012).
Kreiss, P. et al., "Plasmid DNA size does not affect the physicochemical properties of lipoplexes but modulates gene transfer efficiency," Nucleic Acids Res., 27(19): 3792-3798 (1999).
Krock, E. et al., "Painful, degenerating intervertebral discs up-regulate neurite sprouting and CGRP through nociceptive factors," J Cell Mol Med., 18(6): 1213-25 (2014).
Krock, E., et al., "The inflammatory milieu of the degenerate disc: is mesenchymal stem cell-based therapy for intervertebral disc repair a feasible approach?" Curr. Stem Cell Res. Ther., 10(4): 317-328 (2015).
Kuleshov, M. V. et al., "Enrichr: a comprehensive gene set enrichment analysis web server 2016 update," Nucleic Acids Res., 44(W1): W90-W97 (2016).
Larson, M.H. et al., "CRISPR interference (CRISPRi) for sequence-specific control of gene expression," Nat Protoc., 8(11): 2180-96 (2013).
Lee, B. L.P. et al., "Synovial stem cells and their responses to the porosity of microfibrous scaffold," Acta Biomater., 9(7): 7264-75 (2013).
Le Maitre, C.L. et al., "Catabolic cytokine expression in degenerate and herniated human intervertebral discs: IL-1β and TNFα expression profile," Arthritis Res Ther., 9(4):R77 (2007), (11 pages).
Le Maitre, C.L et al., "Matrix synthesis and degradation in human intervertebral disc degeneration," Biochem Soc Trans., 35(Pt 4): 652-5 (2007).
Le Maitre, C.L. et al., "Expression of receptors for putative anabolic growth factors in human intervertebral disc: implications for repair and regeneration of the disc," J Pathol., 207(4): 445-52 (2005).
Li, H. et al., "The sequence alignment/map format and SAMtools," Bioinformatics 25(16): 2078-9 (2009).
Liang, C. et al., "Responses of human adipose-derived mesenchymal stem cells to chemical microenvironment of the intervertebral disc," J Transl Med., 10:49 (2012), (10 pages).
Liao, Y., et al., "featureCounts: an efficient general purpose program for assigning sequence reads to genomic features," Bioinformatics 30: 923-30 (2014).
Lin, X. et al., "Decellularized allogeneic intervertebral disc: natural biomaterials for regenerating disc degeneration," Oncotarget 7, 12121-36 (2016).
Liu, Z., et al., "Looking into the Future: Toward Advanced 3D Biomaterials for Stem-Cell-Based Regenerative Medicine," Adv. Mater., 30(17): e1705388 (2018).
Lotz, J.C. and Ulrich, J.A., "Innervation, inflammation, and hypermobility may characterize pathologic disc degeneration: Review of animal model data," J Bone Joint Surg Am., 88(2): 76-82 (2006).
Love, M. I., et al., "Moderated estimation of fold change and dispersion for RNA-seq data with DESeq2," Genome Biol., 15(12): 550 (2014).
Luoma, K et al., "Low back pain in relation to lumbar disc degeneration," Spine (Phila Pa 1976), 25(4): 487-92 (2000), (7 pages).
Maldonado, M. & Nam, J., "The role of changes in extracellular matrix of cartilage in the presence of inflammation on the pathology of osteoarthritis," BioMed Research International 2013: 284873 (2013).
Mali, P. et al., "Cas9 as a versatile tool for engineering biology," Nat Methods, 10(10): 957-63 (2013), (16 pages).
Marfia, G. et al., "Potential use of human adipose mesenchymal stromal cells for intervertebral disc regeneration: a preliminary study on biglycan deficient murine model of chronic disc degeneration," Arthritis Res Ther., 16(5): 457 (2014), (13 pages).

(56) References Cited

OTHER PUBLICATIONS

Maroudas, A. et al., "Factors involved in the nutrition of the human lumbar intervertebral disc: cellularity and diffusion of glucose in vitro," J. Anat, 120: 113-130 (1975).

Matsiko, A., et al., "Scaffold mean pore size influences mesenchymal stem cell chondrogenic differentiation and matrix deposition," Tissue Eng. Part A. 21(3-4): 486-97 (2015).

Matsuzaki, S. et al., "Physiological ER stress mediates the differentiation of fibroblasts," PLoS One, 10(4), e0123578 (2015).

Melrose, J. et al., "Increased nerve and blood vessel ingrowth associated with proteoglycan depletion in an ovine annular lesion model of experimental disc degeneration," Spine (Phila Pa 1976), 27(12): 1278-85 (2002).

Milone, M. C. & O'Doherty, U., "Clinical use of lentiviral vectors," Leukemia 32(7): 1529-1541 (2018).

Millward-Sadler, S.J. et al., "Regulation of catabolic gene expression in normal and degenerate human intervertebral disc cells: implications for the pathogenesis of intervertebral disc degeneration," Arthritis Res Ther., 11(3): R65 (2009), (10 pages).

Murray, C.J., et al., "Disability-adjusted life years (DALYs) for 291 diseases and injuries in 21 regions, 1990-2010: a systematic analysis for the Global Burden of Disease Study 2010," Lancet., 380(9859): 2197-223 (2012).

Murray, C.J.L. and Lopez, A.D., "Measuring the global burden of disease," N Engl J Med., 369: 448-57 (2013).

Mwale, F., et al., "Eur. Distinction between the extracellular matrix of the nucleus pulposus and hyaline cartilage: a requisite for tissue engineering of intervertebral disc," Cells and Mater., 8: 58-64 (2004).

O'Brien, A. & Bailey, T. L. GT-scan: identifying unique genomic targets. Bioinformatics 30(18): 2673-5 (2014).

Obreja, O. et al., "Fast modulation of heat-activated ionic current by proinflammatory interleukin 6 in rat sensory neurons,". Brain, 128(7): 1634-41 (2005).

Obreja, O. et al., "Interleukin-6 in combination with its soluble IL-6 receptor sensitizes rat skin nociceptors to heat, in vivo," Pain, 96(1-2): 57-62 (2002).

Ohtori, S. et al., "Substance P and calcitonin gene-related peptide immunoreactive sensory DRG neurons innervating the lumbar intervertebral discs in rats," Ann Anat., 184(3): 235-40 (2002).

Oka, Y. et al., "Interleukin-6 is a candidate molecule that transmits inflammatory information to the CNS," Neuroscience, 145(2): 530-8 (2007).

Opree, A. and Kress, M., "Involvement of the proinflammatory cytokines tumor necrosis factor-$\alpha$, IL-1$\beta$, and IL-6 but not IL-8 in the development of heat hyperalgesia: effects on heat-evoked calcitonin gene-related peptide release from rat skin," J Neurosci., 20(16): 6289-93 (2000).

Orozco, L. et al., "Intervertebral disc repair by autologous mesenchymal bone marrow cells: a pilot study," Transplantation, 92(7): 822-8 (2011).

Pettine, K. et al., "Treatment of discogenic back pain with autologous bone marrow concentrate injection with minimum two year follow-up," Int Orthop., 40(1): 135-40 (2016).

Puetzer, J. L., et al., "Comparative review of growth factors for induction of three-dimensional in vitro chondrogenesis in human mesenchymal stem cells isolated from bone marrow and adipose tissue," Tissue Eng. Part B. Rev., 16: 435-44 (2010).

Purmessur, D. et al., A role for TNF$\alpha$ in intervertebral disc degeneration: a non-recoverable catabolic shift. Biochem Biophys Res Commun. 2013; 433(1):151-6 (13 pages).

Ramamoorth, M. & Narvekar, "A. Non viral vectors in gene therapy—an overview," J. Clin. Diagn. Res., 9(1): GE01-6 (2015).

Reynolds, N. et al., NuRD-mediated deacetylation of H3K27 facilitates recruitment of Polycomb Repressive Complex 2 to direct gene repression. EMBO J. 2012; 31(3):593-605.

Risbud, M.V. and Shapiro, I.M., Role of cytokines in intervertebral disc degeneration: pain and disc content, Nat rev Rheumatol., 10(1): 44-56 (2014).

Risbud, M. V et al., "Defining the phenotype of young healthy nucleus pulposus cells: recommendations of the Spine Research Interest Group at the 2014 annual ORS meeting," J Orthop Res, 33: 283-293 (2015).

Roberts, S. et al., "Histology and pathology of the human intervertebral disc," J Bone Joint Surg Am., 88(2): 10-14 (2006).

Rosemann, T. et al., "Problems and needs for improving primary care of osteoarthritis patients: the views of patients, general practitioners and practice nurses," BMC Musculoskelet Disord., Jun. 2; 7: 48 (2006).

Saito, A. et al., "Regulation of endoplasmic reticulum stress response by a BBF2H7-mediated Sec23a pathway is essential for chondrogenesis,", Nat. Cell Biol., 11(10): 1197-1204 (2009).

Sandell, L. J. & Aigner, T., "Articular cartilage and changes in arthritis. An introduction: cell biology of osteoarthritis," Arthritis Res., 3(2): 107 (2001).

Sasi, S.P. et al., "Genetic Deletion of TNFR2 Augments Inflammatory Response and Blunts Satellite-Cell-Mediated Recovery Response in a Hind Limb Ischemia Model," FASEB J., 29(4): 1208-19 (2014).

Schindelin, J. et al., "Fiji—an open source platform for biological image analysis," Nat Methods, 9(7):676-82 (2012), (15 pages).

Schol, J. & Sakai, D., "Cell therapy for intervertebral disc herniation and degenerative disc disease: clinical trials," Int. Orthop., 43:1011-1025 (2019).

Sekiya, I., et al., "In vitro cartilage formation by human adult stem cells from bone marrow stroma defines the sequence of cellular and molecular events during chondrogenesis," J. Proc. Natl. Acad. Sci. U. S. A., 99(7): 4397-402 (2002).

Shamji, M.F. et al., "Proinflammatory cytokine expression profile in degenerated and herniated human intervertebral disc tissues," Arthritis Rheum., 62(7): 1974-82 (2010), (15 pages).

Shen, C. et al., "In vitro culture expansion impairs chondrogenic differentiation and the therapeutic effect of mesenchymal stem cells by regulating the unfolded protein response," J. Biol. Eng., 12: 26 (2018).

Shi, S. et al., "Comparative effectiveness of structural versus regulatory protein gene transfer on articular chondrocyte matrix gene expression," Cartilage, 10(1): 102-110 (2019).

Sorushanova, A. et al., "The collagen suprafamily: from biosynthesis to advanced biomaterial development," Adv. Mater., 31(1): e1801651 (2019).

Specchia, N. et al., "Cytokines and growth factors in the protruded intervertebral disc of the lumbar spine," Eur Spine J., 11(2):145-51 (2002).

Sripathy, S.P. et al., "The KAP1 corepressor functions to coordinate the assembly of de novo HP1-demarcated microenvironments of eterochromatin required for KRAB zinc finger protein-mediated ranscriptional repression," Mol Cell Biol., 26(22): 8623-38 (2006).

Stockwell, R. A., "The cell density of human articular and costal cartilage," J. Anat 101 (Pt 4): 753-63 (1967).

Strassburg, S. et al., "Co-culture induces mesenchymal stem cell differentiation and modulation of the degenerate human nucleus pulposus cell phenotype," Regen Med., 5(5): 701-11 (2010).

Studer, R.K. et al., "Human nucleus pulposus cells react to IL-6: independent actions and amplification of response to IL-1 and TNF-$\alpha$," Spine (Phila Pa 1976), 36(8): 593-9 (2011).

Suthar, P. et al., "MRI evaluation of lumbar disc degenerative disease," J Clin Diagn Res., 9(4): TC04-9 (2015).

Tam, V. et al., "A comparison of intravenous and intradiscal delivery of multipotential stem cells on the healing of injured intervertebral disk," J Orthop Res., 32(6): 819-25 (2014).

Tamaddon, M. et al., "Monomeric, porous type II collagen scaffolds promote chondrogenic differentiation of human bone marrow mesenchymal stem cells in vitro," Sci. Rep., 7: 43519 (2017).

Thakore, P.I. et al., "Editing the epigenome: technologies for programmable transcription and epigenetic modulation," Nat Methods., 13(2): 127-37 (2016), (27 pages).

Thakore, P.I. et al., "Highly specific epigenome editing by CRISPR-Cas9 repressors for silencing of distal regulatory elements," Nat Methods, 12(12): 1143-9 (2015), (22 pages).

Vadala, G., et al., "Interaction between mesenchymal stem cells and intervertebral disc microenvironment: from cell therapy to tissue engineering," Stem Cells Int., 2376172 (2019).

(56) References Cited

OTHER PUBLICATIONS

Vernon-Roberts, B. et al., "The natural history of age-related disc degeneration: the pathology and sequelae of tears," Spine (Phila Pa 1976), 32(25): 2797-804 (2007).
Vertel, B. M., "The ins and outs of aggrecan," Trends in Cell Biology, 5: 458-464 (1995).
Von Korff, M. and Saunders, K., "The course of back pain in primary care," Spine (Phila Pa 1976), 21: 2833-7; discussion 2838-9 (1996).
Vos, T. et al., "Global, regional, and national incidence, prevalence, and years lived with disability for 301 acute and chronic diseases and injuries in 188 countries, 1990-2013: a systematic analysis for the Global Burden of Disease Study 2013," Lancet., 386(9995): 743-800 (2015), (98 pages).
Vos, T. et al., "Global, regional, and national incidence, prevalence, and years lived with disability for 328 diseases and injuries for 195 countries, 1990-2016: a systemic analysis for the Global Burden of Disease Study 2016," Lancet., 390(10100): 1211-1259 (2017).
Wang, Y. et al., "Plasticity of mesenchymal stem cells in immunomodulation: pathological and therapeutic implications," Nat Immunol., 15: 1009-16 (2014).
Wang, F., et al., "Stem Cell Approaches to Intervertebral Disc Regeneration: Obstacles from the Disc Microenvironment," Stem Cells Dev., 24: 2479-2495 (2015).
Wehling, N. et al., "Interleukin-1β and tumor necrosis factor alpha inhibit chondrogenesis by human mesenchymal stem cells through NF-κB-dependent pathways," Arthritis Rheum., 60(3): 801-12 (2009), (12 pages).
Weiler, C. et al., "Expression and distribution of tumor necrosis factor alpha in human lumbar intervertebral discs: a study in surgical specimen and autopsy controls," Spine (Phila Pa 1976), 30(1): 44-53; discussion 54 (2005).
White, M., et al., "A guide to approaching regulatory considerations for lentiviral-mediated gene therapies," Human Gene Therapy Methods, 28(4): 163-176 (2017).
Wuertz, K. et al., "Behavior of mesenchymal stem cells in the chemical microenvironment of the intervertebral disc," Spine (Phila Pa 1976), 33(17): 1843-9 (2008).
Yazdany, J. & MacLean, C. H. Quality of care in the rheumatic diseases: current status and future directions. Curr. Opin. Rheumatol. 20(2): 159-166 (2008).
Zhang, Y. et al., "Tumor Necrosis Factor-α and Lymphotoxin-α Mediate Myocardial Ischemic Injury via TNF Receptor 1, but Are Cardioprotective When Activating TNF Receptor 2," PLoS One, 8(5): e60227 (2013), (6 pages).
Zheng, C.H. and Levenston, M.E., "Fact versus artifact: avoiding erroneous estimates of sulfated glycosaminoglycan content using the dimethylmethylene blue colorimetric assay for tissue-engineered constructs," Eur Cell Mater., 29:224-36; discussion 236 (2015), (23 pages).
International Search report and Written Opinion mailed on Dec. 1, 2016 by the International Searching Authority for Patent Application No. PCT/US2016/038137, which was filed on Jun. 17, 2016 and published as WO 2016/205688 on Dec. 22, 2016 (Inventor—Bowles et al.; Applicant—Robert D. Bowles) (12 pages).
International Preliminary Report on Patentability issued on Dec. 19, 2017 by the International Searching Authority for Patent Application No. PCT/US2016/038137, which was filed on Jun. 17, 2016 and published as WO 2016/205688 on Dec. 22, 2016 (Inventor—Bowles et al.; Applicant—Robert D. Bowles) (8 pages).
Supplementary European Search Report issued on Jan. 18, 2019 by the European Patent Office for Patent Application No. 16812546.6, which was filed on Jun. 17, 2016 and published as EP 3310395 on Apr. 25, 2018 (Inventor—Bowles et al.; Applicant—University of Utah Research Foundation) (17 pages).
Office Action was issued on Jan. 14, 2020 by the European Patent Office for EP Application No. 16812546.6, filed on Jun. 17, 2016 and published as 3310395 on Apr. 25, 2018 (Applicant—Robert D. Bowles) (5 Pages).
International Search Report and Written Opinion were mailed on Mar. 2, 2020 by the International Searching Authority for International Application No. PCT/US2019/056913, filed on Oct. 18, 2019 and published as WO 2020/081922 on Apr. 23, 2020 (Applicant—University of Utah Research Foundation) (13 Pages).
International Preliminary Report on Patentability issued on Apr. 14, 2021 by the International Searching Authority for Patent Application No. PCT/US2019/056913, which was filed on Oct. 18, 2019 and published as WO 2020/081922 on Apr. 23, 2020 (Applicant—Robert D. Bowles) (8 pages).

\* cited by examiner

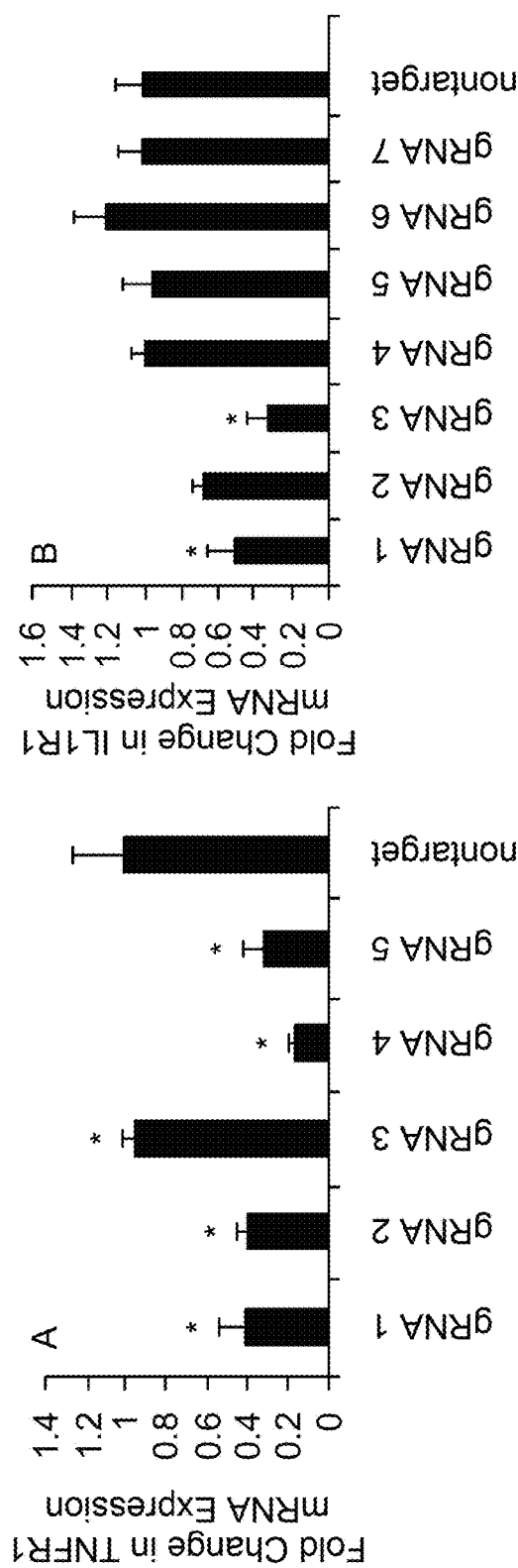
FIG. 12B
FIG. 12A
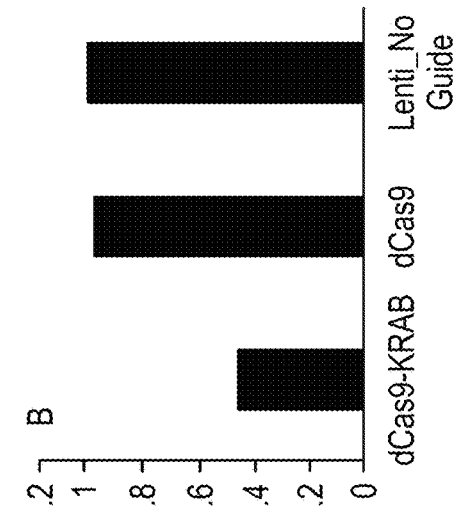
FIG. 13B
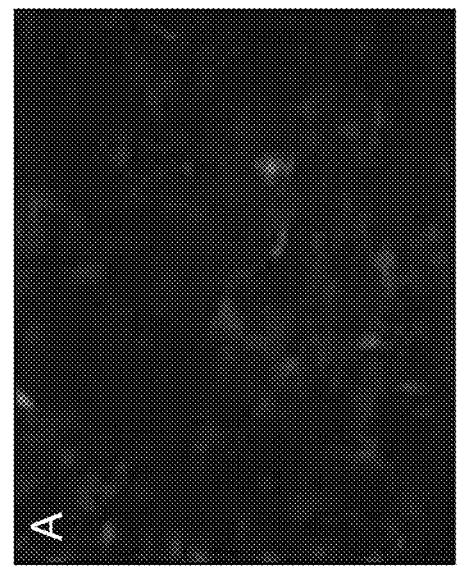
FIG. 13A

FIG. 26A
FIG. 26B
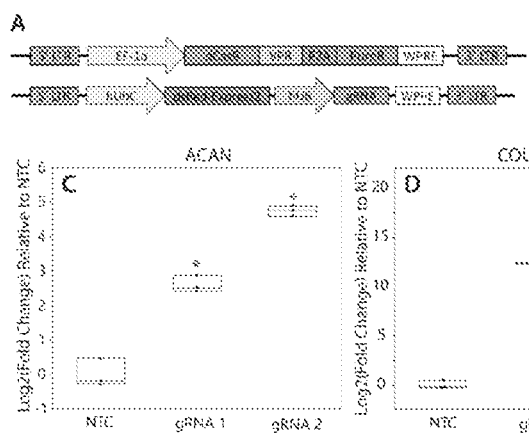
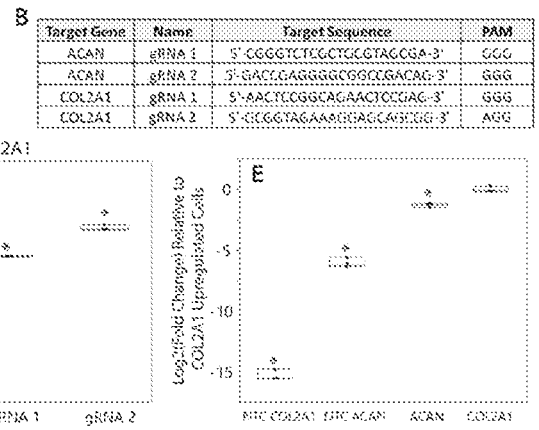
FIG. 26C
FIG. 26D
FIG. 26E

FIG. 29A     FIG. 29B     FIG. 29C
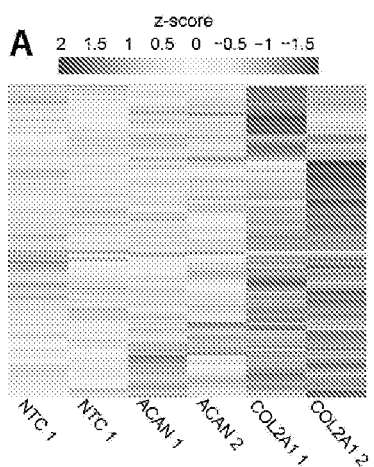
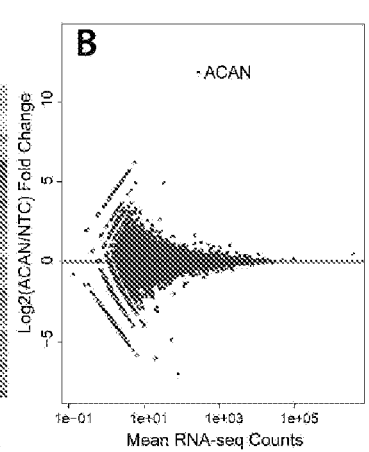
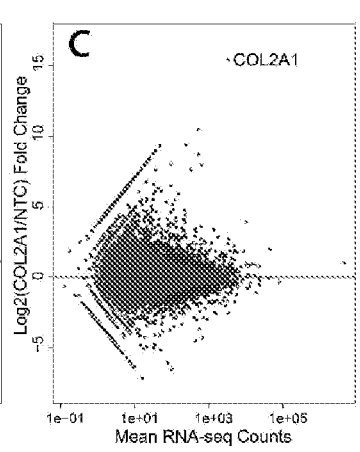
| D    FIG. 29D      Term | Adjusted P-value |
|---|---|
| extracellular matrix organization (GO:0030198) | 6.73E-11 |
| response to endoplasmic reticulum stress (GO:0034976) | 1.35E-09 |
| IRE1-mediated unfolded protein response (GO:0036498) | 1.94E-08 |
| collagen fibril organization (GO:0030199) | 2.49E-07 |
| protein complex subunit organization (GO:0071822) | 4.09E-06 |
| E     Gene | Adjusted P-value | log2foldchange |
|---|---|---|
| Lum | 6.32E-90 | 3.38 |
| BGN | 5.26E-31 | 3.91 |
| CHSY1 | 0.018041 | 0.758344239 |
| CHPF | 0.003147 | 1.139363453 |
| CHSY3 | 2.01E-42 | 4.756339686 |
| CSGALNACT1 | 3.35E-07 | 1.679743136 |
| CSGALNACT2 | 0.03886 | 0.891385761 |
FIG. 29E FIG. 30A
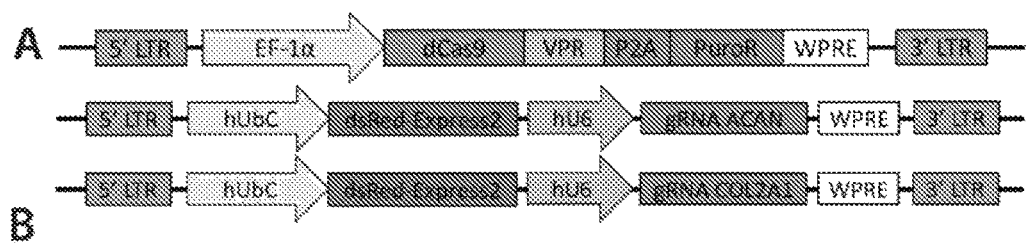
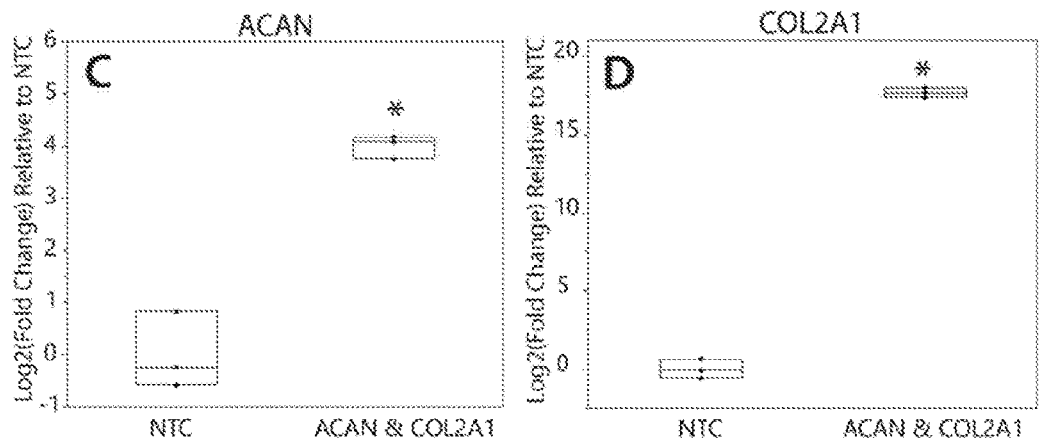
FIG. 30B
FIG. 30C
FIG. 30D

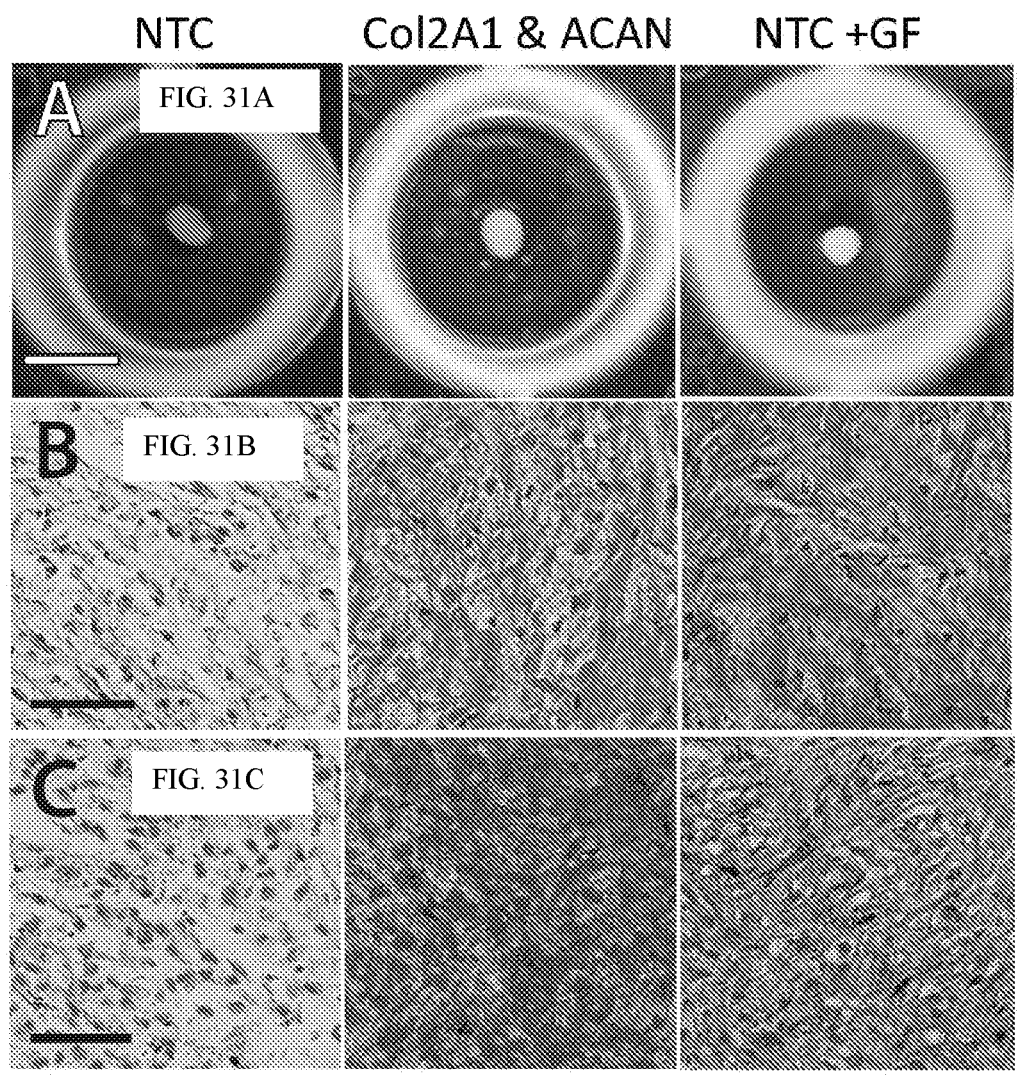

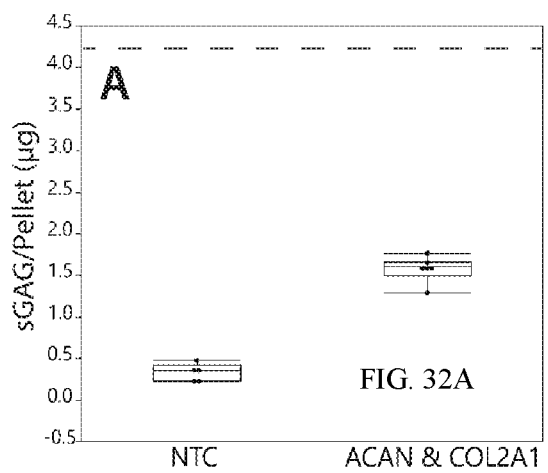
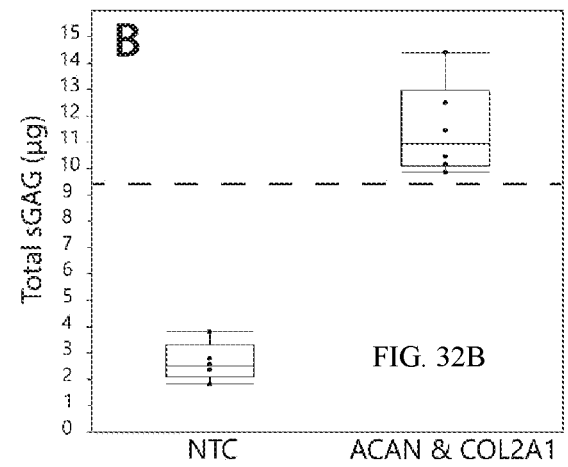
FIG. 32A
FIG. 32B
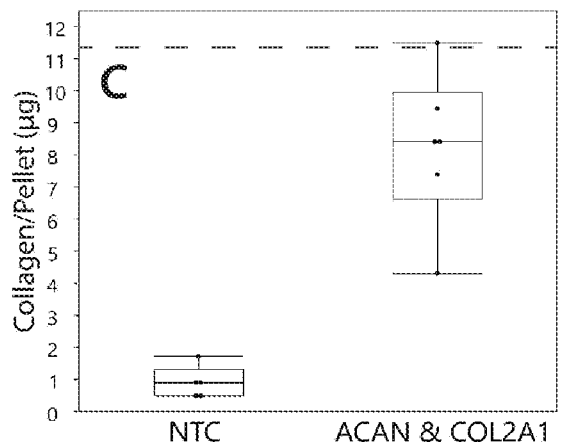
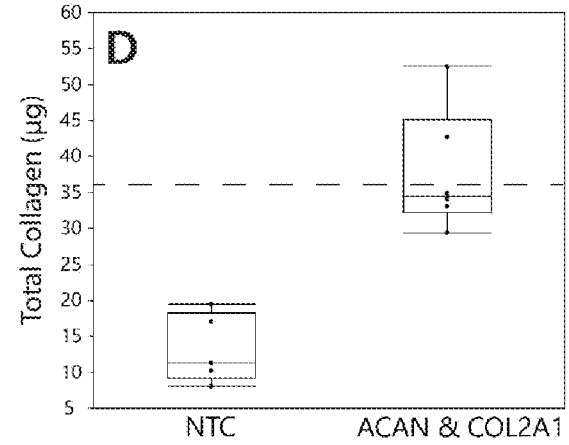
FIG. 32C
FIG. 32D

RNA-GUIDED TRANSCRIPTIONAL REGULATION AND METHODS OF USING THE SAME FOR THE TREATMENT OF BACK PAIN

CROSS REFERENCE TO RELATED APPLICATIONS

This application claims the benefit of priority under 35 U.S.C. § 371 of International Application No. PCT/US2019/056913, filed on Oct. 18, 2019, which claims the benefit of the filing date of U.S. Provisional Application No. 62/747,421, which was filed on Oct. 18, 2018. The content of these earlier filed applications is hereby incorporated by reference herein in its entirety.

INCORPORATION OF THE SEQUENCE LISTING

The present application contains a sequence listing that was submitted in ASCII format via EFS-Web concurrent with the filing of the application, containing the file name 21101_0378U2_SL.txt, which is 32,768 bytes in size, created on Apr. 12, 2021, and is herein incorporated by reference in its entirety pursuant to 37 C.F.R. § 1.52(e)(5).

BACKGROUND

Lower back pain (LBP) is the single leading cause of disability worldwide having a global lifetime prevalence of 38.9%. Degenerative disc disease (DDD) and associated pathologies are considered major contributors to LBP. The progression of DDD is associated with an inflammatory environment that includes the presence of inflammatory cytokines (e.g., TNF-α, IL-Iβ) in the intervertebral disc (IVD) that are active in the degenerative process and may sensitize pain-sensing nerve fibers in the IVD.

Although both surgical and non-surgical treatments for DDD-induced LBP are able to alleviate symptoms, they, however, fail to prevent the progression of disc degeneration, thus, LBP often returns after treatment. To effectively treat DDD-induced LBP on a long-term basis, therapeutic methods that can slow DDD progression and reduce the need for surgical intervention are needed. DDD and its progression have been associated with the action of inflammatory cytokines in the intervertebral disc (IVD) that signal the breakdown of the extracellular matrix through their respective receptors. Therefore a method for effectively slowing DDD progression that inhibits the catabolic signaling of these inflammatory cytokines in the IVD is also needed.

Applying stem cell technologies to musculoskeletal tissue engineering and cell therapies is of current interest in the field. However, the success of these strategies is limited, as stem cells implanted into challenging disease environments struggle to maintain an exemplary phenotype. Regulating the phenotype of stem cells has largely been accomplished by controlled growth factor treatment. Methods to control cell phenotype without growth factors to effectively slow DDD progression is also needed.

SUMMARY

Disclosed herein, are CRISPR-Cas systems comprising one or more vectors comprising: a) a promoter operably linked to one or more nucleotide sequences encoding a CRISPR-Cas system guide RNA (gRNA), wherein the gRNA hybridizes with a target sequence of a DNA locus in a cell; and b) a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA locus; and wherein the gRNA sequence is selected from the group listed in Table 6.

Disclosed herein, are vectors comprising promoters operably linked to one or more nucleotide sequences encoding a CRISPR-Cas system guide RNA (gRNA); and regulatory elements operably linked to a nucleotide sequence encoding a RNA-directed nuclease; wherein the gRNA sequence is selected from the group listed in Table 6.

Disclosed herein, are methods of modulating of genes in cells, the methods comprising: introducing into the cells a first nucleic acid encoding a guide RNA (gRNA), wherein the gRNA comprises a DNA-binding domain, wherein the nucleic acid is operably linked to a regulatory element, wherein the gRNA is complementary to a target nucleic acid sequence comprising the gene; introducing into the cell a second nucleic acid encoding a transcriptional regulator protein or domain that modulates the target nucleic acid expression, and comprises a gRNA-binding domain, wherein the second nucleic acid is operably linked to a regulatory element; and introducing into the cell a third nucleic acid encoding a deactivated nuclease Cas9 (dCas9) protein, wherein the third nucleic acid is operably linked to a regulatory element, wherein the dCas9 protein interacts with the gRNA and is fused to the transcriptional regulator protein; wherein the cell produces the gRNA that binds the dCas9 protein and the transcriptional regulator protein or domain fused to the DNA-binding domain; wherein the guide RNA and the dCas9 protein co-localize to the target nucleic acid sequence and wherein the transcriptional regulator protein or domain modulates expression of the gene; wherein the gRNA sequence is selected from the group listed in Table 2 and Table 4.

Disclosed herein, are methods of modulating of genes in cells, the methods comprising: introducing into the cells a first nucleic acid encoding a guide RNA (gRNA), wherein the gRNA comprises a DNA-binding domain, wherein the nucleic acid is operably linked to a regulatory element, wherein the gRNA is complementary to a target nucleic acid sequence comprising the gene; introducing into the cell a second nucleic acid encoding a transcriptional regulator protein or domain that modulates the target nucleic acid expression, and comprises a gRNA-binding domain, wherein the second nucleic acid is operably linked to a regulatory element; and introducing into the cell a third nucleic acid encoding a deactivated nuclease Cas9 (dCas9) protein, wherein the third nucleic acid is operably linked to a regulatory element, wherein the dCas9 protein interacts with the gRNA and is fused to the transcriptional regulator protein; wherein the cell produces the gRNA that binds the dCas9 protein and the transcriptional regulator protein or domain fused to the DNA-binding domain; wherein the guide RNA and the dCas9 protein co-localize to the target nucleic acid sequence and wherein the transcriptional regulator protein or domain modulates expression of the gene; wherein the gRNA sequence is selected from the group listed in Table 2, Table 4 and Table 6.

Disclosed herein, are methods of increasing expression of one or more genes in cells, the methods comprising: introducing into the cells a first nucleic acid encoding a guide RNA (gRNA), wherein the gRNA comprises a DNA-binding domain, wherein the nucleic acid is operably linked to a regulatory element, wherein the gRNA is complementary to a target nucleic acid sequence comprising the gene; introducing into the cell a second nucleic acid encoding a transcriptional regulator protein or domain that modulates the target nucleic acid expression, and comprises a gRNA-binding domain, wherein the second nucleic acid is operably linked to a regulatory element; and introducing into the cell a third nucleic acid encoding a deactivated nuclease Cas9 (dCas9) protein, wherein the third nucleic acid is operably linked to a regulatory element, wherein the dCas9 protein interacts with the gRNA and is fused to the transcriptional regulator protein; wherein the cell produces the gRNA that binds the dCas9 protein and the transcriptional regulator protein or domain fused to the DNA-binding domain; wherein the guide RNA and the dCas9 protein co-localize to the target nucleic acid sequence and wherein the transcriptional regulator protein or domain increases expression of the gene; wherein the gRNA sequence is selected from the group listed in Table 6.

Disclosed herein, are methods for introducing into a cell a CRISPR-Cas system comprising one or more vectors, the method comprising: a promoter operably linked to one or more nucleotide sequences encoding a CRISPR-Cas system guide RNA (gRNA), wherein the gRNA hybridizes with a target sequence of a DNA molecule in a cell; a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA molecule; wherein the gRNA sequence is selected from the group listed in Table 6.

Disclosed herein, are methods for introducing into a cell a vector comprising: a promoter operably linked to one or more nucleotide sequences encoding a CRISPR-Cas system guide RNA (gRNA); a regulatory element operably linked to a nucleotide sequence encoding a RNA-directed nuclease; wherein the gRNA sequence is selected from the group listed in Table 6.

Disclosed herein, are methods of treating a subject having degenerative disc disease, the method comprising: (a) determining the subject has degenerative disc disease; and (b) administering to the subject a pharmaceutical composition comprising a nucleic acid sequence encoding a CRISPR-associated deactivated endonuclease and one or more guide RNAs, wherein the guide RNA is selected from the group listed in Table 6 and Table 4. Disclosed herein are methods of treating a subject having degenerative disc disease, the method comprising: (a) determining ACAN, Col2A1, IL-10, and/or IDO1 levels in the subject; and (b) administering to the subject a pharmaceutical composition comprising a nucleic acid sequence encoding a CRISPR-associated deactivated endonuclease and one or more guide RNAs, wherein the guide RNA is selected from the group listed in Table 6.

Other features and advantages of the present compositions and methods are illustrated in the description below, the drawings, and the claims.

BRIEF DESCRIPTION OF THE DRAWINGS

FIG. 1A is a representative calcium signal (ΔF/F) for a neuron firing in response to heat stimuli. DRG neurons were considered to have fired when the ΔF/F for the neuron exceeded the threshold level defined as the mean ΔF/F value at baseline plus three standard deviations. FIG. 1B shows calcium images of representative DRG neurons at baseline, immediately following heat application (FIG. 1C), at maximum response to heat stimuli (FIG. 1D), and return to baseline following stimuli (FIG. 1E).

FIG. 2A shows the firing response of rat DRG neurons as a function of temperature was fitted to a Boltzmann curve for the degenerative IVD conditioned media (n=5 patients), healthy IVD conditioned media (n=3) patients), and control media groups. The T50 (FIG. 2B) and maximum (FIG. 2C) generated from dose response curve fitting for the degenerative IVD conditioned media, healthy IVD conditioned media, and control media groups. *=p<0.05 when compared to the control media group for the same temperature. #=p<0.05 when compared to the healthy IVD conditioned media group for the same temperature.

FIG. 3A shows the mean Boltzmann curve fittings of neuron response to thermal stimuli for the control media, conditioned media plus IL-6 antibody, conditioned media, and conditioned media plus isotype control antibody groups. The maximum (FIG. 3B) and T50 (FIG. 3C) generated from dose response curve fitting for the control media, conditioned media plus TL-6 antibody (20 µg/mL), conditioned media plus isotype control antibody (20 µg/mL), and conditioned media groups (n=5). FIG. 3D shows the percentage of DRG neurons firing in response to temperatures of 39° C. and 44° C. when exposed to conditioned media or conditioned media plus TL-6 antibody. FIG. 3A-C, Values are mean±standard deviations. N=5 for all groups tested. *=p<0.05 compared to the control media group at the same temperature. #=p<0.05 compared to the conditioned media plus TL-6 antibody group at the same temperature. FIG. 3D is table showing the values as a percentage of neurons firing in response to thermal stimuli.*=p<0.05 compared to the conditioned media plus TL-6 antibody group for the same patient at the same temperature.

FIG. 6A shows CRISPR based epigenomic editing vectors contains sgRNAs that directs the dCas9 endonuclease fused with KRAB to the PAM binding sequence of the genomic DNA leading to the expression of KRAB. FIG. 6B shows gene expression occurs when chromatin is maintained in the euchromatin (open) configuration by acetylation of the H3K9 histones. Expression of KRAB recruits endogenous factors that replace acetylation of H3K9 with tri-methylation, maintaining chromatin in the heterochromatic state, silencing gene expression. FIG. 6C shows the vector map of CRISPR epigenome editing targeting the AKAP 150 gene. FIG. 6D shows epigenome editing of AKAP 150 expression in rat DRG neurons. FIG. 6E shows the mean Boltzman fit curves of neuron firing response to thermal stimuli for naïve neurons exposed to control media and naïve cells, AKAP epigenome edited cells and non-target epigenomically edited neurons exposed to degenerative IVD conditioned media. The T50 (FIG. 6F) and maximum response (FIG. 6G)

generated from the dose response curve from naïve neurons exposed to control media and naïve cells, AKAP epigenome edited cells and non-target epigenomically edited neurons exposed to degenerative IVD conditioned media.

Figures 7A, 7B, 7C, 7D:
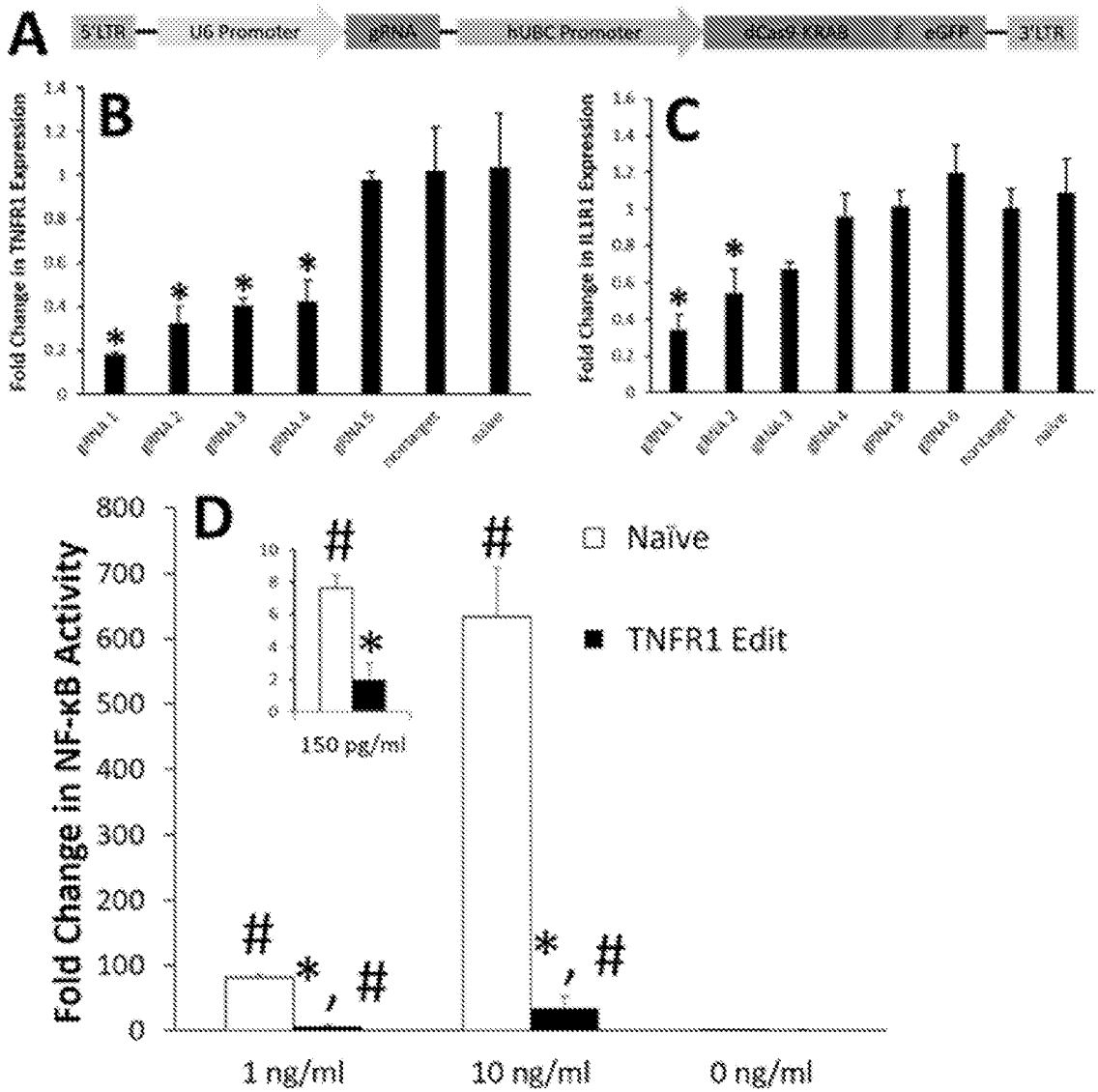

FIGS. 7A-D show the results of screening for efficient epigenome editing in HEK293T cells. FIG. 7A shows the lentiviral cassette demonstrating components of the epigenome editing system and how their expression is driven. FIG. 7B is a bar graph showing the screening of gRNAs for TNFR1 significantly downregulated by 4 gRNAs. FIG. 7C is a bar graph showing the screening of gRNAs for IL1R1 significantly downregulated by 2 gRNAs. (* denotes p<0.05 compared to nontarget control). FIG. 7D shows a fold change in NF-κB activity in response to TNF-α dosing in HEK293T cells with TNFR1 edit mediated by gRNA 1 (*=p<0.05 (TNFR1/IL1R1 Edit vs. Naïve), #=p<0.05 (TNF-α/IL-1β dose vs. no dose control)).

Figures 8A, 8B:
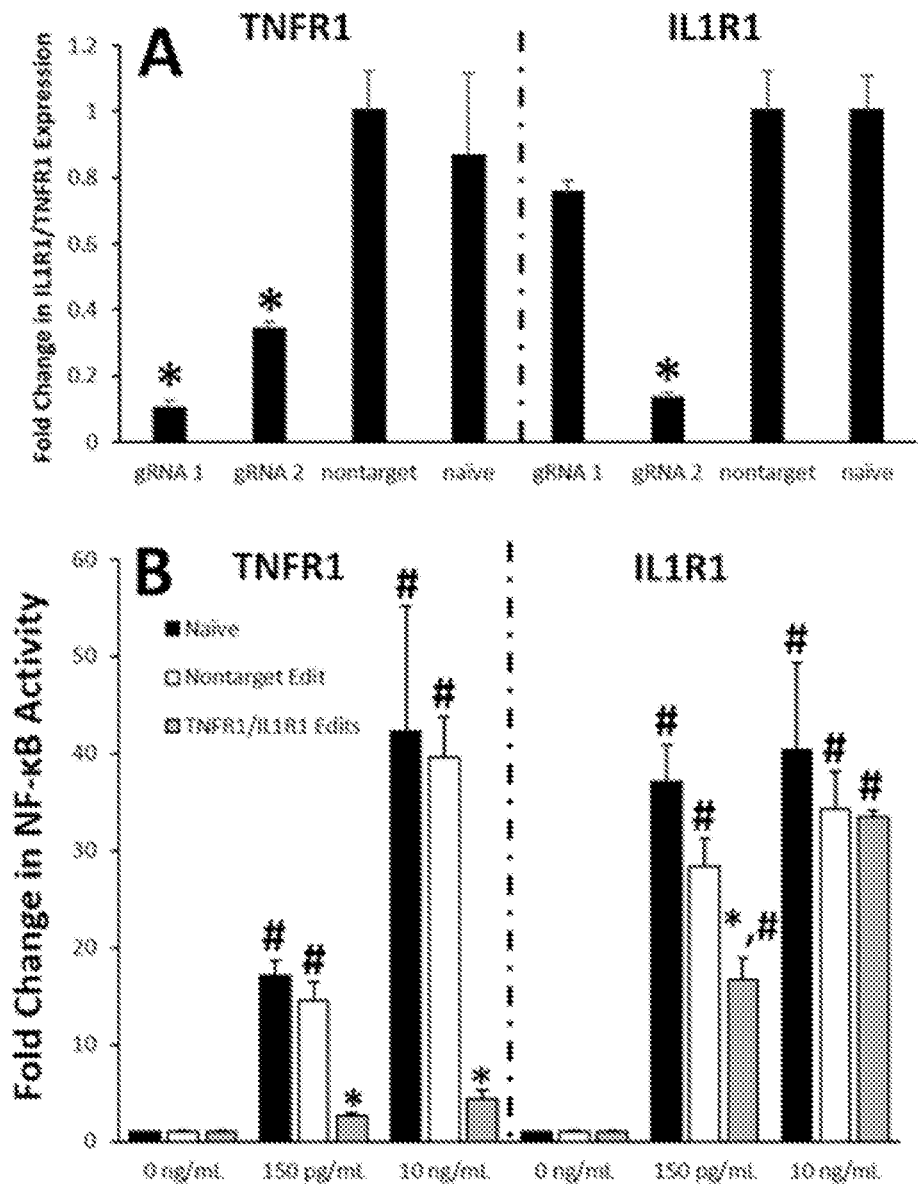

FIGS. 8A-B show lentiviral mediated gene and receptor signaling downregulation in hADMSCs. FIG. 8A shows TNFR1 and IL1R1 expression in hADMSCs post-transduction of epigenome editing system under the control of selected gRNAs. FIG. 8B shows changes in NF-kB activity post TNF-α/IL-1β dosing in epigenome edited hADMSCs which express the epigenome editing system with the most efficient guides for each receptor (*=p<0.05 (TNFR1/IL1R1 Edits vs. nontarget Edit), #=p<0.05 (TNF-α/IL-1β dose vs. no dose control)).

Figures 9A, 9B, 9C, 9D, 9E, 9F:
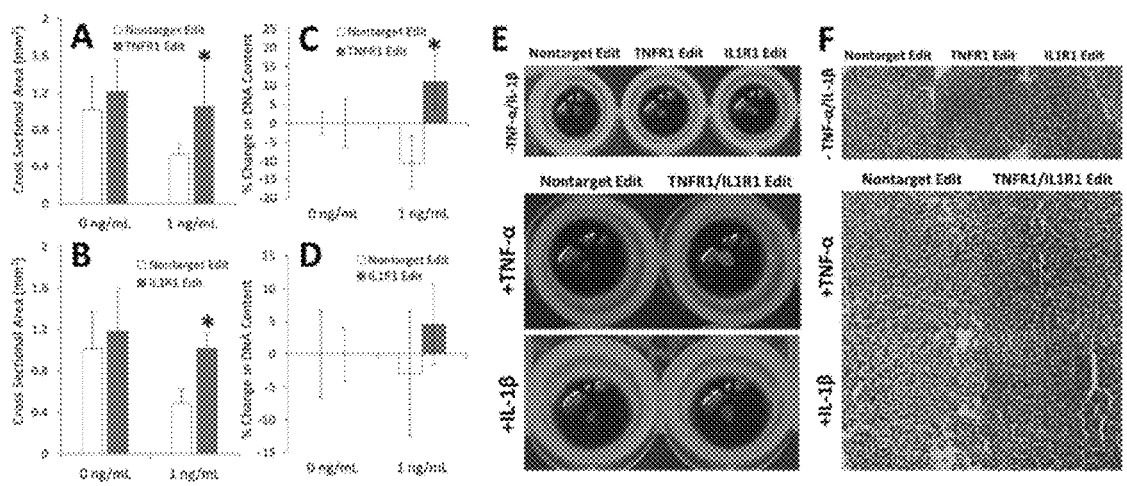

FIGS. 9A-F show cell proliferation and ECM deposition in 3D culture by epigenome edited cells in the presence of cytokines. FIGS. 9A and 9B show the cross sectional area of cell pellets in mm$^2$, cultured with or without TNF-α/IL-1β (n=6). FIGS. 9C and 9D show percent changes in DNA content relative to undosed control (n=4-5). FIG. 9E is a representative image of hADMSC pellets, demonstrating visible size differences between TNFR1/IL1R1 edit cells and non-target edit control under inflammatory conditions. FIG. 9F shows H & E staining of cell pellets visualizing relative ECM content show lighter ECM staining in dosed non-target edit cells but not in TNFR1/IL1R1 edited cells. (* denotes p<0.05 compared to dosed nontarget edit control).

Figures 10A, 10B, 10C, 10D, 10E, 10F:
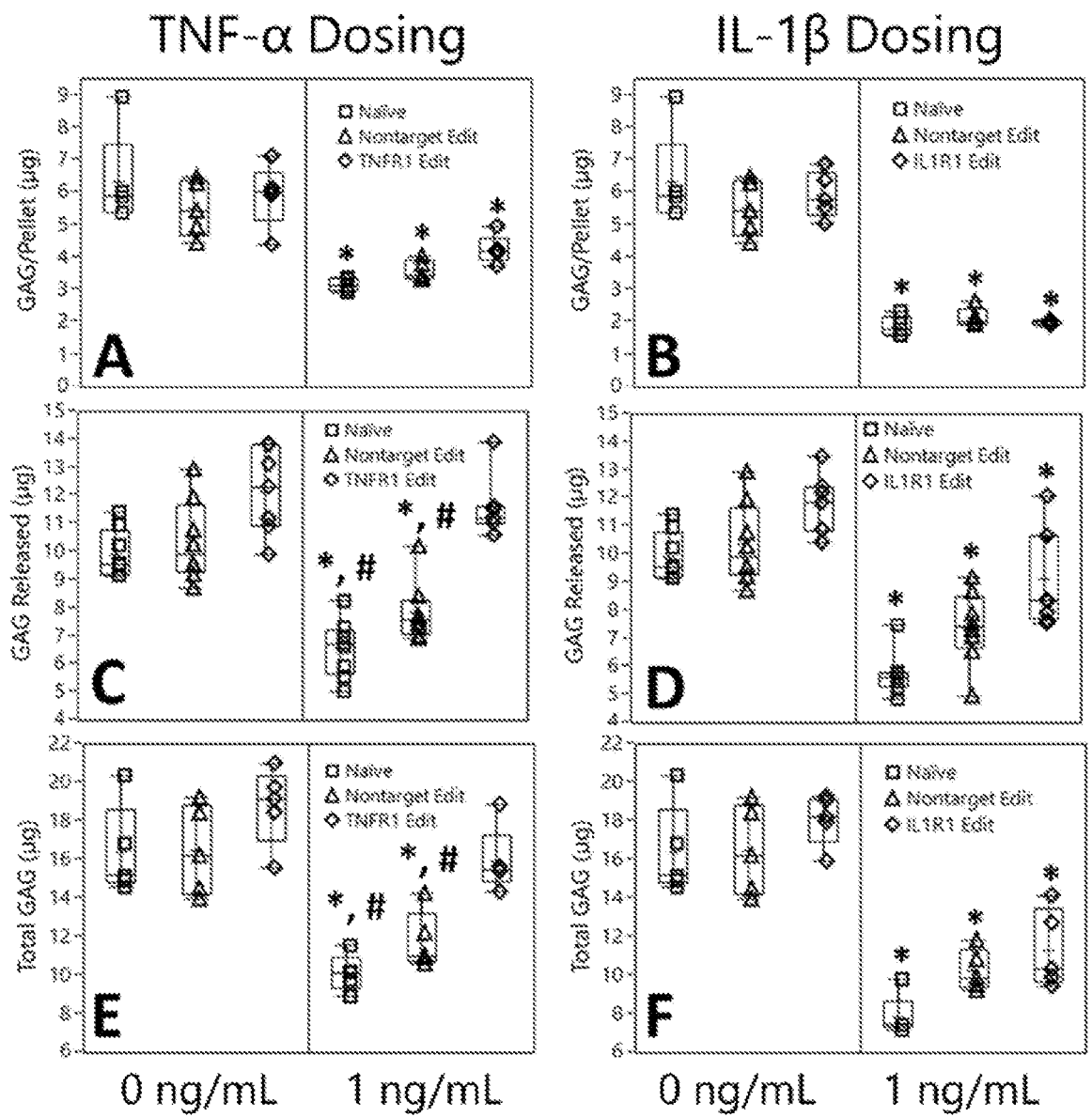

FIGS. 10A-F show the results of quantification of GAG contents in pellet cultures that have undergone chondrogenic differentiation for 3 weeks with or without the presence of TNF-α/IL-1β. FIGS. 10A and 10B show GAG content per pellet (n=5). FIGS. 10C and 10D) show the amount of GAG released into media during culture (n=7-8). FIGS. 10E and 10F show the sum of GAG content that was released and within cell pellets (n=5). (*=p<0.05 relative to 0 ng/mL control, #=p<0.05 relative to dosed TNFR1 edited cells.)

Figures 11A, 11B:
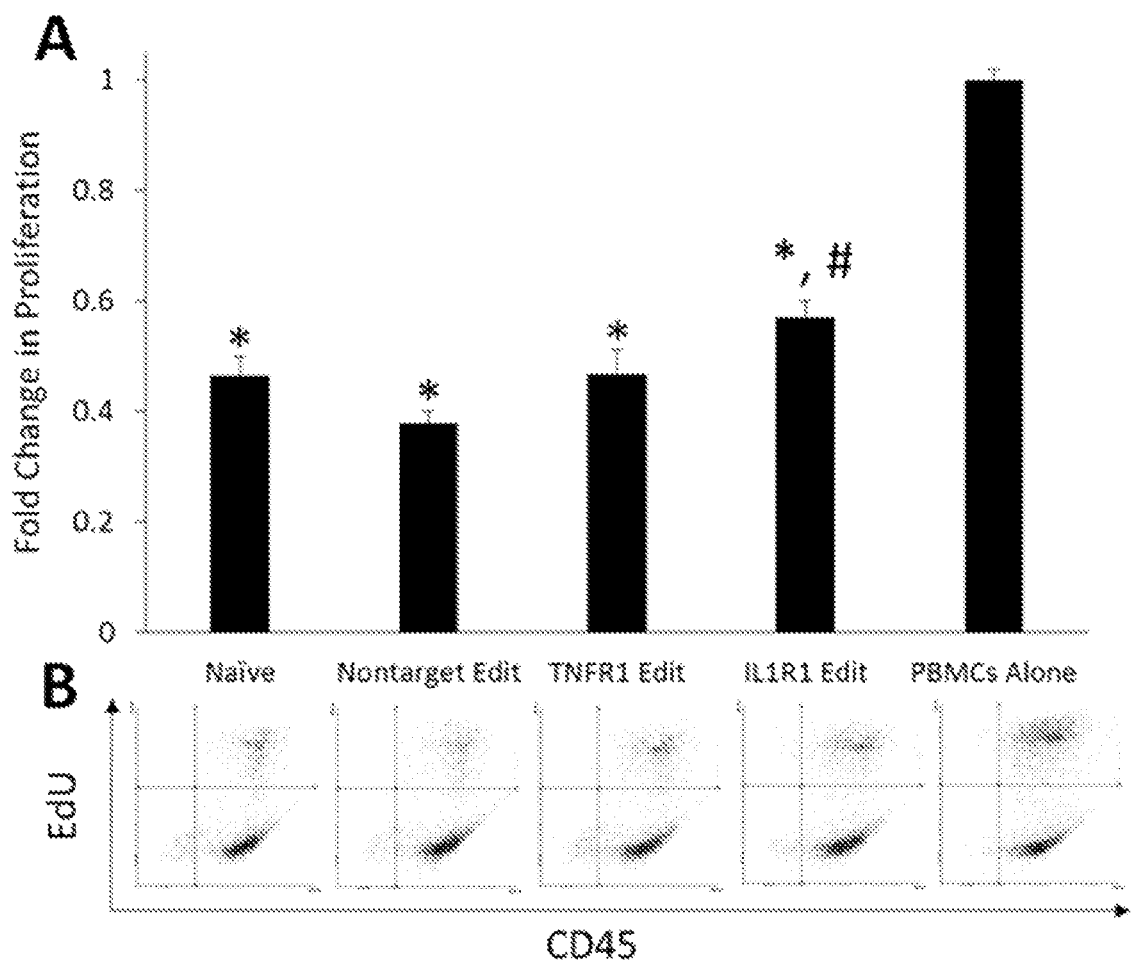

FIGS. 11A-B show the ability of epigenome edited hADMSCS to suppress PBMC proliferation in coculture. FIG. 11A shows the fold change in proliferation relative to PBMCs alone demonstrate suppression of PBMC proliferation by all hADMSCs (n=4). FIG. 11B shows a representative flow cytometry graph of PBMCs demonstrating a visible decrease in CD45 EdU positive cells (graphs represent condition they are directly beneath in part A graph). (*=p<0.05 relative to PBMCs alone, #=p<0.05 relative to coculture with naïve hADMSCs.) FIGS. 12A-B show knockdown of TNFR1 (A) and IL1R1 (B) with multiple promoter-targeting gRNAs (*=P<0.05 compared to non-target control).

FIGS. 13A-B show transduced primary human NP cells (A) expressing CRISPRi system as evidenced by GFP expression and the knockdown of TNFR1 in NP cells using TNFR1 CRISPRi lentiviral vector (B).

Figure 14:
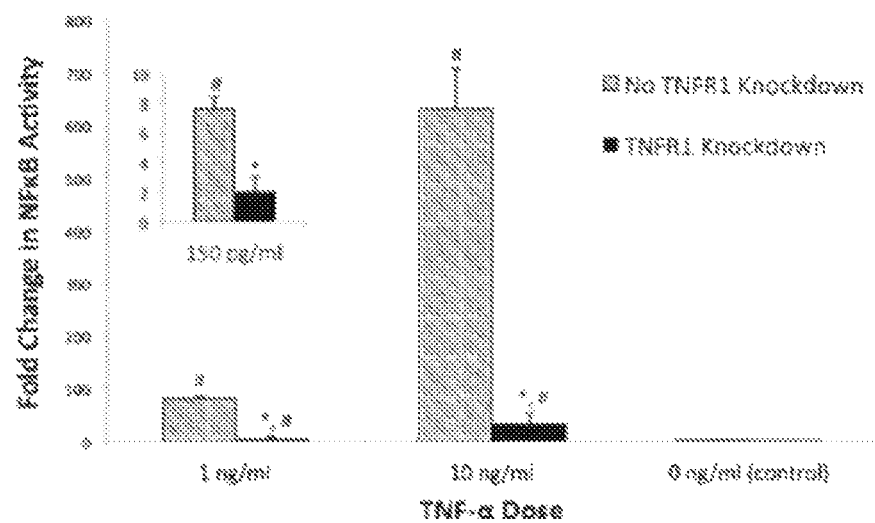

FIG. 14 shows the fold change in NF-KB activity by HEK293T cells dosed with TNF-α. Differences between the knockdown and the number of knockdown cells are statistically significant (P<0.05) for each dose as denoted by *.

Figure 15:
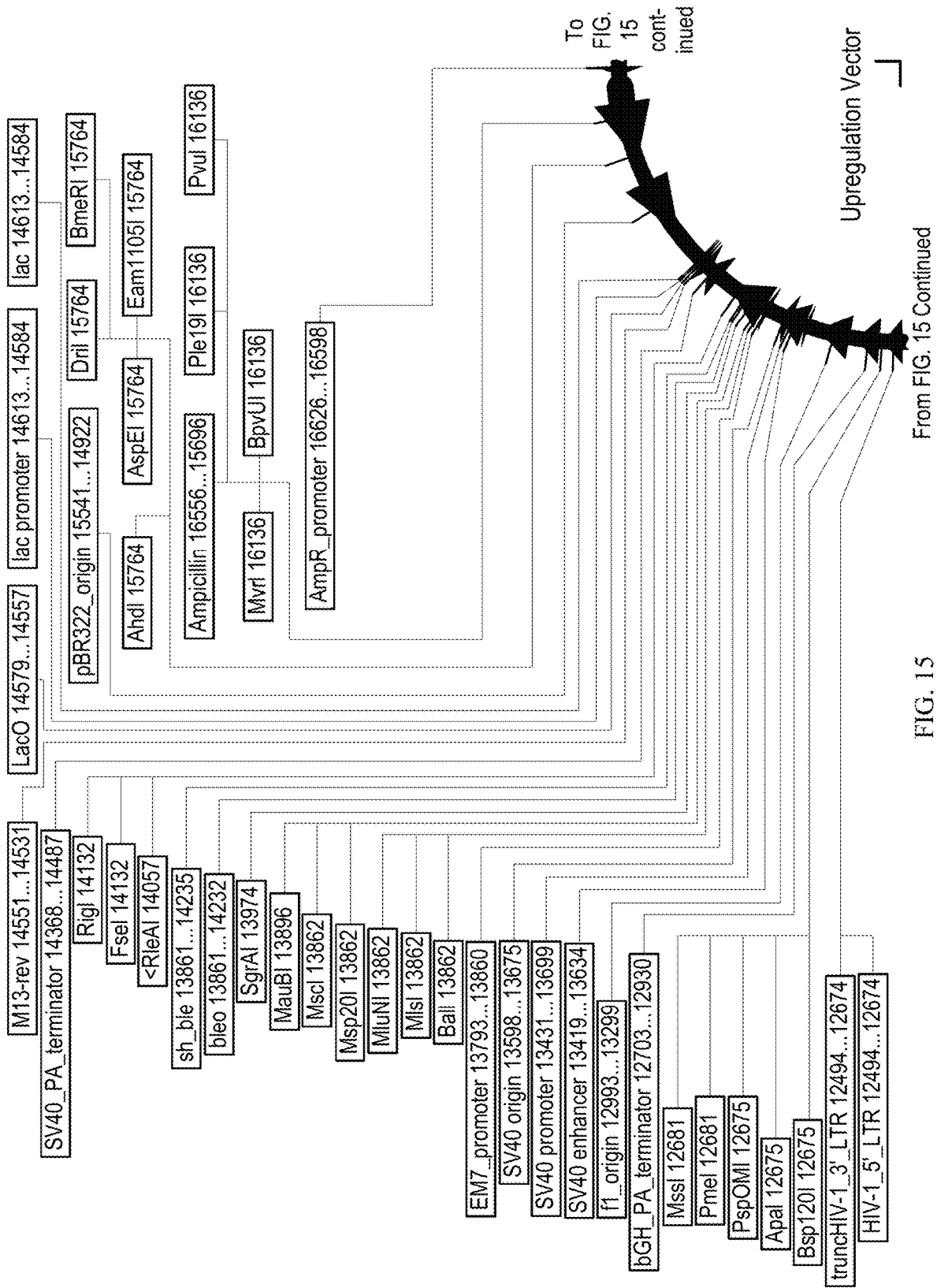
Figure 15:
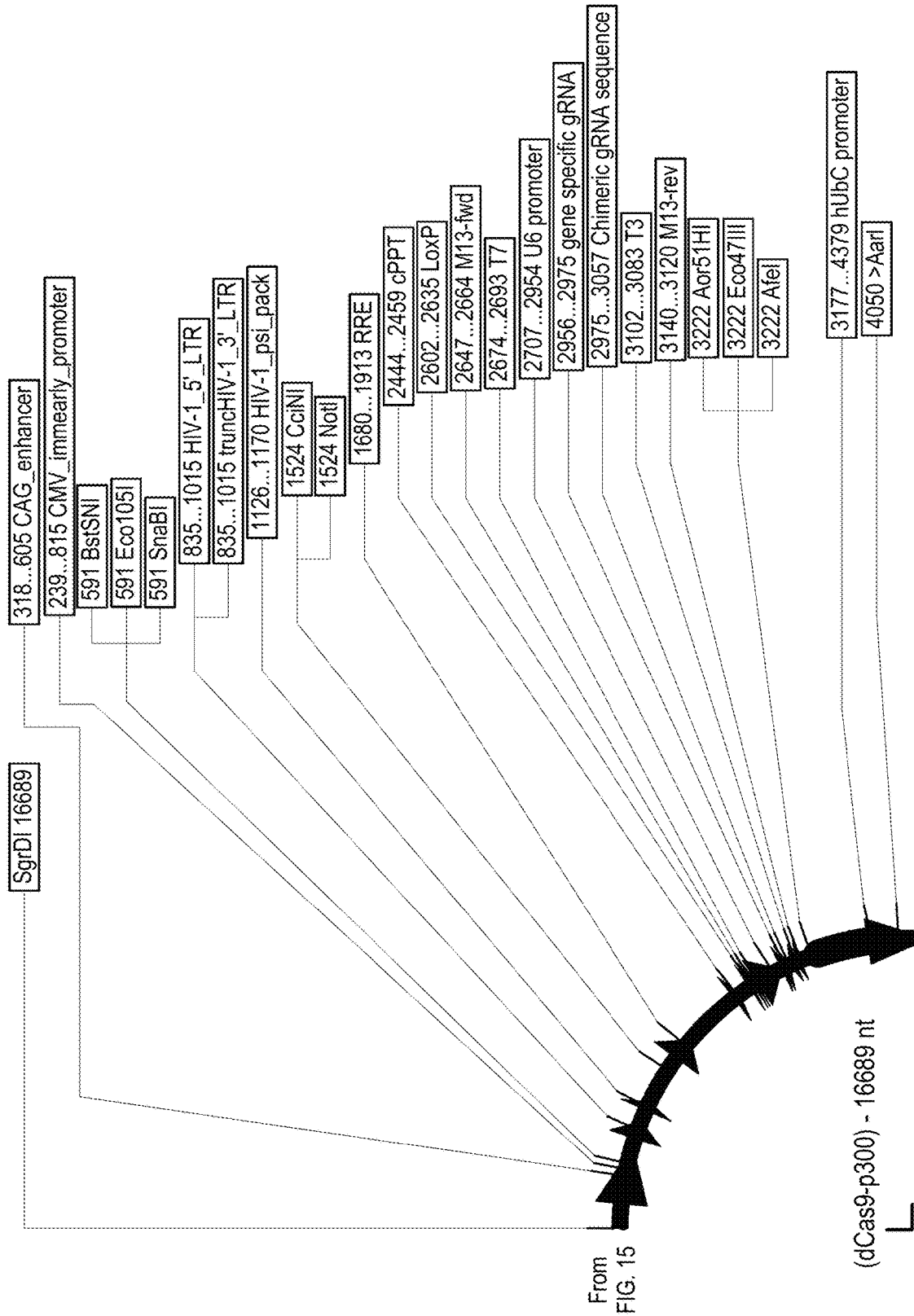
Figure 15:
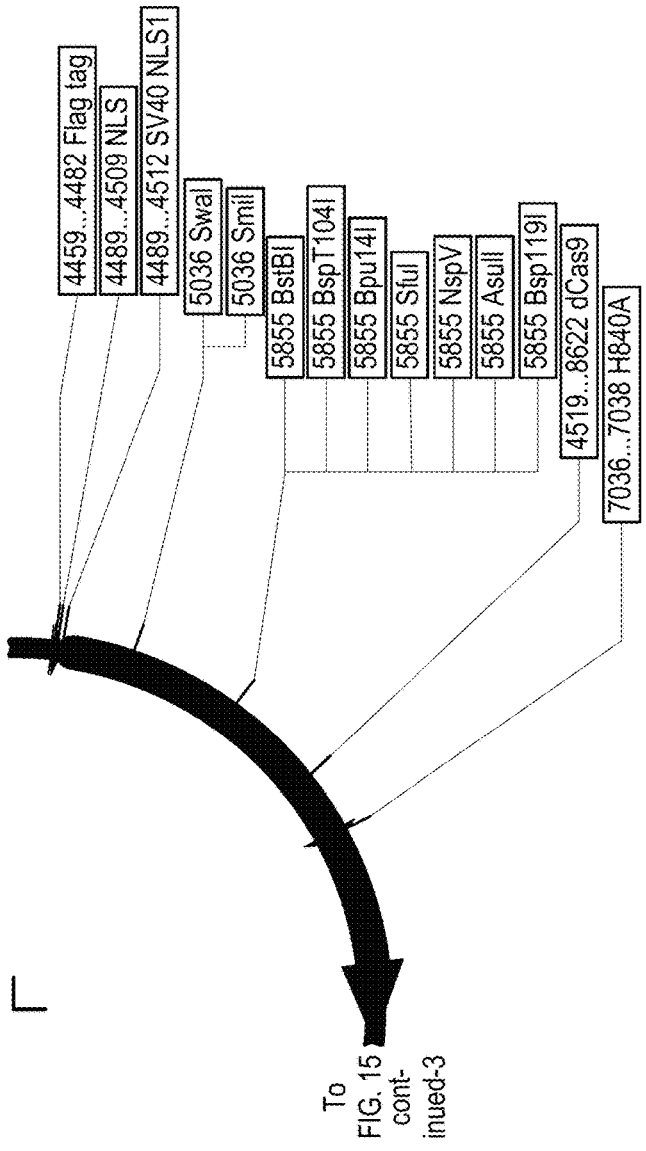
Figure 15:
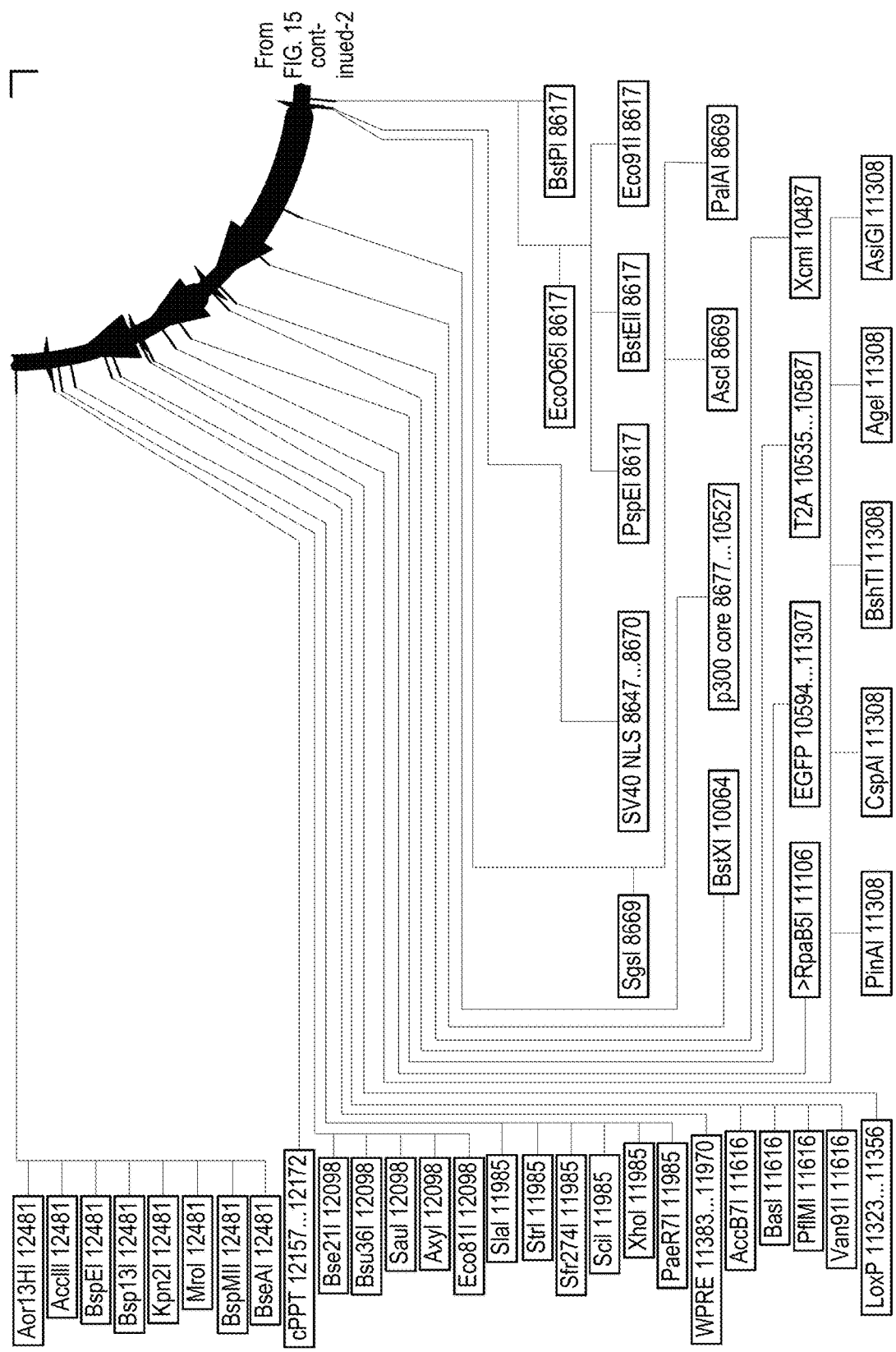

FIG. 15 shows an example of a singleplex upregulation vector. The vector shown comprises dCas9-p300 core.

Figure 16:
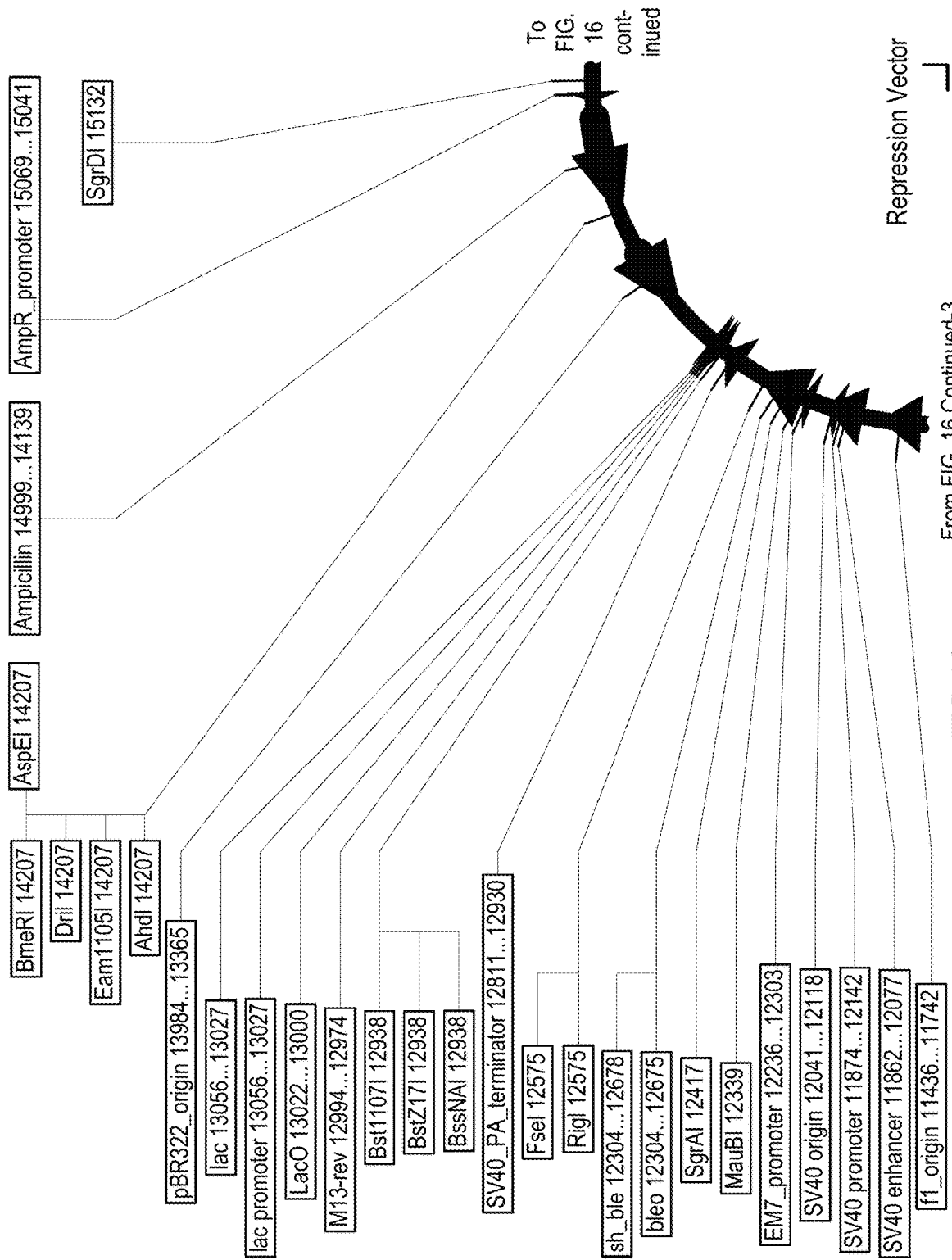
Figure 16:
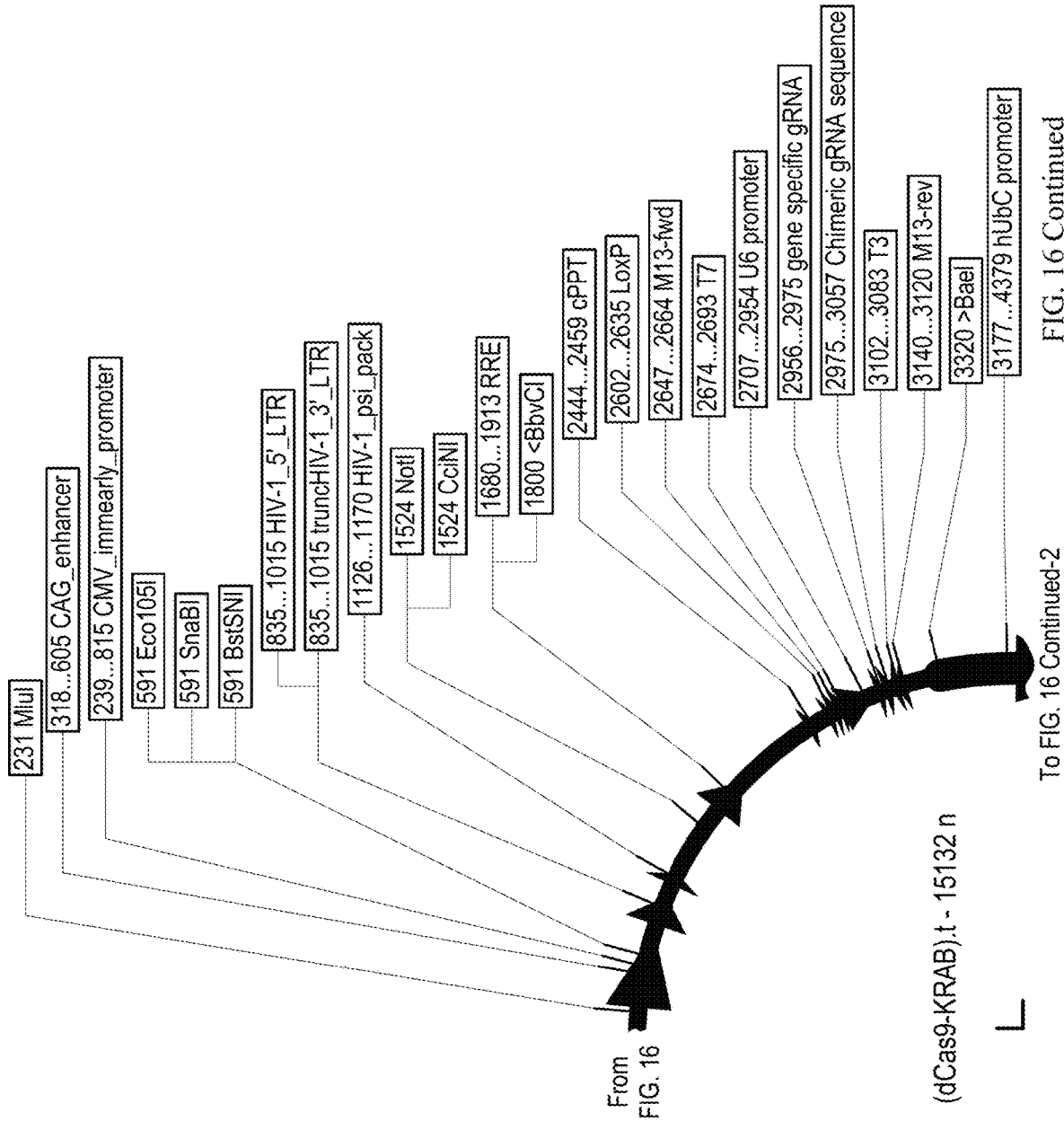
Figure 16:
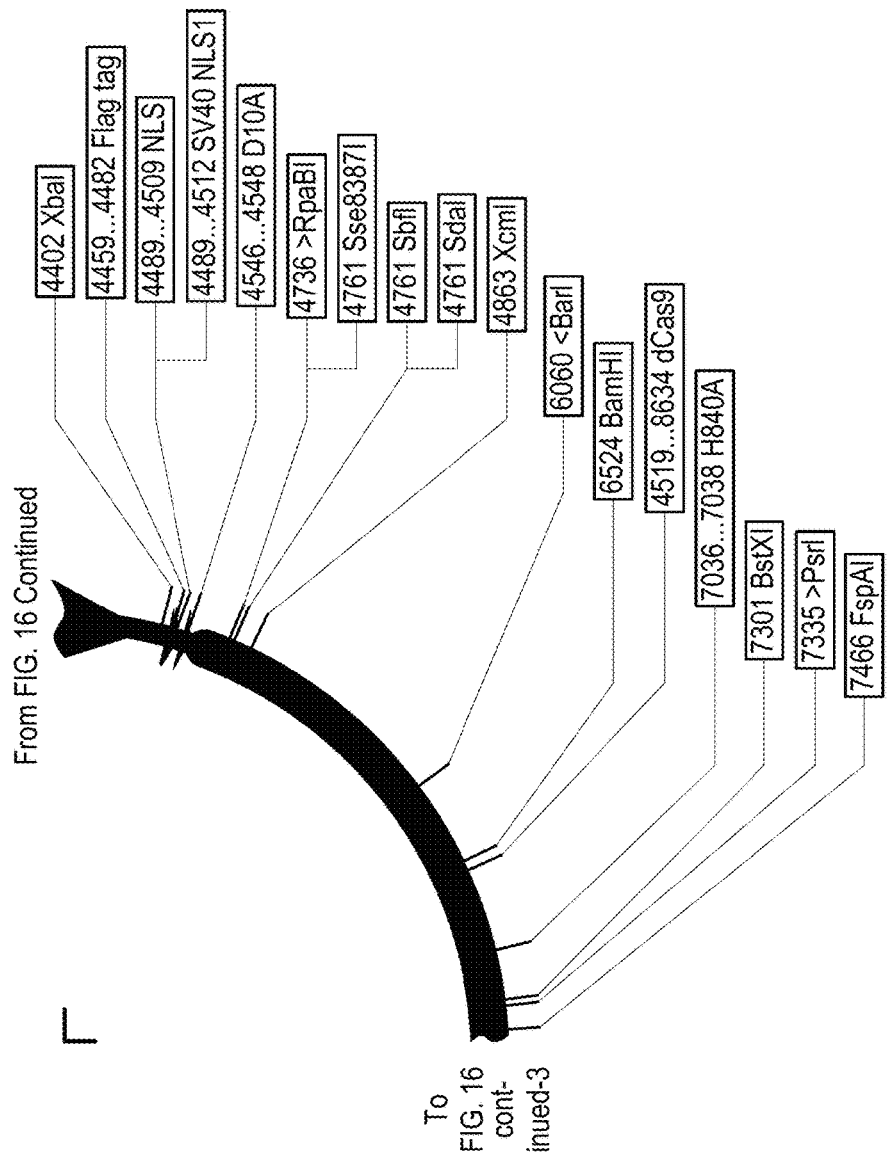
Figure 16:
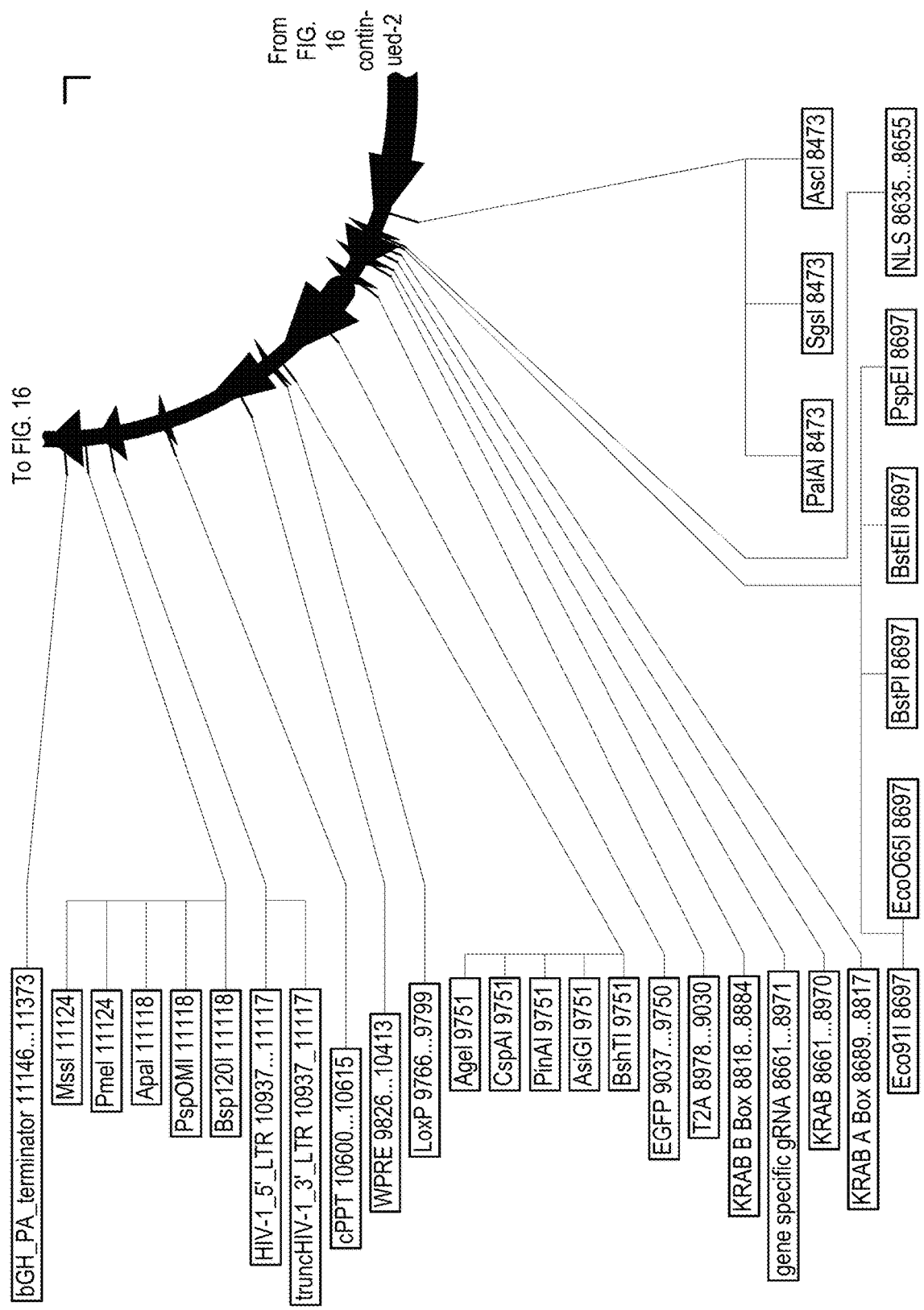

FIG. 16 shows an example of a singleplex upregulation vector. The vector shown comprises dCas9-KRAB.

Figure 17:
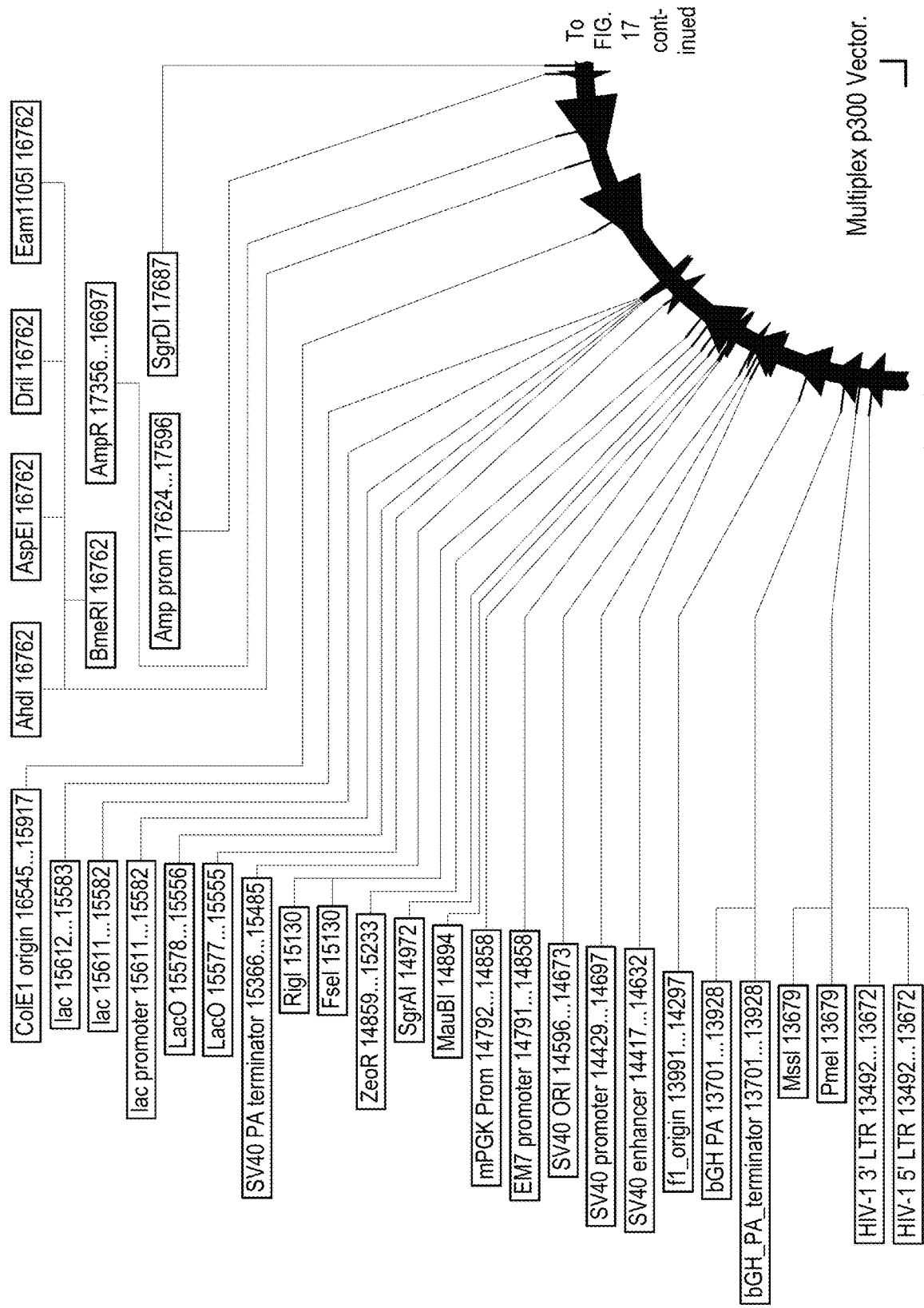
Figure 17:
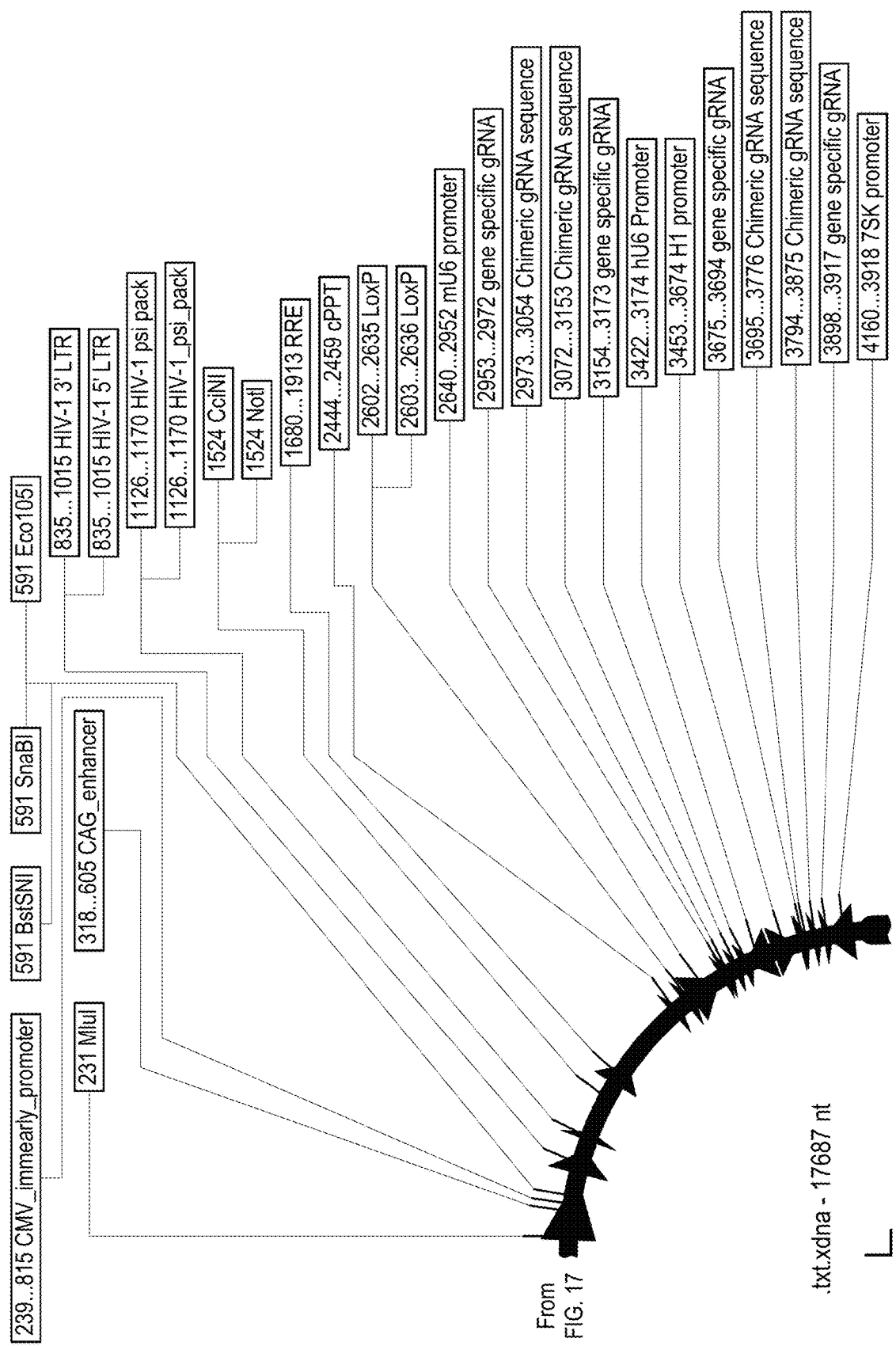
Figure 17:
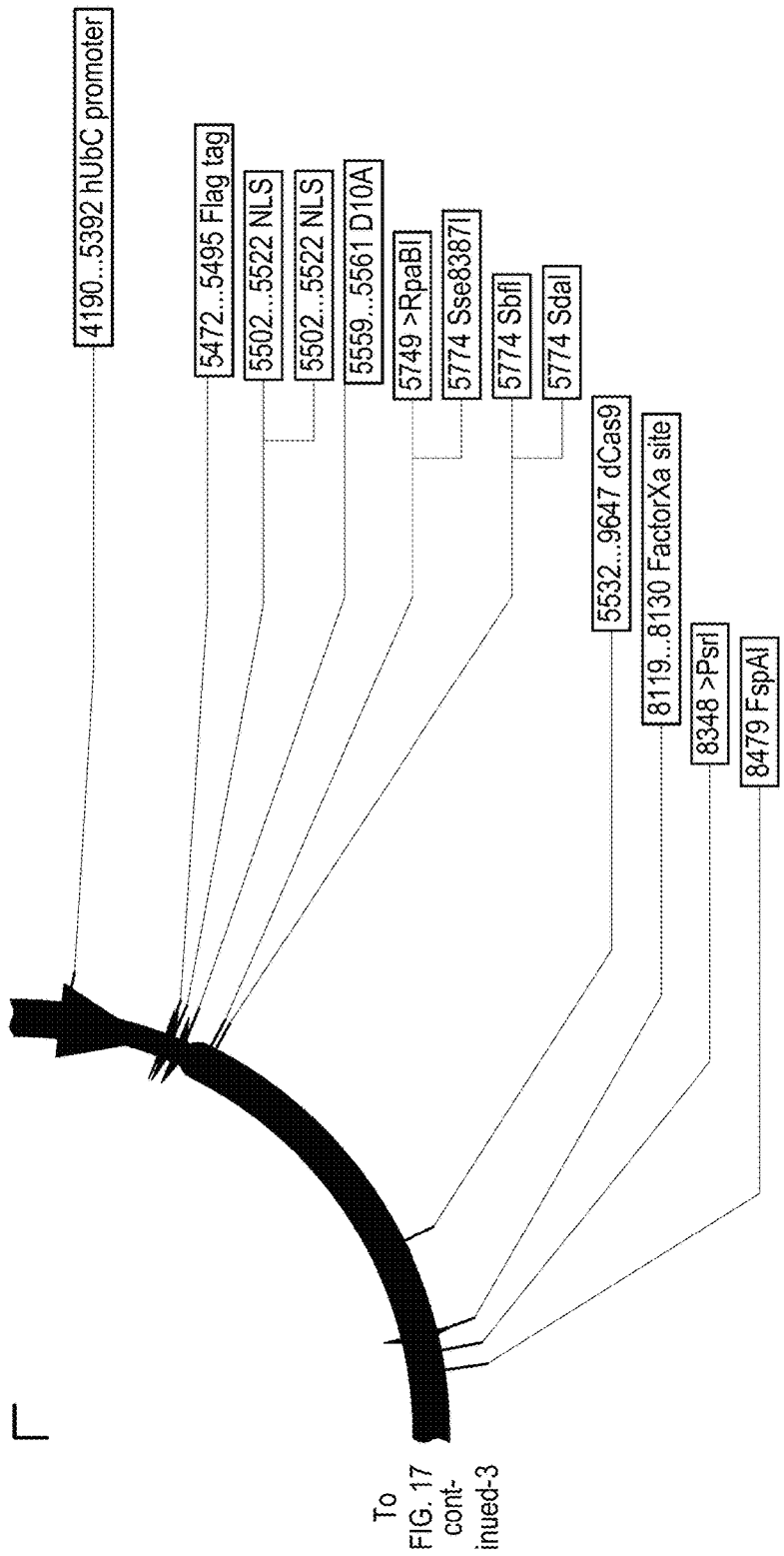
Figure 17:
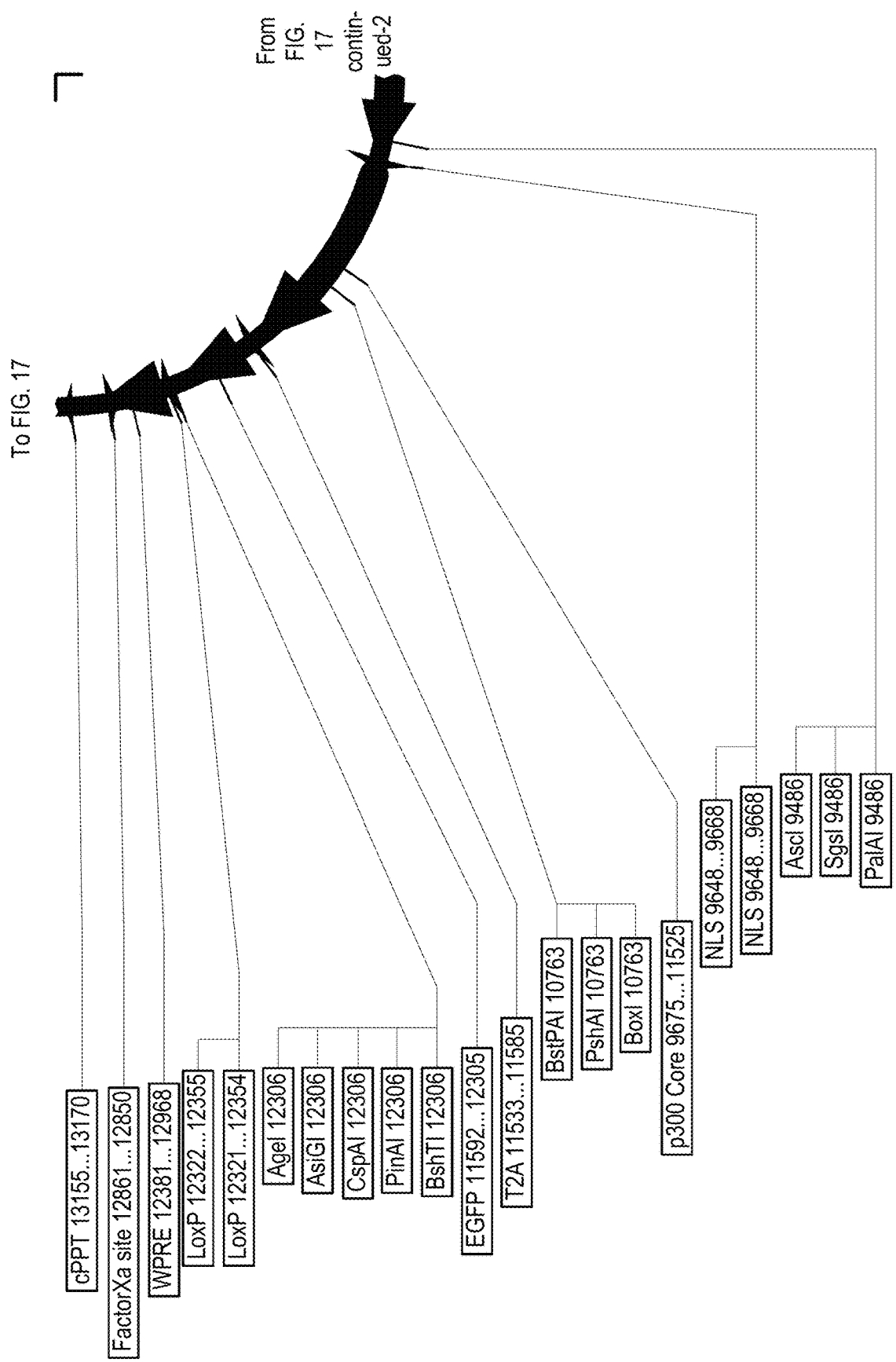

FIG. 17 shows an example of a multiplex upregulation vector. The vector shown comprises dCas9-p300 core.

Figure 18:
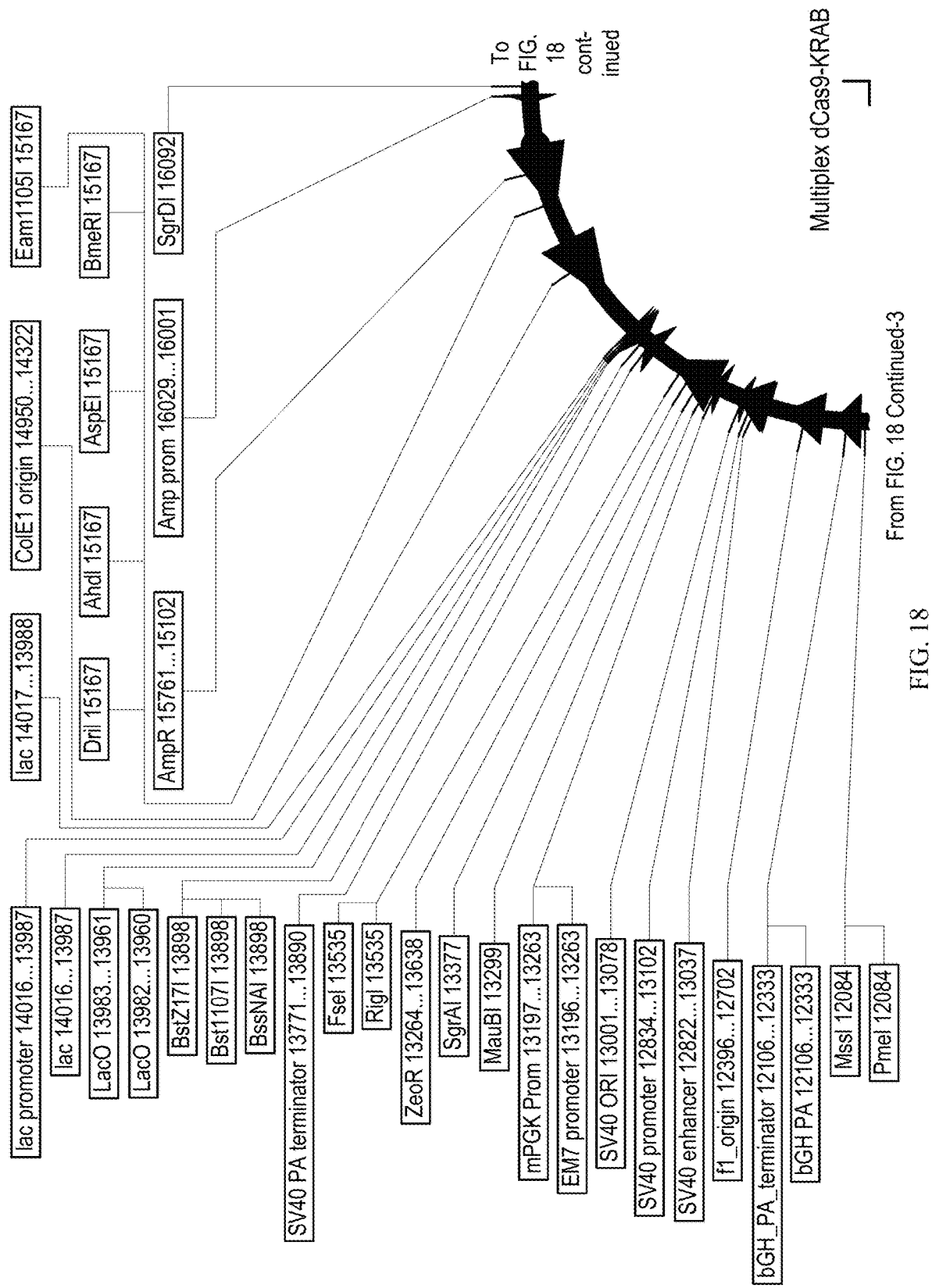
Figure 18:
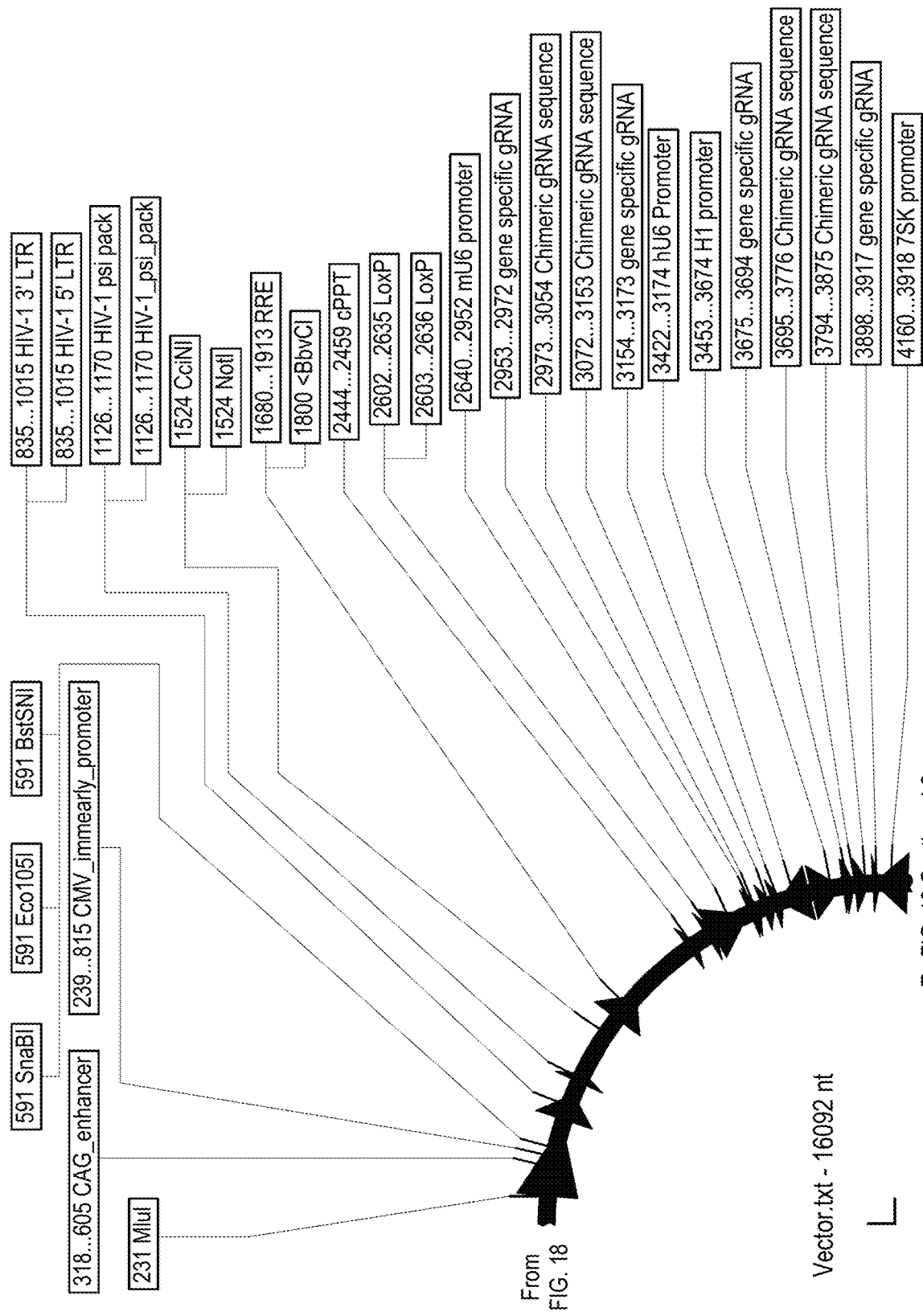
Figure 18:
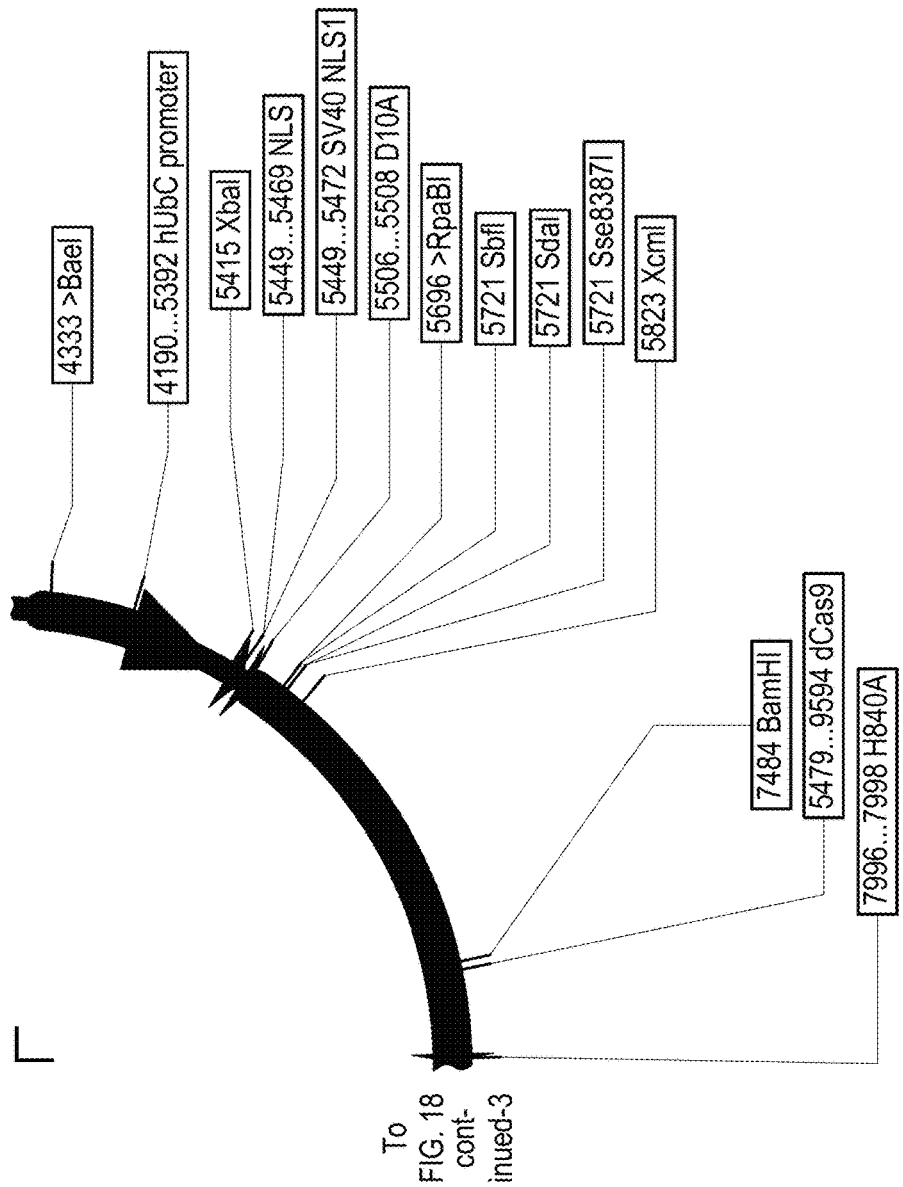
Figure 18:
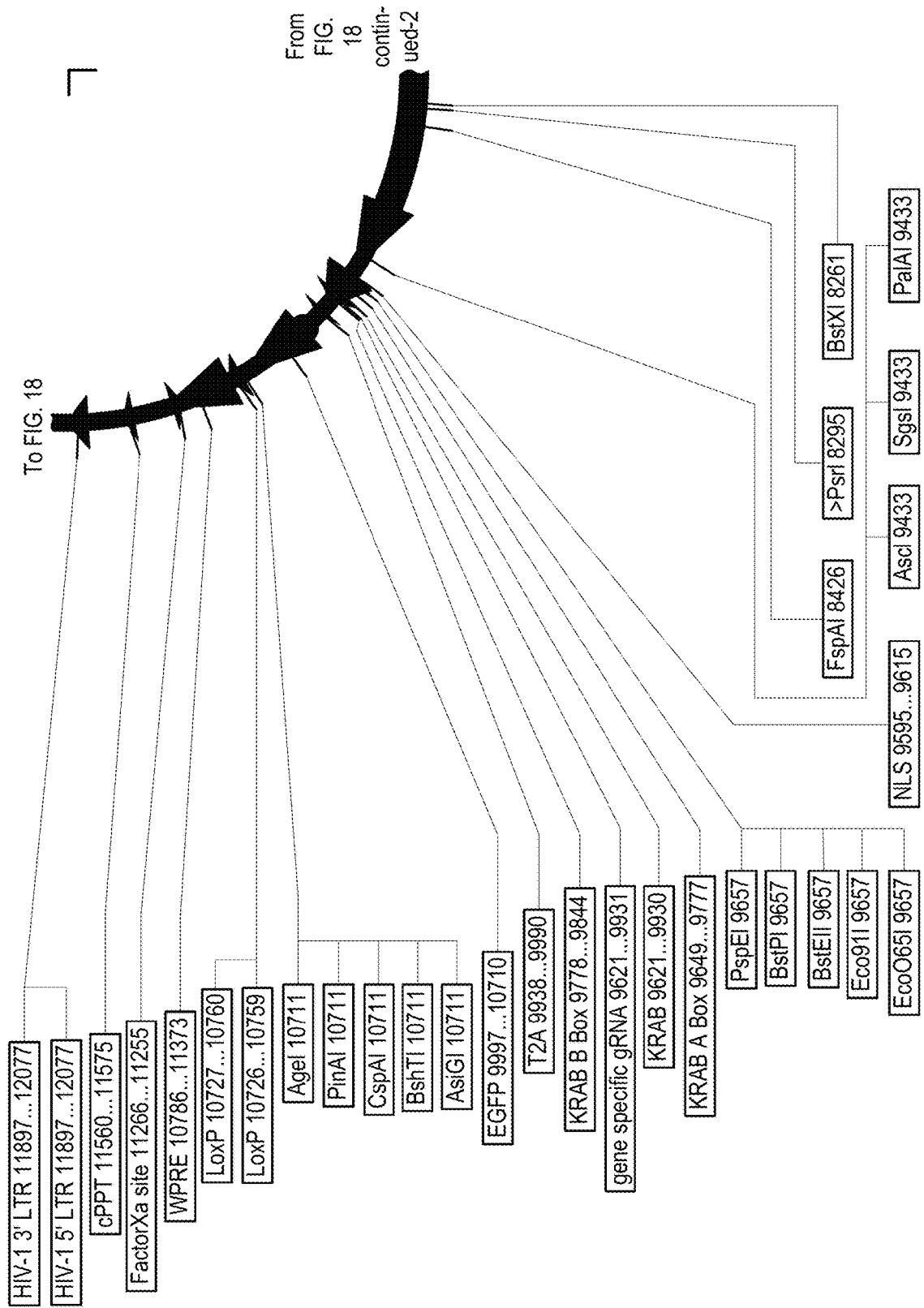

FIG. 18 shows an example of a multiplex upregulation vector. The vector shown comprises dCas9-KRAB.

Figure 19:
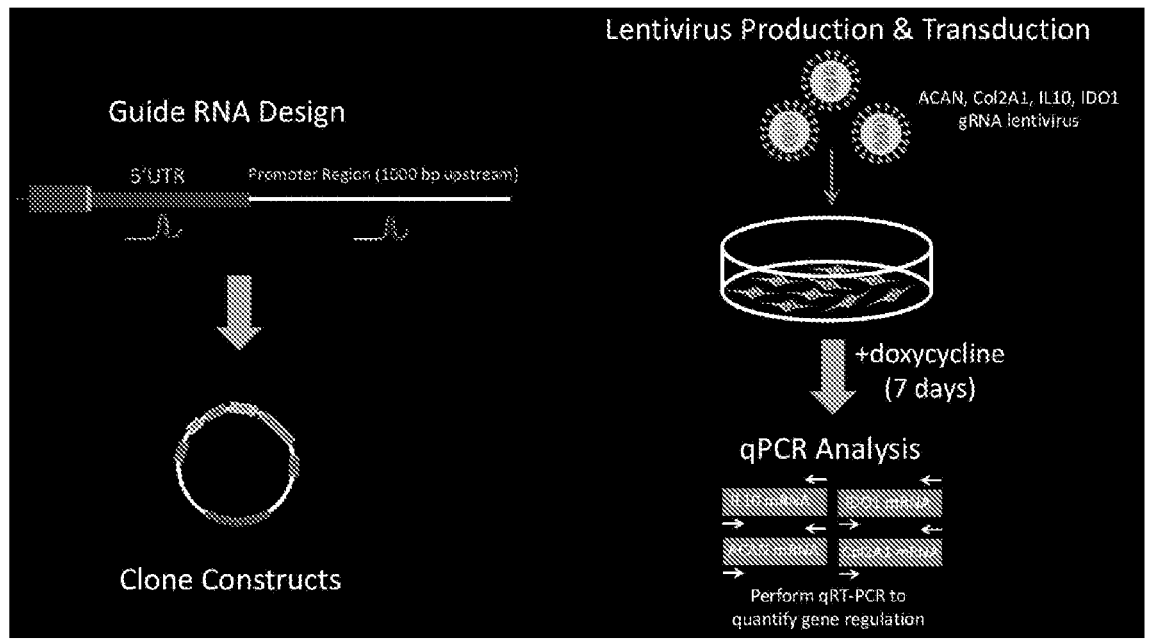

FIG. 19 is a schematic illustration of the application of a sgRNA gene expression screen.

Figure 20:
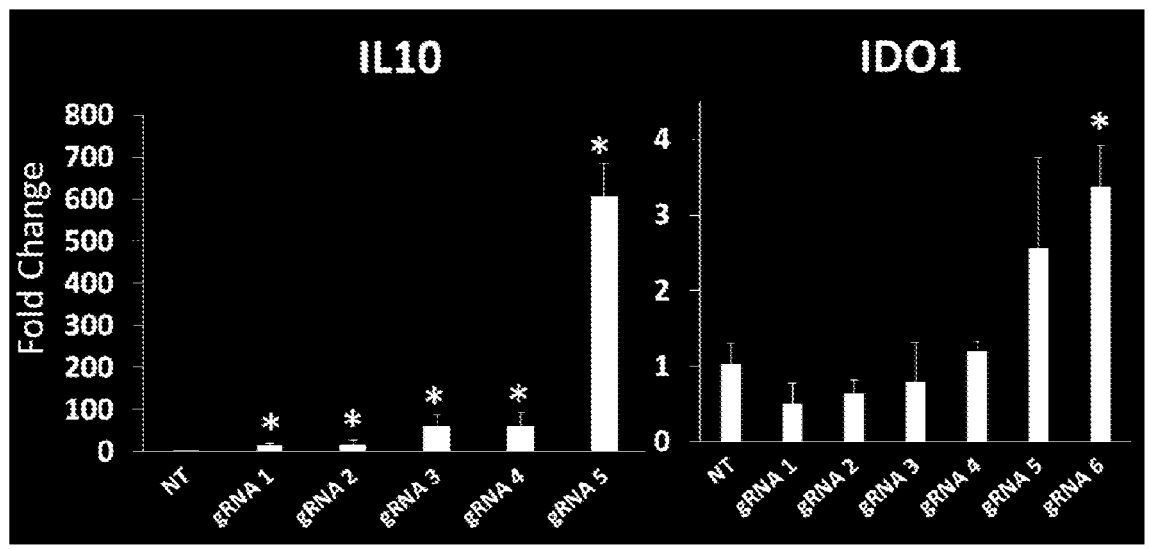

FIG. 20 shows anti-inflammatory gene upregulation for genes IL10 and IDO1 post genome editing (*p<0.5 compared to non-target (NT) control).

Figure 21:
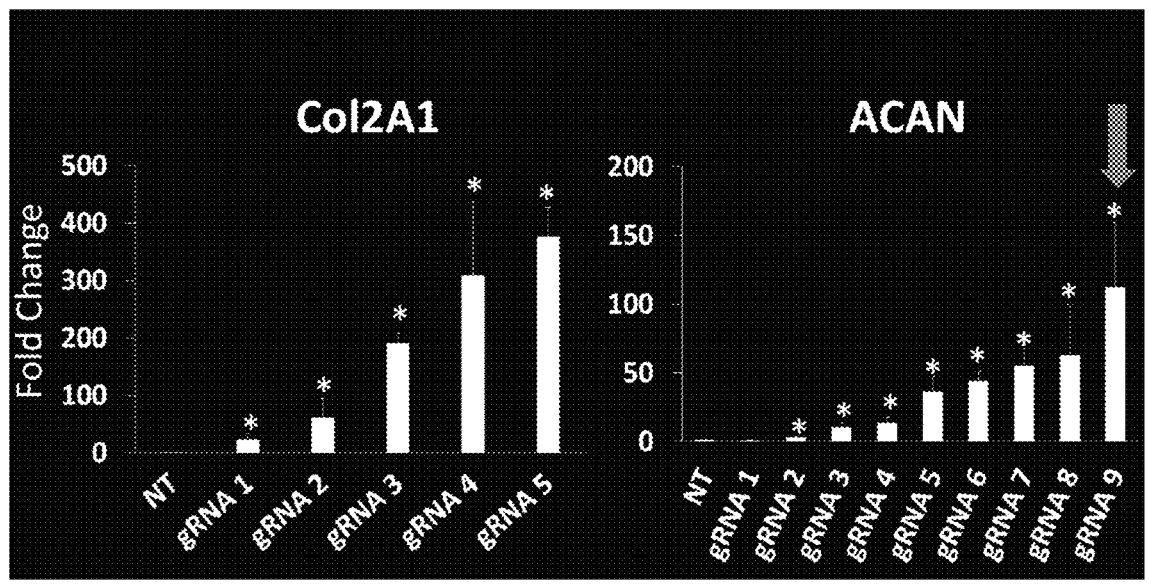

FIG. 21 shows extra-cellular matrix gene upregulation (e.g., Col2A1 and ACAN) post genome editing (*p<0.5 compared to non-target (NT) control).

Figure 22:
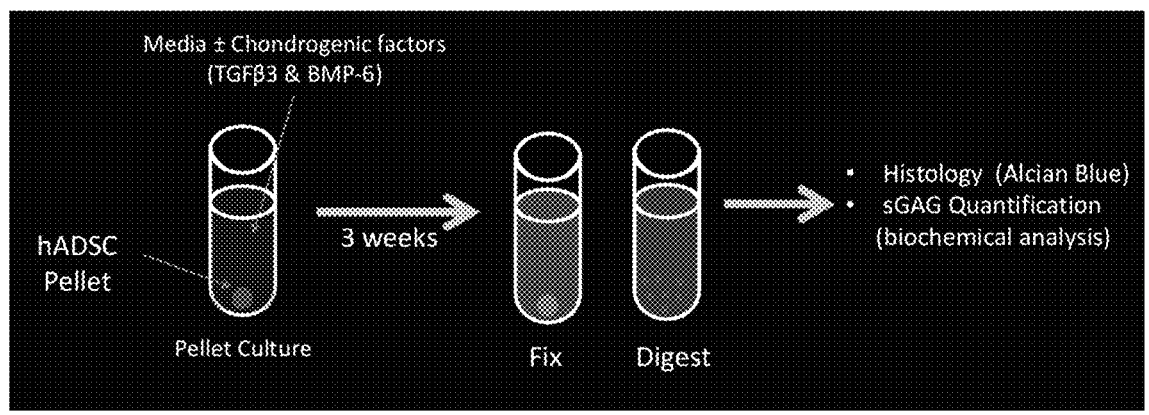

FIG. 22 is a schematic illustration showing chondrogenic differentiation pellet culture.

Figure 23:
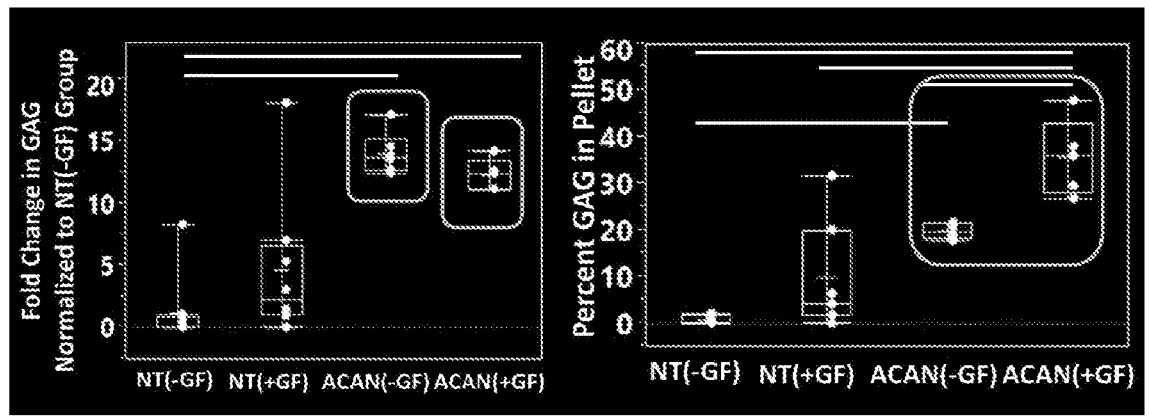

FIG. 23 shows that ACAN edited hASCs demonstrate improved chondrogenesis (bars signify that groups are significantly different (p<0.05).

Figure 24:
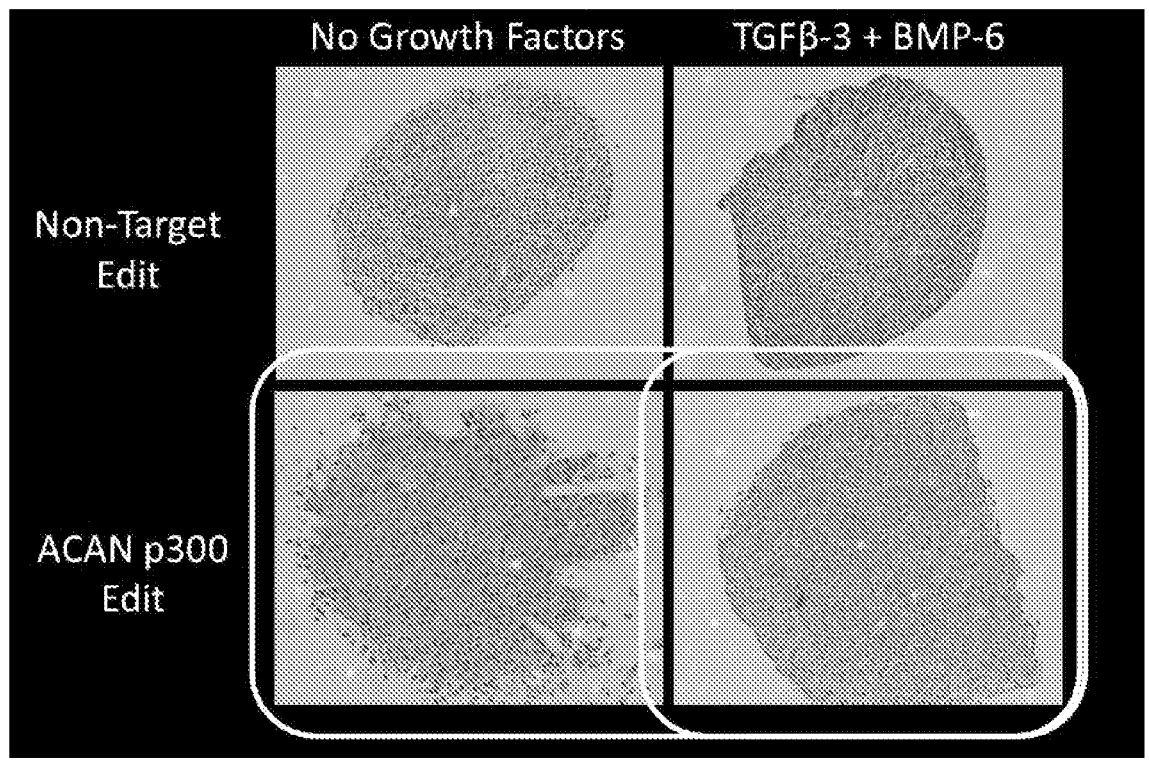

FIG. 24 shows that ACAN editing aids GAG production and results in a chondrogenic phenotype.

Figure 25:
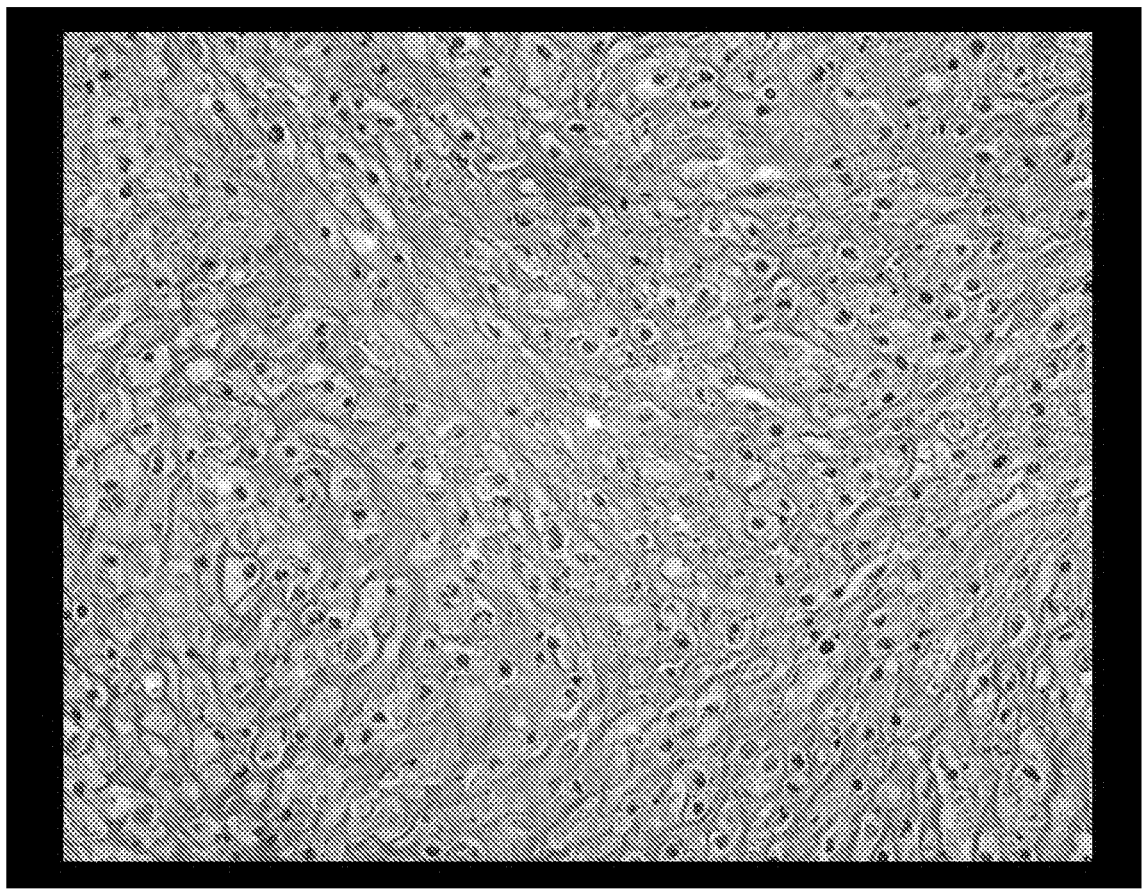

FIG. 25 shows that ACAN editing aids GAG production and generates a chondrogenic phenotype.

Figure 26A:
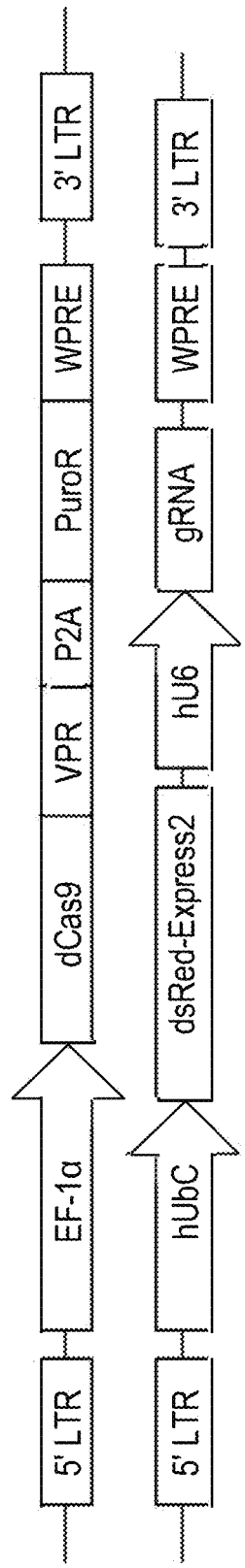

FIGS. 26A-E show the design and verification of CRISPRa vectors. FIG. 26A shows a map of lentiviral vectors for dCas9-VPR expression cassette and gRNA expression cassette. FIG. 26B shows the sequences of each target gene that the gRNAs are designed to target (SEQ ID NOs: 103 and 105 (ACAN) and SEQ ID NOs: 118 and 119 (COL2A1) and their respective PAM sequence. FIG. 26C shows the gene expression changes of ACAN in cells transduced with ACAN targeting gRNAs relative to NTC control cells (n=3, *=p<0.05 relative to NTC group). FIG. 26D shows the gene expression changes of COL2A1 in cells transduced with COL2A1 targeting gRNAs relative to NTC control cells (n=3, *=p<0.05 relative to NTC group). FIG. 26E shows the difference in normalized gene expression of ACAN or COL2A1 in NTC cells or ACAN or COL2A1 upregulated cells relative to COL2A1 cells with gRNA inducing highest gene upregulation (n=3, *=p<0.05 relative to COL2A1 group).

Figures 27A, 27B, 27C:
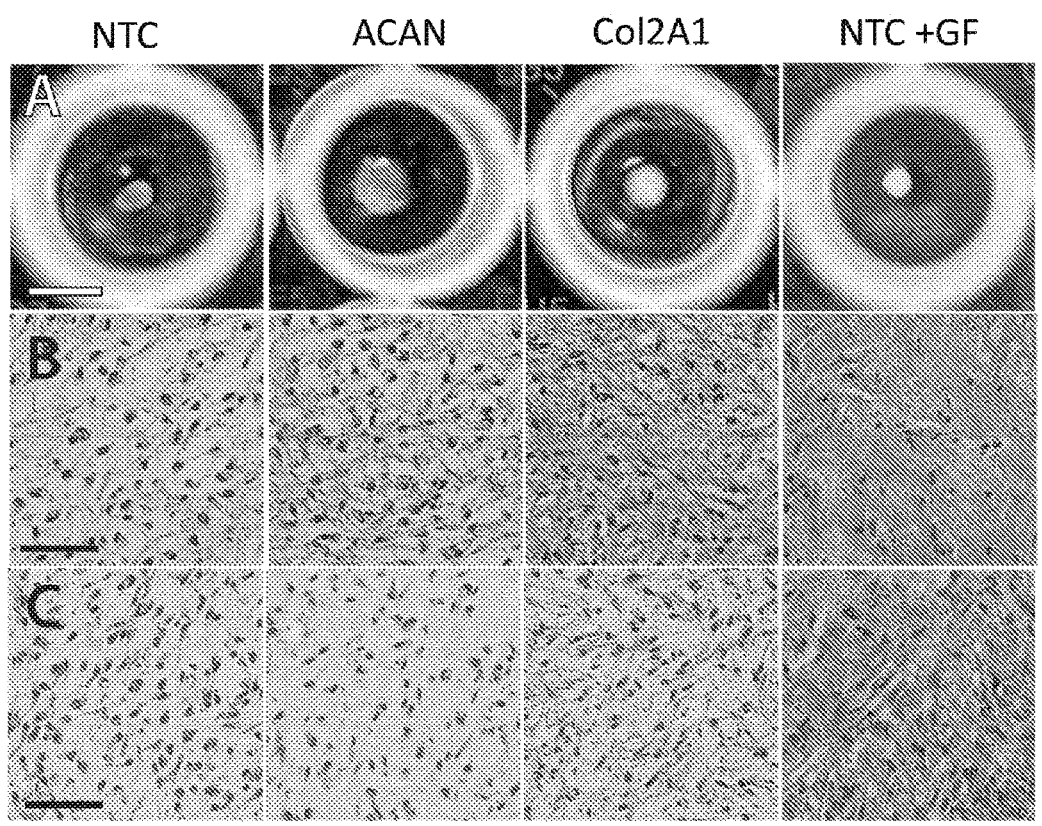

FIGS. 27A-C show qualitative analysis of pellet cultures with singular gene upregulation. FIG. 27A shows macroscopic images of cell pellets demonstrating their morphological similarities and differences (scale bar is 2 mm). FIG. 27B shows alcian blue staining of cell pellets (scale bar is 40 m). FIG. 27C shows collagen II IHC of cell pellets (scale bar is 40 m).

FIGS. 28A-D show biochemical assays quantifying ECM content in pellet cultures: sGAG content within pellets (FIG. 28A) and total sGAG produced by pellets (FIG. 28B) collagen content within pellets (FIG. 28C) and total collagen produced by pellets (FIG. 28D) (n=5-10, *=p<0.05 relative to NTC, dotted line represents amounts produced by NTC+ GF cell pellets).

FIGS. 29A-E shows the results of RNA-seq analysis of cells cultured in pellet culture for 1-week. FIG. 29A is a heat map of differentially expressed genes in cell groups (B & C) FIG. 29B and C show differential gene expression analysis of ACAN (B) or COL2A1 (C) upregulated cells vs NTC cells. FIG. 29D shows the top 5 biological processes associated with genes differentially expressed after COL2A1 upregulation. FIG. 29E shows fold change and significance of gene expression changes in proteoglycans and enzymes associated with proteoglycans and chondroitin sulfate synthesis after COL2A1 upregulation.

FIGS. 30A-D shows the verification of multiplex gene upregulation by CRISPRa vectors. FIG. 30A shows a map of lentiviral vectors for dCas9-VPR expression cassette and gRNA expression cassettes expressed in hADSCs for multiplex gene upregulation. FIG. 30B shows the gene target sequence (SEQ ID NOs: 105 (ACAN) and 119 (COL2A1) of each gRNA and their respective PAM sequence. FIG. 30C shows the gene expression changes of ACAN in cells with multiplex ACAN and COL2A1 upregulation relative to NTC control cells (n=3, *=p<0.05 relative to NTC group). FIG. 30D shows the gene expression changes of COL2A1 in cells with multiplex ACAN and COL2A1 upregulation relative to NTC control cells (n=3, *=p<0.05 relative to NTC group).

FIGS. 31A-C shows the results of a qualitative analysis of pellet cultures. FIG. 31A shows macroscopic images of cell pellets demonstrating their morphological similarities and differences (scale bar is 2 mm). FIG. 31B shows alcian blue staining of cell pellets (scale bar is m). FIG. 31C shows collagen II IHC of cell pellets (scale bar is 40 m).

FIGS. 32A-D shows the results of biochemical assays quantifying ECM content in pellet cultures (FIG. 32A) sGAG content within pellets (FIG. 32A) and total sGAG produced by pellets (FIG. 32B), collagen content within pellets (FIG. 32C) and total collagen produced by pellets (FIG. 32D) (n=5-6, *=p<0.05 relative to NTC, dotted line represents amounts produced by NTC+GF cell pellets).

DETAILED DESCRIPTION

Many modifications and other embodiments of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosures. Further, the dates of publication provided herein can be different from the actual publication dates, which can require independent confirmation.

Definitions

As used in the specification and in the claims, the term "comprising" can include the aspects "consisting of" and "consisting essentially of." "Comprising can also mean "including but not limited to."

As used in the specification and the appended claims, the singular forms "a," "an" and "the" can include plural referents unless the context clearly dictates otherwise. Thus, for example, reference to "a compound" includes mixtures of compounds; reference to "a pharmaceutical carrier" includes mixtures of two or more such carriers, and the like.

The word "or" as used herein means any one member of a particular list and also includes any combination of members of that list.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for back pain, degenerative disc disease, arthritis or musculoskeletal tissue engineering, such as, for example, prior to the administering step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in some aspects, the inhibition or reduction can be a 10, 20, 30, 40, 50, 60, 70, 80, 90, 100%, or any amount of reduction in between as compared to native or control levels. In some aspects, the inhibition or reduction is 10-20, 20-30, 30-40, 40-50, 50-60, 60-70, 70-80, 80-90, or 90-100% as compared to native or control levels. In some aspects, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in some aspects, the increase or promotion can be a 10, 20, 30, 40, 50, 60, 70, 80, 90, 100%, or more, or any amount of promotion in between compared to native or control levels. In some aspects, the increase or promotion is 10-20, 20-30, 30-40, 40-50, 50-60, 60-70, 70-80, 80-90, or 90-100% as compared to native or control levels. In some aspects, the increase or promotion is 0-25, 25-50, 50-75, or 75-100%, or more, such as 200, 300, 500, or 1000% more as compared to native or control levels. In some aspects, the increase or promotion can be greater than 100 percent as compared to native or control levels, such as 100, 150, 200, 250, 300, 350, 400, 450, 500% or more as compared to the native or control levels.

As used herein, the term "determining" can refer to measuring or ascertaining a quantity or an amount or a change in activity. For example, determining the amount of a disclosed polypeptide in a sample as used herein can refer to the steps that the skilled person would take to measure or ascertain some quantifiable value of the polypeptide in the sample. The art is familiar with the ways to measure an amount of the disclosed polypeptides and disclosed nucleotides in a sample.

The phrase "nucleic acid" as used herein refers to a naturally occurring or synthetic oligonucleotide or polynucleotide, whether DNA or RNA or a DNA-RNA hybrid, single-stranded or double-stranded, sense or antisense, which is capable of hybridization to a complementary nucleic acid by Watson-Crick base-pairing. Nucleic acids as disclosed herein can also include nucleotide analogs (e.g., BrdU), and non-phosphodiester internucleoside linkages (e.g., peptide nucleic acid or thiodiester linkages). In particular, nucleic acids can include, without limitation, DNA, RNA, cDNA, gDNA, ssDNA, dsDNA or any combination thereof.

As used herein, the term "complementary" refers to the ability of a nucleic acid to form hydrogen bond(s) with another nucleic acid sequence by either traditional Watson-Crick or other non-traditional types. A percent complementary indicates the percentage of residues in a nucleic acid molecule which can form hydrogen bonds (e.g., Wastson-Crick base pairing) with a second nucleic acid sequence (e.g., 5, 6, 7, 8, 9, 10 out of 10 being 50%, 60%, 70%, 80%, 90%, and 100% complementary).

As used herein, the term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element or regulatory element). The terms "plasmid" and "vector" can be used interchangeably, as a plasmid is a commonly used form of vector. Moreover, this disclosure is intended to include other vectors which serve equivalent functions.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

Low back pain is the leading cause of disability worldwide (Vos T, Barber R M, Bell B, Bertozzi-Villa A, Biryukov S B I et al. Global, regional, and national incidence, prevalence, and years lived with disability for 301 acute and chronic diseases and injuries in 188 countries, 1990-2013: a systematic analysis for the Global Burden of Disease Study 2013. Lancet 2015), ranks third in disease burden according to disease adjusted life years (Murray C J, et al., Lancet 2012; 380:2197-2223), and generates a tremendous socioeconomic cost (Katz J N. J. Bone Joint Surg. Am. 2006; 88 Suppl 2:21-4). Numerous factors have been associated with back pain, including degenerative disc disease, which is characterized by the breakdown of the intervertebral disc (IVD) extracellular matrix (ECM) (Le Maitre C L, Hoyland J A, Freemont A J. Arthritis Res. Ther. 2007; 9:R77; and Roberts S, Evans H, Trivedi J, Menage J. J. bone Jt. Surg. Am. Vol. 2006; 88 Suppl 2:10-14), a loss of disc height (Suthar P, Patel R, Mehta C, Patel N. J. Clin. Diagn. Res. 2015; 9:TC04-9), an inflammatory response (Burke J G, G Watson R W, Conhyea D, McCormack D, Dowling F E, Walsh M G, Fitzpatrick J M. Spine (Phila. Pa. 1976). 2003; 28:2685-93; Burke J G, Watson R W G, McCormack D, Dowling F E, Walsh M G, Fitzpatrick J M. J. bone Jt. Surg. Br. Vol. 2002; 84:196-201; Freemont a J, Watkins a, Le Maitre C, Baird P, Jeziorska M, Knight M T N, Ross E R S, O'Brien J P, Hoyland J a. J. Pathol. 2002; 197:286-92; Kokubo Y, Uchida K, Kobayashi S, Yayama T, Sato R, Nakajima H, Takamura T, Mwaka E, Orwotho N, Bangirana A, Baba H. Laboratory investigation. J. Neurosurg. Spine 2008; 9:285-95; Melrose J, Roberts S, Smith S, Menage J, Ghosh P. Spine (Phila. Pa. 1976). 2002; 27:1278-85; Shamji M F, Setton L A, Jarvis W, So S, Chen J, Jing L, Bullock R, Isaacs R E, Brown C, Richardson W J. Arthritis Rheum. 2010; 62:1974-82; Specchia N, Pagnotta A, Toesca A, Greco F. Eur. Spine J. 2002; 11:145-51; and Vernon-Roberts B, Moore R J, Fraser R D. Spine (Phila. Pa. 1976). 2007; 32:2797-804), and altered innervation of the IVD (Coppes M H, Marani E, Thomeer R T, Oudega M, Groen G J. Lancet (London, England) 1990; 336:189-90; Freemont a J, Watkins a, Le Maitre C, Baird P, Jeziorska M, Knight M T N, Ross E R S, O'Brien J P, Hoyland J a. J. Pathol. 2002; 197:286-92; and Freemont A J, Peacock T E, Goupille P, Hoyland J A, O'Brien J, Jayson M I. Lancet (London, England) 1997; 350:178-81). Despite the observation of these changes in the degenerative IVD and hypotheses on the relationship of these changes to painful symptoms (García-Cosamalón J, del Valle M E, Calavia M G, García-Suárez O, López-Muñiz A, Otero J, Vega J A. J. Anat. 2010; 217:1-15; Kepler C K, Ponnappan R K, Tannoury C a, Risbud M V, Anderson D G. Spine J. 2013; 13:318-30; Lotz J C, Ulrich J a; J. Bone Joint Surg. Am. 2006; 88 Suppl 2:76-82; and Risbud M V, Shapiro I M. Nat. Publ. Gr. 2013:1-13), the underlying mechanisms are not well understood and treatment strategies are limited. Described herein is a model that was developed to demonstrate the underlying sensitizing interactions between the degenerative disc and peripheral neurons and used to demonstrate targeted clustered regularly-interspaced palindromic repeat (CRISPR) epigenome editing to modulate these degenerative IVD induced sensitivities.

In the healthy IVD, neurons innervate the outer lamellae of the IVD and originate in the dorsal root ganglion (DRG). The majority of these neurons are nociceptive neurons expressing calcitonin gene-related peptide (CGRP) (Aoki Y, Ohtori S, Takahashi K, Ino H, Douya H, Ozawa T, Saito T, Moriya H. Spine (Phila. Pa. 1976). 2005; 30:1496-500; Aoki Y, Ohtori S, Takahashi K, Ino H, Takahashi Y, Chiba T, Moriya H. Spine (Phila. Pa. 1976). 2004; 29:1077-81; Ashton I K, Roberts S, Jaffray D C, Polak J M, Eisenstein S M. J. Orthop. Res. 1994; 12:186-92; Kestell G R, Anderson R L, Clarke J N, Haberberger R V, Gibbins I L. J. Comp. Neurol. 2015; and Ohtori S, Takahashi K, Chiba T, Yamagata M, Sameda H, Moriya H. Ann. Anat. 2002; 184:235-40) and TRPV1 (Aoki Y, Ohtori S, Takahashi K, Ino H, Douya H, Ozawa T, Saito T, Moriya H. Spine (Phila. Pa. 1976). 2005; 30:1496-500; Ashton I K, Roberts S, Jaffray D C, Polak J M, Eisenstein S M. J. Orthop. Res. 1994; 12:186-92; Melrose J, Roberts S, Smith S, Menage J, Ghosh P. Spine (Phila. Pa. 1976). 2002; 27:1278-85; and Ohtori S, Takahashi K, Chiba T, Yamagata M, Sameda H, Moriya H. Ann. Anat. 2002; 184:235-40). In degenerative IVDs, the number of nociceptive neurons innervating the disc increases (Johnson W E, Evans H, Menage J, Eisenstein S M, El Haj A, Roberts S. Spine (Phila. Pa. 1976). 2001; 26:2550-7) and nociceptive neurons expressing CGRP (Ashton I K, Roberts S, Jaffray D C, Polak J M, Eisenstein S M. J. Orthop. Res. 1994; 12:186-92; and Brown M F, Hukkanen M V, McCarthy I D, Redfern D R, Batten J J, Crock H V, Hughes S P, Polak J M. J. Bone Joint Surg. Br. 1997; 79:147-53) extend into typically aneural regions of the inner A F and N P (Ashton I K, Roberts S, Jaffray D C, Polak J M, Eisenstein S M. J. Orthop. Res. 1994; 12:186-92; and Brown M F, Hukkanen M V, McCarthy I D, Redfern D R, Batten J J, Crock H V, Hughes S P, Polak J M. J. Bone Joint Surg. Br. 1997; 79:147-53; Coppes M H, Marani E, Thomeer R T, Oudega M, Groen G J. Lancet (London, England) 1990; 336:189-90; Freemont a J, Watkins a, Le Maitre C, Baird P, Jeziorska M, Knight M T N, Ross E R S, O'Brien J P, Hoyland J a. J. Pathol. 2002; 197:286-92; Freemont A J, Peacock T E, Goupille P, Hoyland J A, O'Brien J, Jayson M I. Lancet (London, England) 1997; 350:178-81; and Krock E, Rosenzweig D H, Chabot-Dore A J, Jarzem P, Weber M H, Ouellet J A, Stone L S, Haglund L. J. Cell. Mol. Med. 2014; 18:1213-25). Nociceptive neurons innervating the degenerative IVD are exposed to pathologically high levels of IL-6, TNF-$\alpha$, and IL-1$\beta$ (Burke J G, G Watson R W, Conhyea D, McCormack D, Dowling F E, Walsh M G, Fitzpatrick J M. Spine (Phila. Pa. 1976). 2003; 28:2685-93; Burke J G, Watson R W G, McCormack D, Dowling F E, Walsh M G, Fitzpatrick J M. J. Bone Joint Surg. Br. 2002; 84:196-201; Le Maitre C L, Pockert A, Buttle D J, Freemont A J, Hoyland J A. Soc. Trans. 2007; 35:652-5; Le Maitre C L, Richardson S M A, Baird P, Freemont A J, Hoyland J A. J. Pathol. 2005; 207:445-52; and Shamji M F, Setton L A, Jarvis W, So S, Chen J, Jing L, Bullock R, Isaacs R E, Brown C, Richardson W J. 2010; 62:1974-82) and to pathologically low pH levels (Kitano T, Zerwekh J E, Usui Y, Edwards M L, Flicker P L, Mooney V. Clin. Orthop. Relat. Res. 1993: 372-7). TNF-$\alpha$, IL-1$\beta$, and IL-6 have been demonstrated to sensitize nociceptive neurons to heating (Obreja O, Biasio W, Andratsch M, Lips K S, Rathee P K, Ludwig A, Rose-John S, Kress M. Brain 2005; 128:1634-41; Obreja O, Schmelz M, Poole S, Kress M. Pain 2002; 96:57-62; and Opree A, Kress M. J. Neurosci. 2000; 20:6289-93) and induce thermal hyperalgesia (Andratsch M, Mair N, Constantin C E, Scherbakov N, Benetti C, Quarta S, Vogl C, Sailer C A, Uceyler N, Brockhaus J, Martini R, Sommer C, Zeilhofer H U, Müller W, Kuner R, Davis J B, Rose-John S, Kress M. J. Neurosci. 2009; 29:13473-83; Fang D, Kong L Y, Cai J, Li S, Liu X D, Han J S, Xing G G. Pain 2015:1; Oka Y, Ibuki T, Matsumura K, Namba M, Yamazaki Y, Poole S, Tanaka Y, Kobayashi S. Neuroscience 2007; 145:530-8; and Opree A, Kress M. J. Neurosci. 2000; 20:6289-93) in models of peripheral neuropathy. Additionally, acidic pH (e.g., 6.0-7.0) lowers the temperature threshold of TRPV1 and potentiates signaling through TRPV1 (Caterina M J, Schumacher M A, Tominaga M, Rosen T A, Levine J D, Julius D. Nature 1997; 389:816-24). As a result, the presence of multiple sensitizing factors in the degenerative IVD may trigger discogenic pain by sensitizing TRPV1 to stimuli that are non-painful in healthy patients. Described herein is an in vitro model developed to investigate these interactions and test CRISPR epigenome editing strategies in peripheral neurons to regulate these interactions.

CRISPR epigenome editing allows for stable, site-specific (Thakore P I, Black J B, Hilton I B, Gersbach C A. Nat. Methods 2016; 13:127-137) epigenome modifications to modulate gene expression. Briefly, CRISPR-Cas9-based epigenome editing utilizes a nuclease-deficient Cas9 (dCas9) and a synthetic guide RNA to target specific DNA sequences Cong L, Ran F A, Cox D, Lin S, Barretto R, Habib N, Hsu P D, Wu X, Jiang W, Marraffini L A, Zhang F. Science 2013; 339:819-23; Jinek M, Chylinski K, Fonfara I, Hauer M, Doudna J A, Charpentier E. Science 2012; 337:816-21; and Mali P, Esvelt K M, Church G M. Nat. Methods 2013; 10:957-63). The fusion of KRAB to dCas9 produces targeted H3K9 methylation (Groner A C, Meylan S, Ciuffi A, Zangger N, Ambrosini G, Denervaud N, Bucher P, Trono D. PLoS Genet. 2010; 6:e1000869; Krebs C J, Schultz D C, Robins D M. Mol. Cell. Biol. 2012; 32:3732-42; Reynolds N, Salmon-Divon M, Dvinge H, Hynes-Allen A, Balasooriya G, Leaford D, Behrens A, Bertone P, Hendrich B. EMBO J. 2012; 31:593-605; and Sripathy S P, Stevens J, Schultz D C. Mol. Cell. Biol. 2006; 26:8623-38), which can be used to regulate endogenous gene expression. Disclosed herein are compositions and methods for direct regulation of peripheral neuron sensitization via CRISPR epigenome editing to treat, for example, discogenic back pain symptoms. Using this technique, back pain may be treated by epigenome modifications of pain related genes in nociceptive neurons.

Disclosed herein are models developed to test the hypothesis that degenerative IVD conditions (e.g., inflammatory cytokines and acidic pH) can induce sensitization of nociceptive neurons to noxious stimuli and to demonstrate CRISPR epigenomic editing of nociceptive neurons as a potential discogenic back pain treatment by regulating the peripheral neuron response to these deleterious interactions. This study elucidates the synergistic effects of low pH and the IL-6/AKAP/TRPV1 pathway as responsible for degenerative IVD neuron sensitization and demonstrates epigenomic regulation of this pathway as a pain modulation strategy.

Low back pain (LBP) is a widespread problem, ranking first overall in years lived with disability (Murray and Lopez, 2013), and having an estimated global lifetime prevalence of 38.9% (Hoy et al., 2012). Degenerative disc disease (DDD) is considered a major contributor to LBP (Luoma et al., 2000). Currently both surgical and non-surgical treatments for DDD induced LBP are able to alleviate symptoms but they don't provide a mechanism for preventing the progression of disc degeneration, thus, often LBP may return after treatment (Von Korff and Saunders, 1996). In order to effectively treat DDD induced LBP on a long-term basis, therapeutic methods that can slow DDD progression and reduce the need for surgical intervention are needed. Regarding DDD, its progression has been associated with the action of inflammatory cytokines in the intervertebral disc (IVD) that signal the breakdown of the extracellular matrix (ECM) through their respective receptors (Millward-Sadler et al., 2009; Studer et al., 2011; Purmessur et al., 2013). Therefore a potential method for effectively slowing DDD progression could be to inhibit the catabolic signaling of these inflammatory cytokines in the IVD.

Inhibition of catabolic signaling by inflammatory cytokines may be done by delivering mesenchymal stem cells (MSCs) that are known to have therapeutic immunomodulatory properties (Wang et al., 2014). Delivery of MSCs for treatment of DDD has shown efficacy both pre-clinically and clinically in decreasing pain and/or promoting IVD tissue regeneration (Orozco et al., 2011; Marfia et al., 2014; Pettine et al., 2016; Chun et al., 2012). These therapeutic cells are believed to provide regenerative effects mostly by stimulating anabolic gene expression through paracrine signaling (Strassburg et al., 2010; Tam et al., 2014). This is useful in providing a short term regenerative effect but the long term effects of this mechanism of action are unclear. In some aspects, in order to provide long term effects delivered MSCs must remain viable in the IVD. This likely requires them to differentiate into nucleus pulposus (NP) or chondrocyte like cells in order to withstand the low pH, high osmolarity environment of the IVD (Wuertz et al., 2008; Liang et al., 2012). With increased levels of inflammatory cytokines TNF-α and IL-1β known to be in the degenerative IVD (Le Maitre et al., 2007; Weiler et al., 2005) differentiation may be inhibited (Wehling et al., 2009; Heldens et al., 2012). Therefore to promote survival and regeneration by implanted MSCs in the IVD, it may be beneficial to regulate signaling of TNF-α and IL-1β in MSCs to be delivered to the degenerative IVD.

To regulate signaling of TNF-α and IL-1β, binding to their respective receptors must be inhibited. This may be achieved through cytokine specific inhibitors delivered directly or by gene therapy, but use of inhibitors has drawbacks. Regarding direct delivery, continuous delivery is needed for long-term inhibition due to the short half-life of the inhibitor molecules. Regarding both types of delivery, the inhibitors aren't cell or receptor specific, thus, they may inhibit any pathway that TNF-α and IL-1β signals, on any cell presenting the appropriate receptors within their vicinity. A more controllable method for inhibition of signaling is regulating the presence of the particular receptors as signal transducing receptors act upon the cells they are presented on and regulate specific pathways. Being able to regulate specific pathways is important as not all functions of these inflammatory cytokines are negative. For example, concerning TNF-α receptor signaling through TNFR1 can result in either apoptotic or anti-apoptotic signaling but signaling through TNFR2 is known to result in anti-apoptotic pathways, thus, it is of interest to specifically target TNFR1 signaling (Cabal-Hierro and Lazo, 2012).

To decrease the presence of specific inflammatory cytokine receptors, one must regulate their protein or gene expression for which there are several methods available. A recently developed method of gene regulation at the genomic level, Clustered Regularly Interspaced Short Palindromic Repeats (CRISPR) based epigenome editing (Thakore et al., 2015; Larson et al., 2013), is of interest for regulating receptor expression and therefore signaling of inflammatory cytokines. It has been shown to perform highly specific and effective gene modulation in mammalian cells and has been shown to be more robust in downregulating expression compared to RNAi (Gilbert et al., 2014). A study described herein aimed to investigate the functional effects of regulating expression of TNFR1 and IL1R1, via CRISPR based epigenome editing. This was first screened in HEK293T cells to allow for rapid design, and then more thoroughly investigated in immortalized human adipose derived mesenchymal stem cells (hADMSCs). These hADMSCs were used as they provide an in vitro model for a clinically relevant cell population regarding cell delivery to the degenerative IVD. It was hypothesized that downregulation of TNFR1 and IL1R1 by epigenome editing will inhibit inflammatory signaling that results in ECM degradation, cell apoptosis, and inhibition of differentiation therefore engineering cells that are more likely to have a regenerative effect within the environment of the degenerative IVD once implanted.

The newly developed tool for endogenous gene regulation, CRISPR interference (CRISPRi), has the potential to provide effective multiplex gene regulation for applications in DDD. It has been shown that CRISPRi can perform specific and effective gene knockdown in mammalian cells in a single or multiplex manner (Larson M H, Gilbert L A, Wang X, Lim W A, Weissman J S, Qi L S. 2013, *Nat Protoc*, 8: 2180-96. As described herein, this system requires the expression of nuclease-inactive Cas9 (dCas9) by itself or fused to the Kruppel-associated box (KRAB) and the expression of short genomic loci-specific guide RNAs (gRNAs) that are complementary to the promoter of the gene. As further disclosed herein, the CRISPRi system can be used to perform multiplex knockdown of inflammatory cytokine receptors and inhibit actions of inflammatory cytokines on cells in the IVD and retard the progression of DDD. Herein, the modulation of TNFR1 and IL1R1 using CRISPRi in both HEK293T cells and human nucleus pulpous cells and the ability to alter cell response to inflammatory challenge is demonstrated.

Described herein are compositions and methods directed to CRISPRi regulation of inflammation in the intervertebral disc and nervous system for the treatment of back pain related pathologies. The compositions described herein can be delivered directly to one or more intervertebral discs, for example, after a discectomy procedure to halt the progression of disc degeneration after surgery; delivered to adjacent intervertebral discs, for example, after spinal fusion surgery to halt the progression of disc degeneration (e.g., adjacent segment disease) after surgery; delivered to one or more peripheral nerves to, for example, antagonize sensitization of nociceptive neurons due to inflammatory signaling for the treatment of neuropathies, including but not limited to radiculopathy and discogenic back pain; and delivered to the central nervous system, for example, to antagonize altered neuronal signaling due to inflammatory signaling for the treatment of neuropathies, including but not limited to radiculopathy and discogenic back pain.

Using stem cell technologies in musculoskeletal tissue engineering and cell therapies has been of great interest. However, the success of these strategies is limited, as stem cells implanted into challenging disease environments struggle to maintain an optimal phenotype. Regulating the phenotype of stem cells has largely been accomplished by controlled growth factor treatment/Disclosed herein are methods for controlling cell phenotype without using or relying on growth factors by utilizing targeted CRISPR gene activators. These CRISPR-Cas systems or CRISPR complexes can be used to carry out specific gene upregulation at regulatory elements via a guide RNA (gRNA)/dCas9-activator complex. Using this system, multiple genes at once (two or more) can be regulated to produced a desired cell phenotypes without using or relying on growth factors. For instance, disclosed herein are CRISPR-Cas systems or CRISPR complexes that can be used to modify one or more cellular properties or induce or activate one or more cellular properties (e.g., increase the regenerative potential of one or more cells; and/or increase anti-flammatory actions) Disclosed herein are CRISPR-Cas systems or CRISPR complexes that can be used to upregulate aggrecan (ACAN), type II collagen (COL2A1), interleukin 10 (IL-10), and/or indoleamine 2,3-dioxygenase 1 (IDO1) to engineer stem cells with enhanced musculoskeletal tissue regenerative/anti-inflammatory properties that allow them to better treat or improve the treatment or management of degenerative disc disease. Also, disclosed herein is the application of CRISPR-Cas systems or CRISPR complexes to cell therapies in the disc or as direct gene therapies to treat backpain.

Advantages of the disclosed CRISPR-Cas systems or CRISPR complexes include but are not limited to: 1) the disclosed CRISPR-Cas systems or CRISPR complexes can be used to control cell phenotype without the need for or use of growth factors, thus, eliminating complicated differentiation strategies associated with cell therapy; 2) the delivered cells with the improved cellular properties (e.g., increased regenerative potential and/or anti-inflammation) due to the upregulation of one or more genes (e.g., ACAN, Col2A1, IL-10 and IDO1) can remain active after in vivo delivery, allowing better cell therapeutic control after cells have been delivered; 3) the upregulation or activation of one or more genes (e.g., ACAN, Col2A1, IL-10 and IDO1) can enhance the cell phenotype compared to growth factor stimulation by producing higher levels of extracellular matrix and/or inflammatory modulating molecules; and/or 4) the upregulation or activation of one or more genes (e.g., ACAN, Col2A1, IL-10 and IDO1) can introduce function to the cells that they would not endogenously have by activating certain genes that are not endogenously active in the cells.

As a result, cells with improved function (e.g., regenerative ability and anti-inflammatory actions) can be produced to treat back pain either through cell engineering or gene therapy.

The practical application of this disclosure is the production of engineered stem cells that can be delivered to the degenerative IVD to produce an inflammatory and regenerative outcome that treats or reduces back pain. Further, vectors can also be directly delivered to the IVD as a gene therapy to treat or reduce back pain.

Compositions

The compositions disclosed herein include a CRISPR-Cas system. The CRISPR-Cas system can be non-naturally occurring. In some aspects, the CRISPR-Cas system comprises one or more vectors. In some aspects, the vectors can be singleplex or multiplex vectors. For example, vectors that can be used in the disclosed compositions and methods can include, but are not limited to the vectors shown in FIGS. 15-18, 26 and 30. In some aspects, a singleplex vector can be a repression vector. In some aspects, a singleplex vector can be an upregulation vector. In some aspects, a multiplex vector can be a repression vector. In some aspects, a multiplex vector can be an upregulation vector. In some aspects, the vector can be a combination repression, upregulation vector.

In some aspects, the one or more vectors comprise a promoter operably linked to one or more nucleotide sequences encoding a CRISPR-Cas system guide RNA (gRNA). In some aspects, the gRNA can hybridize with a target sequence of a DNA molecule or locus in a cell. In some aspects, the one or more vectors can also comprise a regulatory element operably linked to a nucleotide sequence encoding a RNA-directed nuclease. In some aspects, the promoter operably linked to one or more nucleotide sequences encoding a CRISPR-Cas system gRNA and the regulatory element operably linked to a nucleotide sequence encoding a RNA-directed nuclease can be located on the same or different vectors of the same system. The gRNA can target and hybridize with the target sequence. In some aspects, the gRNA can also direct the RNA-directed nuclease into the DNA molecule or locus. In some aspects, the gRNA sequence can be selected from the group listed in Table 6. In some aspects, the gRNA sequence can be selected from the group listed in Table 6 in combination with one or more gRNA sequences from the group listed in Tables 2 and 4.

As used herein, the term "regulatory element" refers to promoters, promoter enhancers, internal ribosomal entry sites (IRES) and other elements that are capable of controlling expression (e.g., transcription termination signals, including but not limited to polyadenylation signals and poly-U sequences). Regulatory elements can direct constitutive expression. Regulatory elements can be tissue-specific. Examples of tissue-specific promoters can direct expression in a desired tissue of interest (e.g., muscle, neuron, bone, skin, blood, intervertebral disc), specific organs (e.g., liver, pancreas, brain, spinal cord), or particular cell types (peripheral nerves, annulus fibrosus, nucleus pulposus, chondrocytes). Regulatory elements can also direct expression in a temporal-dependent manner including but not limited to cell-cycle dependent or developmental stage-dependent. Temporal-dependent expression can be tissue or cell-type specific. Regulatory element can also refer to enhancer elements. Examples of enhancer elements include but are not limited to WPRE, CMV enhancers, and SV40 enhancers. In some aspects, the regulatory element is hUbC. In some aspects, the hUbC promoter is operably linked to a nucleotide sequence encoding a RNA-directed nuclease. Generally, any constitutive promoter can be operably linked to a nucleotide sequence encoding a RNA-directed nuclease. Specific gene specific promoters can be used. Such promoters allow cell specific expression or expression tied to specific pathways. Any promoter that is active in mammalian cells can be used. In some aspects, the promoter is an inducible promoter including, but not limited to, Tet-on and Tet-off systems. Such inducible promoters can be used to control the timing of the desired expression.

The transcriptional control element can be a promoter. In some aspects, the promoter can be a mammalian cell active promoter (e.g., SV40, CMV, SP6, T7); a yeast active promoter (e.g., GAL4); a bacteria active promoter (e.g., Lac); or a baculovirus/insect cell active promoter (e.g., polyhedron). In some aspects, the transcriptional control element can be an inducible promoter. Examples of inducible promoters include but are not limited to tetracycline inducible system (tet); heat shock promoters and IPTG activated promoters.

Disclosed herein, are vectors comprising a promoter operably linked to one or more nucleotide sequences encoding a CRISPR-Cas system gRNA and a regulatory element operably linked to a nucleotide sequence encoding a RNA-directed nuclease. In some aspects, the gRNA sequence can be selected from the group listed in Table 6. In some aspects, the gRNA sequence can be selected from the group listed in Table 6 in combination with one or more gRNA sequences from the group listed in Tables 2 and 4. In some aspects, the one or more vectors can further comprise one or more gRNA sequences that can be selected from the group listed in Table 6. In some aspects, the gRNA sequence can be selected from the group listed in Table 6 in combination with one or more gRNA sequences from the group listed in Tables 2 and 4. In some aspects, the promoter operably linked to one or more nucleotide sequences encoding a CRISPR-Cas system gRNA and a regulatory element operably linked to a nucleotide sequence encoding a RNA-directed nuclease can be on the same or different vectors of the same system.

Vectors include, but are not limited to nucleic acid molecules that are single-stranded double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a viral vector, wherein virally-derived DNA or RNA sequences are present in the vector for packaging into a virus. Viral vectors can include polynucleotides carried by a virus for transfection into a host cell. In some aspects, the CRISPR-Cas system described herein is packaged into a single lentiviral, adenoviral or adeno-associated virus particle.

The vectors disclosed herein can also include detectable labels. Such detectable labels can include a tag sequence designed for detection (e.g., purification or localization) of an expressed polypeptide. Tag sequences include, for example, green fluorescent protein, glutathione S-transferase, polyhistidine, c-myc, hemagglutinin, or Flag™ tag, and can be fused with the encoded nucleic acid.

Some vectors are capable of autonomous replication in a host cell which they are introduced (e.g., bacterial vectors having a bacterial origin of replication and episomal mammalian vectors). Other vectors (e.g., non-episomal mammalian vectors) are integrated into the genome of a host cell upon introduction into the host cell, and are thereby replicated along with the host genome.

The term "expression vector" is herein to refer to vectors that are capable of directing the expression of genes to which they are operatively-linked. Common expression vectors of utility in recombinant DNA techniques are often in the form of plasmids. Recombinant expression vectors can comprise a nucleic acid as disclosed herein in a form suitable for expression of the acid in a host cell. In other words, the recombinant expression vectors can include one or more regulatory elements or promoters, which can be selected based on the host cells used for expression that is operatively linked to the nucleic acid sequence to be expressed.

The term "operatively linked to" refers to the functional relationship of a nucleic acid with another nucleic acid sequence. Promoters, enhancers, transcriptional and translational stop sites, regulatory elements, regulatory control elements and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

One or more vectors can be introduced into a cell (e.g., a host cell) to produce transcripts, proteins, peptides including fusion proteins and peptides, encoded by nucleic acids as described herein (e.g., clustered regularly interspersed short palindromic repeats (CRISPR) transcripts, proteins, enzymes, mutant forms thereof, fusion proteins thereof, etc.). In some aspects, the vector is a viral vector. Examples of vectors include, but are not limited to lentiviruses, adenoviral, and adeno-associated viruses. The type of vector can also be selected for targeting a specific cell type.

The vectors disclosed herein can comprise one or more promoters or regulatory elements or the like. In some aspects, a vector comprises one or more pol promoters, one or more pol promoters II, one or more poll III promoters, or combinations thereof. Examples of pol II promoters include, but are not limited to the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phospho glycerol kinase (PGK) promoter, and the EF1α promoter. In some aspects, pol II promoters can be engineered to confer tissue specific and inducible regulation of gRNAs. Examples of pol III promoters include, but are not limited to, U6 and H1 promoters. In some aspects, the promoter is U6. In some aspects, the promoter operably linked to the gRNA is a Pol III promoter, human u6, mouse U6, H1, or 7SK.

In some aspects, the compositions described herein (e.g., CRISPR-Cas systems, vectors) can comprise one or more promoters or regulatory elements. In the instance of two or more promoters or regulatory elements, said promoters or regulatory elements can be referred to as a first promoter, a second promoter and so on.

The vector or vector systems disclosed herein can comprise one or more vectors. Vectors can be designed for expression of CRISPR transcripts (e.g., nucleic acid transcripts, proteins, or enzymes) in prokaryotic or eukaryotic cells. CRISPR transcripts, for example, can be expressed in bacterial cells (e.g., *Escherichia coli*), insect cells (using baculovirus expression vectors), yeast cells, or mammalian cells. Alternatively, the recombinant expression vector can be transcribed and translated in vitro, for example, using T7 promoter regulatory sequences and T7 polymerase.

Generating constructs for the CRISPR/Cas9 system described herein can be a singleplex or multiplexed. The targets of the CRISPR/Cas9 system described herein can be multiplexed. In some aspects, the vectors can be singleplex vector or multiplex vectors. In some aspects, the singleplex or multiplex vectors can be repression or downregulation vectors or upregulation vectors or a combination thereof.

Vectors can be introduced in a prokaryote, amplified and then the amplified vector can be introduced into a eukaryotic cell. The vector can also be introduced in a prokaryote, amplified and serve as an intermediate vector to produce a vector that can be introduced into a eukaryotic cell (e.g., amplifying a plasmid as part of a viral vector packaging system). A prokaryote can be used to amplify copies of a vector and express one or more nucleic acids to provide a source of one or more proteins for delivery to a host cell or host organism. Expression of proteins in prokaryotes is often carried out in *Escherichia coli* with vectors containing constitutive or inducible promoters directing the expression of either fusion or non-fusion proteins. Vectors can also be a yeast expression vector (e.g., *Saccharomyces cerevisiae*).

In some aspects, the vector is capable of driving expression of one or more sequences in mammalian cells using a mammalian expression vector. Examples of mammalian expression vectors include but are not limited to pCDM8 and pMT2PC. In mammalian cells, regulatory elements control the expression of the vector. Examples of promoters are those derived from polyoma, adenovirus 2, cytomegalovirus, simian virus 40, and others disclosed herein and known in the art.

In some aspects, the regulatory element is operably linked to one or more elements of a CRISPR system to drive expression of the one or more elements of the CRISPR system. CRISPRs are a family of DNA loci that are generally specific to a particular species (e.g., bacterial species). The CRISPR locus comprises a distinct class of interspersed short sequence repeats (SSRs) that were identified in *E. coli*, and associated genes. The repeats can be short and occur in clusters that are regularly spaced by unique intervening sequences with a constant length.

As used herein, "CRISPR system" and "CRISPR-Cas system" refers to transcripts and other elements involved in the expression of or directing the activity of CRISPR-associated ("Cas") genes, including sequences encoding a Cas gene, a guide sequence (also referred to as a "spacer" in the context of an endogenous CRISPR system; e.g. guide RNA or gRNA), or other sequences and transcripts from a CRISPR locus. In some aspects, one or more elements of a CRISPR system is derived from a type I, type II, or type III CRISPR system. In some aspects, one or more elements of a CRISPR system are derived from a particular organism comprising an endogenous CRISPR system, such as *Streptococcus pyogenes*. Generally, a CRISPR system is characterized by elements that promote the formation of a CRISPR complex at the site of a target sequence (also referred to as a proto spacer in the context of an endogenous CRISPR system).

As used herein, the term "target sequence" refers to a sequence to which a guide sequence (e.g. gRNA) is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence can comprise any polynucleotide, such as DNA or RNA polynucleotides. In some aspects, a target sequence can be located in the nucleus or cytoplasm of a cell. In some aspects, the target sequence can be within an organelle of a eukaryotic cell (e.g., mitochondrion). A sequence or template that can be used for recombination into the targeted locus comprising the target sequences is referred to as an "editing template" or "editing polynucleotide" or "editing sequence." Disclosed herein are target sequences. In some aspects, the target sequence(s) can be is selected from one or more of the sequences listed in Table 5. In some aspects, the target sequence(s) can be is selected from one or more of the sequences listed in Table 5 in combination with one or more of the sequences listed in Table 1 and Table 3.

A guide sequence (e.g. gRNA) can be any polynucleotide sequence having sufficient complementarity with a target polynucleotide sequence to hybridize with the target sequence and direct sequence-specific binding of a CRISPR-Cas system or CRISPR complex to the target sequence. In some aspects, the degree of complementarity between a guide sequence (e.g. gRNA) and its corresponding target sequence is about or more than about 50%, 60%, 70%, 75%, 80%, 85%, 90%, 95%, 99%, or more. In some aspects, a guide sequence is about more than about 5, 10, 15, 20, 25, 30, 35, 40, 45, 50 or more nucleotides in length or any number in between.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). It is believed that the target sequence should be associated with a PAM (protospacer adjacent motif); that is, a short sequence recognized the CRISPR complex. The precise sequence and length requirements for the PAM differ depending on the CRISPR enzyme used, but PAMs are typically 2-5 base pair sequences adjacent the protospacer (that is, the target sequence). A skilled person will be able to identify further PAM sequences for use with a given CRISPR enzyme. In some aspects, the PAM comprises NGG (where N is any nucleotide, (G)uanine, (G)uanine). In some aspects, the PAM sequence can be GGG or AGG. The target sequence corresponds to one or more receptors. In some aspects, the target sequence can a tumor necrosis factor receptor (e.g., TNFR2), interleukin 1 receptor (e.g., IL1R2, IL6R), A-kinase anchor protein 5 (e.g., AKAP5), a glycoprotein (e.g., gp130) and transient receptor potential cation channel subfamily V member 1 (TRPV1). In some aspects, the target sequence can be aggrecan (ACAN), type II collagen (Col2A1), interleukin 10 (IL-10) and indoleamine 2,3-dioxygenase 1 (IDO1). In some aspects, the target sequence can be selected from one or more of the sequences listed in Table 5. In some aspects, the target sequence can be selected from one or more of the sequences listed in Table 5 in combination with one or more of the sequences listed in Tables 1 and 3.

Disclosed herein, are gRNA sequences. The disclosed gRNA sequences can be specific for one or more desired target sequences. In some aspects, the gRNA sequence hybridizes with a target sequence of a DNA molecule or locus in a cell. In some aspects, the gRNA sequence hybridizes to one or more target or targets sequences corresponding to including but not limited to dorsal root ganglion (e.g., peripherical cells), nociceptive neurons (CGRP+(heat sensor); substance P; TRPV1, AKAP 79, AKAP 150 and nerve growth factor (NGF)). In some aspects, the gRNA sequence hybridizes to one or more target or targets sequences corresponding to including but not limited to aggrecan (ACAN), collagen type II alpha 1 chain (Col2A1), interleukin 10 (IL10) and indoleamine 2,3-dioxygenase 1 (IDO1). In some aspects, the cell can be a eukaryotic cell. In some aspects, the target sequences can be selected from one or more of the sequences listed in Table 5. In some aspects, the target sequences can be selected from one or more of the sequences listed in Table 5 in combination with one or more of the sequences listed in Table 1 and Table 3. In some aspects, the cell can be a mammalian or human cell. In some aspects, the cell can be a mesenchymal stem cell. In some aspects, the cell can be an annulus fibrosus cell or nucleus pulposus cell. In some aspects, the cell can be a human adipose-derived stem cell. In some aspects, the cell can be a cadaver harvested cell. In some aspects, the cell can be a mesoblast cell. In some aspects, the cell can be a derived from bone marrow. In some aspects, the cell can be any cell that can be delivered therapeutically to the disc, including but not limited to stem cells, or primary cells, such annulus fibrosus (AF) cells, nucleus pulposus (NP) cells, chondrocytes, or fibroblasts. For direct gene therapy and delivery to the disc, the cell type can be any cell type in the IVD, including but not limited to AF and NP cells, as well as the chondrocytes in the endplate; and invading immune cells in the disc, including macrophages, T-cells, neutrophils. In some aspects, gRNA sequences target one or more cell type in the IVD.

In some aspects, the gRNA targets and hybridizes with the target sequence and directs the RNA-directed nuclease to the DNA locus. In some aspects, the CRISPR-Cas system and vectors disclosed herein comprise one or more gRNA sequences. In some aspects, the gRNA sequences are listed in Table 6. In some aspects, the gRNA sequences are listed in Table 6 and can be combined with one or more of the gRNA sequences listed in Table 2 and Table 4. In some aspects, the target sequences can be selected from one or more of the sequences listed in Table 5. In some aspects, the target sequences can be selected from one or more of the sequences listed in Table 5 in combination with one or more of the sequences listed in Table 1 and Table 3. In some aspects, the CRISPR-Cas system and vectors disclosed herein comprise 2, 3, 4 or more gRNA sequences. In some aspects, the CRISPR-Cas system and/or vector described herein comprises 4 gRNA sequences in a single system. In some aspects, the gRNA sequences disclosed herein can be used turn one or more genes on (p300 core, tripartite activator, VP64-p65-Rta (VPR)) or off (KRAB).

The compositions described herein can include a nucleic acid encoding a RNA-directed nuclease. The RNA-directed nuclease can be a CRISPR-associated endonuclease. In some aspects, the RNA-directed nuclease is a Cas9 nuclease or protein. In some aspects, the Cas9 nuclease or protein can have a sequence identical to the wild-type *Streptococcus pyrogenes* sequence. In some aspects, the Cas9 nuclease or protein can be a sequence for other species including, for example, other *Streptococcus* species, such as *thermophilus*; *Pseudomonas aeruginosa, Escherichia coli*, or other sequenced bacteria genomes and archaea, or other prokaryotic microorganisms. In some aspects, the wild-type *Streptococcus pyrogenes* sequence can be modified. In some aspects, the nucleic acid sequence can be codon optimized for efficient expression in eukaryotic cells.

Disclosed herein, are CRISPR-Cas systems, referred to as CRISPRi (CRISPR interference), that utilizes a nuclease-dead version of Cas9 (dCas9). In some aspects, the dCas9 can be used to repress expression of one or more target sequences (e.g., tumor necrosis factor receptor (e.g., TNFR2), interleukin 1 receptor (e.g., IL1R2, IL6R), A-kinase anchor protein 5 (e.g., AKAP5, a glycoprotein (e.g., gp130) and transient receptor potential cation channel subfamily V member 1 (TRPV1)). In some aspects, the target sequences can be selected from one or more of the sequences listed in Table 5. In some aspects, the target sequences can be selected from one or more of the sequences listed in Table 5 in combination with one or more of the sequences listed in Table 1 and Table 3. Instead of inducing cleavage, dCas9 remains bound tightly to the DNA sequence, and when targeted inside an actively transcribed gene, inhibition of, for example, pol II progression through a steric hindrance mechanism can lead to efficient transcriptional repression. In some aspects, the dCas9 can be used to induce expression of one or more target sequences (e.g., aggrecan (ACAN), collagen type II alpha 1 chain (Col2A1), interleukin 10 (IL10) and indoleamine 2,3-dioxygenase 1 (IDO1)).

In some aspects, the CRISPR system can be used in which the nucleus has been deactivated. Further, a KRAB, VPR or p300 core can be attached. In some aspects, the KRAB is attached to downregulate one or more genes in a cell. In some aspects, the p300 core or VPR can be attached to upregulate one or more genes in a cell.

In some aspects, the CRISP-Cas system described herein can be used to upregulate or downregulate one or more genes in the same cell. In some aspects, the CRISP-Cas system described herein can also be used to upregulate and downregulate more than one gene or a combination thereof in the same cell. In some aspects, the expression of one or more genes (or gene products) can be decreased. In some aspects, the expression of one or more genes (or gene products) can be increased. In some aspects, the expression of one or more genes (or gene products) can be increased and decreased.

In some aspects, the vector comprises a regulatory element operably linked to an enzyme-coding sequence encoding a CRISPR enzyme (e.g., a Cas protein). In some aspects, the CRISPR enzyme can be Cas9 and can be from *Streptococcus pyogenes, Streptococcus thermophiles*, or *Treponema centicola*. In some aspects, the Cas9 can be dCas9. In some aspects, the Cas9 protein can be codon optimized for expression in the cell.

In some aspects, dCas9 can be used to silence one or more target genes (e.g., TNFR2, IL1R2, IL6R, AKAP5, gp130 and TRPV1). For example, dCas9 can be used to silence one or more genes through steric hindrance with or without an attached domain, such as KRAB. In some aspects, dCas9 can be used to induce activation of one or more target genes (e.g., IL10, IDO1, ACAN and Col2A1). dCas9 is the protein that interacts with gRNAs to place the desired editing proteins to specific sites. dCas9 can be used to silence (downregulate or turn off one or more genes). In some aspects, the dCas9 can be attached to KRAB to knockdown, silence or downregulate one or more genes. dCas9 can be used to activate (upregulate, increase expression, increase activity of or turn on one or more genes). In some aspects, the dCas9 can be attached to p300 core or VPR to turn on or upregulate one or more genes. Other proteins can be further attached to dCas9 or included in the CRISPR-Cas system and/or vectors described herein. For example, T2A, a self-cleaving peptide, can be included. T2A allows selection markers (e.g., GFP, fluorescent proteins, antibiotics) to also be attached. The attachment of such markers can be included to permit detection or selection of cells expressing the CRISPR-Cas system and/or vectors described herein Multiple gRNAs can be used to control multiple different genes simultaneously (multiplexing gene targeting), as well as to enhance the efficiency of regulating the same gene target.

TABLE 1

Examples of Target Sequences

| Target Gene | Name | Sequence | SEQ ID NO. |
|---|---|---|---|
| TNFR2 | gRNA 1 | 5'-GAAGGCTGGATGCGTGTTTA-3' | 13 |
| TNFR2 | gRNA 2 | 5'-TCAAGTGATCTTCCCGCCTC-3' | 14 |
| TNFR2 | gRNA 3 | 5'-GTGAGGGTGAGGCACTAATT-3' | 15 |
| TNFR2 | gRNA 4 | 5'-CGGGCTTTCGCTTTCAGTCG-3' | 16 |
| TNFR2 | gRNA 5 | 5'-AGGTATCGGCCCAGCGATGC-3' | 17 |
| TNFR2 | gRNA 6 | 5'-CATGTCCTAAAATCACGAAC-3' | 18 |
| TNFR2 | gRNA 7 | 5'-AATTGTGATACTAGCGGTTA-3' | 19 |
| IL1R2 | gRNA 1 | 5'-AGGATAAAACTAGGGCCCAT-3' | 20 |
| IL1R2 | gRNA 2 | 5'-CAAGGTTTTACGCTCCCATT-3' | 21 |
| IL1R2 | gRNA 3 | 5'-GGGAGGTGACACCCAGTTTA-3' | 22 |
| IL6R | gRNA 1 | 5'-TAAACACCTGACACACGGTC-3' | 23 |
| IL6R | gRNA 2 | 5'-CGGAAGACTCACCACCGTAA-3' | 24 |
| IL6R | gRNA 3 | 5'-AGGGCGTATCAGCCACCAGT-3' | 25 |
| IL6R | gRNA 4 | 5'-CGGCTTTCGTAACCGCACCC-3' | 26 |
| IL6R | gRNA 5 | 5'-AGAGCCGGGCTCCTGCGGAT-3' | 27 |
| gp130 | gRNA 1 | 5'-AGGCTCGTTTACGTAAGTCT-3' | 28 |
| gp130 | gRNA 2 | 5'-GGAATAACGGGGTCATGAAC-3' | 29 |
| gp130 | gRNA 3 | 5'-CAGTGGCCGCCTGTCGACGA-3' | 30 |
| gp130 | gRNA 4 | 5'-CGCACGAACCCCTTGGCGCC-3' | 31 |
| AKAP5 | gRNA 1 | 5'-TCAACAGGATCACGACCTTA-3' | 32 |
| AKAP5 | gRNA 2 | 5'-ATCGTGGTTCATCGCCAAAC-3' | 33 |
| AKAP5 | gRNA 3 | 5'-GCTGCATCTCTATGCGGACA-3' | 34 |
| AKAP5 | gRNA 4 | 5'-TTAGCGTCTCAGAAAACGCG-3' | 35 |
| AKAP5 | gRNA 5 | 5'-AAACTGTGCATAGAATAGCG-3' | 36 |
| AKAP5 | gRNA 6 | 5'-AAGATCAACGTAGGGCGTCG-3' | 37 |
| AKAP5 | gRNA 7 | 5'-CCTTGCTCCGGGTGCGACCG-3' | 38 |
| AKAP5 | gRNA 8 | 5'-GCGCCCGGGCGGAGCACGAT-3' | 39 |
| TRPV1 | gRNA 1 | 5'-AATTAGCTGGGCGCAATGGC-3' | 40 |
| TRPV1 | gRNA 2 | 5'-GAGTAGGGGTTGGCGTCGAG-3' | 41 |
| TRPV1 | gRNA 3 | 5'-GACGCTAGTTTTGACGTCGC-3' | 42 |
| TRPV1 | gRNA 4 | 5'-GAGTCGCTGTGGACGCCCTT-3' | 43 |
| TRPV1 | gRNA 5 | 5'-TGAAGGCGGTTGCTACTCGA-3' | 44 |
| TRPV1 | gRNA 6 | 5'-AAGGCAGCTGCTTGCATCGC-3' | 45 |

TABLE 2

Examples of Guide RNA Sequences (gRNAs)

| Target Gene | Name | Sequence | SEQ ID NO. |
|---|---|---|---|
| TNFR2 | gRNA 1 | 5'-GAAGGCUGGAUGCGUGUUUA-3' | 46 |
| TNFR2 | gRNA 2 | 5'-UCAAGUGAUCUUCCCGCCUC-3' | 47 |
| TNFR2 | gRNA 3 | 5'-GUGAGGGUGAGGCACUAAUU-3' | 48 |
| TNFR2 | gRNA 4 | 5'-CGGGCUUUCGCUUUCAGUCG-3' | 49 |
| TNFR2 | gRNA 5 | 5'-AGGUAUCGGCCCAGCGAUGC-3' | 50 |
| TNFR2 | gRNA 6 | 5'-CAUGUCCUAAAAUCACGAAC-3' | 51 |
| TNFR2 | gRNA 7 | 5'-AAUUGUGAUACUAGCGGUUA-3' | 52 |
| IL1R2 | gRNA 1 | 5'-AGGAUAAAACUAGGGCCCAU-3' | 53 |
| IL1R2 | gRNA 2 | 5'-CAAGGUUUUACGCUCCCAUU-3' | 54 |
| IL1R2 | gRNA 3 | 5'-GGGAGGUGACACCCAGUUUA-3' | 55 |
| IL6R | gRNA 1 | 5'-UAAACACCUGACACACGGUC-3' | 56 |
| IL6R | gRNA 2 | 5'-CGGAAGACUCACCACCGUAA-3' | 57 |
| IL6R | gRNA 3 | 5'-AGGGCGUAUCAGCCACCAGU-3' | 58 |
| IL6R | gRNA 4 | 5'-CGGCUUUCGUAACCGCACCC-3' | 59 |
| IL6R | gRNA 5 | 5'-AGAGCCGGGCUCCUGCGGAU-3' | 60 |
| gp130 | gRNA 1 | 5'-AGGCUCGUUUACGUAAGUCU-3' | 61 |
| gp130 | gRNA 2 | 5'-GGAAUAACGGGGUCAUGAAC-3' | 62 |
| gp130 | gRNA 3 | 5'-CAGUGGCCGCCUGUCGACGA-3' | 63 |
| gp130 | gRNA 4 | 5'-CGCACGAACCCCUUGGCGCC-3' | 64 |
| AKAP5(79) | gRNA 1 | 5'-UCAACAGGAUCACGACCUUA-3' | 65 |
| AKAP5(79) | gRNA 2 | 5'-AUCGUGGUUCAUCGCCAAAC-3' | 66 |
| AKAP5(79) | gRNA 3 | 5'-GCUGCAUCUCUAUGCGGACA-3' | 67 |
| AKAP5(79) | gRNA 4 | 5'-UUAGCGUCUCAGAAAACGCG-3' | 68 |
| AKAP5(79) | gRNA 5 | 5'-AAACUGUGCAUAGAAUAGCG-3' | 69 |
| AKAP5(79) | gRNA 6 | 5'-AAGAUCAACGUAGGGCGUCG-3' | 70 |
| AKAP5(79) | gRNA 7 | 5'-CCUUGCUCCGGGUGCGACCG-3' | 71 |
| AKAP5(79) | gRNA 8 | 5'-GCGCCCGGGCGGAGCACGAU-3' | 72 |
| TRPV1 | gRNA 1 | 5'-AAUUAGCUGGGCGCAAUGGC-3' | 73 |
| TRPV1 | gRNA 2 | 5'-GAGUAGGGGUUGGCGUCGAG-3' | 74 |
| TRPV1 | gRNA 3 | 5'-GACGCUAGUUUUGACGUCGC-3' | 75 |
| TRPV1 | gRNA 4 | 5'-GAGUCGCUGUGGACGCCCUU-3' | 76 |
| TRPV1 | gRNA 5 | 5'-UGAAGGCGGUUGCUACUCGA-3' | 77 |
| TRPV1 | gRNA 6 | 5'-AAGGCAGCUGCUUGCAUCGC-3' | 78 |

Methods

Methods of designing gRNAs. In some aspects, a commercially available tool, such as the UCSC genome browser (GRCh37/hg19), can be used to select sequences for the 5-UTR and the promoter region, 1000 base pairs upstream that can be entered into the CRISPR design tool (crispr.mit.edu). The design tool outputs 20 base pair gRNAs that are followed on their 3' end by the PAM sequence NGG, which is specific to the CRISPR-Cas9 system derived from *Streptococcus pyogenes*. The design tool can also score the potential gRNA sequences based on the number of off-target sties they may have and how many are within genes. The score ranges from 0-100, with a higher score meaning less off-target sites within genes. Guide RNAs described herein, for example, that had a score of 75 and above were selected for further study. The selected gRNAs can then be entered into the BLAT tool of the UCSC genome browser to inspect for overlap of gRNAs with DNAse hypersensitivity sites to ensure overlap. Any site that has DNAse hypersensitivity value above 0.01 can be targeted with a guide if one is available from the list of guides generated as described above. Additionally, any site that shows greater than 10 transcription factor binding sites within a region, as determined from ChiP-seq, can also be considered. Generally, the DNAse hypersensitivity data is consistent with these regions. Using the criteria described above, gRNAs (e.g., 4-7 gRNAs) that are spaced at least 100 base pairs apart can be selected for performing targeted gene repression and screening. In some aspects, TNFR1, TNFR2, IL1R2, IL6R, IL1R1, AKAP5, gp130, TRPV1, ACAN, Col2A1, I) and IDO1 gRNAs can be screened using the method disclosed herein. In some aspects, gRNA sequences from the promoter region and 5'UTR (crispr.mit.edu) can be selected. In some aspects, gRNA sequences can be 20 bp in length followed by a PAM sequence (e.g., NGG). In some aspects, gRNA sequences with the least off-target sequences and those that overlap with DNase sensitivity peaks can be selected.

Disclosed herein are methods of modulating expression of a gene in a cell. Disclosed herein are methods of decreasing expression of a gene in a cell. Disclosed herein are methods of increasing expression of a gene in a cell. In some aspects, the methods disclosed herein can be used to decrease and increase two or more genes in a cell, wherein at least one gene can be increased and at least one gene can be decreased. The method can include one or more of the following steps. First, introducing into a cell, a first nucleic acid. The first nucleic acid can encode a guide RNA comprising a DNA-binding domain. The nucleic acid can be operably linked to a regulatory element. The guide RNA described herein can be complementary to a target nucleic acid sequence disclosed herein comprising the gene. Next, a second nucleic acid encoding a transcriptional regulator protein or domain that modulates the target nucleic acid expression can be introduced into the cell. The second nucleic acid can further include a gRNA-binding domain. The second nucleic acid can be operably linked to a regulatory element. A third nucleic acid encoding a Cas9 (e.g., a deactivated nuclease (dCas9)) protein can be introduced. In some aspects, nuclease function can be removed. The third nucleic acid can be operably linked to a regulatory element. The Cas9 protein (e.g., dCas9) can interact with the guide RNA, and can be fused to the transcriptional regulator protein. The cell can then produce the guide RNA. The guide RNA can bind to the dCas9 protein and the transcriptional regulator protein or domain fused to the DNA-binding domain, and direct the complex (e.g., gRNA/dCas9 complex; the combined product of the gRNA and dCas9 interacting) to the DNA regulatory element encoded in the DNA-binding domain. The guide RNA and the dCas9 protein, for example, can co-localize to the target nucleic acid sequence. The transcriptional regulator protein or domain can modulate (increase or decrease) expression of the gene. The gRNA sequence can selected from the group listed in Table 6. In some aspects, the gRNA sequence can be selected from the group listed in Table 6 in combination with one or more gRNA sequences from the group listed in Tables 2 and 4. In some aspects, the expression of one or more genes can be increased.

Disclosed herein, are methods for introducing into a cell a CRISPR-Cas system. In some aspects, the CRISPR-Cas system can include one or more vectors described herein. In some aspects, the method can include one or more vectors. For example, the vector can comprise a promoter operably linked to one or more nucleotide sequences encoding a CRISPR-Cas system gRNA. In some aspects, the gRNA can hybridize with a target sequence of a DNA molecule in a cell. In some aspects, the vector can also include a regulatory element operably linked to a nucleotide sequence encoding a RNA-directed nuclease. In some aspects, the promoter operably linked to one or more nucleotide sequences encoding a CRISPR-Cas system gRNA and the regulatory element operably linked to a nucleotide sequence encoding a RNA-directed nuclease can be located on the same or different vectors of the same system. In some aspects, the method also includes a step wherein the gRNA targets and hybridizes with the target sequence and directs the RNA-directed nuclease to the DNA molecule. In some aspects, the gRNA sequence can be selected from the group listed in Table 6. In some aspects, the gRNA sequence can be selected from the group listed in Table 6 in combination with one or more gRNA sequences from the group listed in Tables 2 and 4. In some aspects, the target sequence can be selected from one or more of the sequences listed in Table 5. In some aspects, the target sequence can be selected from one or more of the sequences listed in Table 5 in combination with one or more of the sequences listed in Table 1 and Table 3.

Disclosed herein, are methods for introducing into a cell a vector. In some aspects, the vector can include a promoter operably linked to one or more nucleotide sequences encoding a CRISPR-Cas system gRNA. In some aspects, the vector can also include a regulatory element operably linked to a nucleotide sequence encoding a RNA-directed nuclease. In some aspects, the gRNA sequence can be selected from the group listed in Table 6. In some aspects, the gRNA sequence can be selected from the group listed in Table 6 in combination with one or more gRNA sequences from the group listed in Tables 2 and 4.

Disclosed herein, are methods for inducing site-specific DNA cleavage in a cell. The method can contacting a cell with a guide RNA. The guide RNA can be selected from the group listed in Table 6. In some aspects, the gRNA sequence can be selected from the group listed in Table 6 in combination with one or more gRNA sequences from the group listed in Tables 2 and 4. The guide RNA can include a sequence capable of binding to a target DNA. The method can further comprise the following step: contacting the cell with a Cas9 protein. In some aspects, the DNA can be in a cell. In some aspects, the cell can be a eukaryotic cell. In some aspects, the cell can be in an individual. In some aspects, the individual can be a human.

The method steps described herein can be carried out simultaneously or sequentially in any order. In some aspects, the DNA can be in a cell. In some aspects, the cell can be a eukaryotic cell. In some aspects, the cell can be in an individual. In some aspects, the individual can be a human.

Method of Treatment

The methods disclosed herein can be useful for the treatment of a subject having lower back pain. The methods disclosed herein can be useful for the treatment of a subject having degenerative disc disease. The methods disclosed herein can be useful for the treatment of a subject having arthritis. The methods disclosed herein can be useful for the treatment of a subject in need of musculoskeletal tissue engineering. The methods disclosed herein can be effective for targeting one or more receptors, including tumor necrosis factor receptor (e.g., TNFR2, TNFR1), interleukin 1 receptor (e.g., IL1R2, IL1R1, IL6R), A-kinase anchor protein 5 (e.g., AKAP5), a glycoprotein (e.g., gp130) and transient receptor potential cation channel subfamily V member 1 (TRPV1). The methods disclosed herein can be effective for targeting one or more genes (e.g., ACAN, Col2A1, IL10 and IDO1). In some aspects, the methods disclosed herein can be effective for targeting one or more receptors and one or more genes. In some aspects, the method scan also include the step of administering a therapeutic effective amount of the compositions disclosed herein (e.g., a CRISPR-Cas system comprising one or more vectors comprising: a) a promoter operably linked to one or more nucleotide sequences encoding a CRISPR-Cas system guide RNA (gRNA), wherein the gRNA hybridizes with a target sequence of a DNA locus in a cell; and b) a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA locus; wherein the gRNA sequence is selected from the group listed in Table 6. In some aspects, the gRNA sequence can be selected from the group listed in Table 6 in combination with one or more gRNA sequences from the group listed in Tables 2 and 4. In some aspects, the target sequences can be selected from one or more of the sequences listed in Table 5. In some aspects, the target sequences can be selected from one or more of the sequences listed in Table 5 in combination with one or more of the sequences listed in Table 1 and Table 3. In some aspects, expression of one or more genes can be increased. In some aspects, expression of two or more genes can be decreased. In some aspects, expression of ACAN, Col2A1, IL-10 and/or IDO1 can be increased. In some aspects, the methods can further include the step of identifying a subject (e.g., a human patient) who has low back pain, degenerative disc disease, arthritis, and/or a musculoskeletal system defect (e.g., bone or cartilage defect(s)) and then providing to the subject a composition comprising the CRISPR-Cas system or vector disclosed herein. In some aspects, the back pain can be caused by degenerative disc disease, discogenic, one or more facet joints, one or more muscles, inflammation or changes inflammatory cytokines. In some aspects, the subject can be identified using standard clinical tests known to those skilled in the art. Examples of tests for diagnosing degenerative disc disease include imaging (e.g., MRI, T2 weighted, T1rho). Subjects can also be identified as having axial back pain through self-reporting and completing the Oswestry low back disability questionnaire.

The therapeutically effective amount can be the amount of the composition administered to a subject that leads to a full resolution of the symptoms of the condition, disease or pain, a reduction in the severity of the symptoms of the condition, disease or pain, or a slowing of the progression of symptoms of the condition, disease or pain. The methods described herein can also include a monitoring step to optimize dosing. The methods can also include the step of determining the nucleic acid sequence of the specific cytokine or receptor present in a subject's DNA and then design the CRISPR-Cas system or vectors to comprise specific DNA binding domain sequences or gRNA sequences. The compositions described herein can be administered as a preventive treatment or to delay or slow the progression of degenerative changes or at the time of surgery.

The compositions disclosed herein can be used in a variety of ways. For instance, the compositions disclosed herein can be used for direct delivery of modified therapeutic cells, or lentivirus. In some aspects, the modified therapeutic cells can be engineered to overexpress, increased expression of or induce activation of genes that control regenerative capacity or ability, are involved in the extracellular matrix production or control anti-inflammatory responses. In some aspects, one or more modified therapeutic cells can be engineered to overexpress, increased expression of or induce activation one or more of ACAN, IL-10, Col2A1 and/or IDO1 genes. Such modified therapeutic engineered cells can possess an enhanced cellular property including but not limited to anti-inflammation or regenerative ability. The compositions disclosed herein can be used or delivered or administered at any time during the treatment process (e.g., during an already conducted surgery, when either a spinal fusion is being conducted, or a microdiscectomy). For example, the compositions described herein including cells or a virus can be delivered to the affected level in the microdiscetomy case, or to the adjacent levels to stop adjacent segment disease in the spinal fusion case.

In some aspects, the compositions disclosed herein can be administered or delivered to peripheral neurons (e.g., to regulate inflammatory interactions with the pain sensing neurons). Such treatment can be carried out if this type of interaction is suspected in back pain.

The dosage to be administered depends on many factors including, for example, the route of administration, the formulation, the severity of the patient's condition/disease/pain, previous treatments, the patient's size, weight, surface area, age, and gender, other drugs being administered, and the overall general health of the patient including the presence or absence of other diseases, disorders or illnesses. Dosage levels can be adjusted using standard empirical methods for optimization known by one skilled in the art. Administrations of the compositions described herein can be single or multiple (e.g., 2- or 3-, 4-, 6-, 8-, 10-, 20-, 50-, 100-, 150-, or more fold). Further, encapsulation of the compositions in a suitable delivery vehicle (e.g., polymeric microparticles or implantable devices) can improve the efficiency of delivery.

The therapeutically effective amount of the compositions described herein can include a single treatment or a series of treatments (i.e., multiple treatments or administered multiple times). Treatment duration using any of compositions disclosed herein can be any length of time, such as, for example, one day to as long as the life span of the subject (e.g., many years). For instance, the composition can be administered daily, weekly, monthly, yearly for a period of 5 years, ten years, or longer. The frequency of treatment can vary. For example, the compositions described herein can be administered once (or twice, three times, etc.) daily, weekly, monthly, or yearly for a 15 period of 5 years, ten years, or longer.

In some aspects, the compositions disclosed herein can also be co-administered with another therapeutic agent or in combination with microdiscectomy or spinal fusion surgery.

In some aspects, the methods disclosed herein also include treating a subject having degenerative disc disease. In some aspects, the methods disclosed herein also include treating a subject having arthritis. In some aspects, the methods disclosed herein also include treating a subject having a musculoskeletal system defect. In some aspects, the methods disclosed herein can include the step of determining TNF, IL1, IL6, IL8, IFN-gamma, IL17, ACAN, Col2A1, IL10 and/or IDO1 levels in a subject. In some aspects, the disclosed methods can further include the step of administering to the subject a pharmaceutical composition comprising a nucleic acid sequence encoding a CRISPR-associated endonuclease (e.g., deactivated endonuclease) and one or more guide RNAs, wherein the guide RNA is selected from the group listed in Table 6. In some aspects, the gRNA sequence can be selected from the group listed in Table 6 in combination with one or more gRNA sequences from the group listed in Tables 2 and 4. In some aspects, the CRISPR-associated endonuclease can be optimized for expression in a human cell. In some aspects, expression of one or more genes can be increased. In some aspects, expression of two or more genes can be decreased. In some aspects, expression of ACAN, Col2A1, IL-10 and/or IDO1 can be increased.

Pharmaceutical Compositions

As disclosed herein, are pharmaceutical compositions, comprising the compositions disclosed herein. For example, disclosed are pharmaceutical compositions, comprising a vector or CRISPR-Cas system comprising one or more vectors comprising: a) a promoter operably linked to one or more nucleotide sequences encoding a CRISPR-Cas system guide RNA (gRNA), wherein the gRNA hybridizes with a target sequence of a DNA locus in a cell; and b) a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA locus; wherein the gRNA sequence is selected from the group listed in Table 6. In some aspects, the gRNA sequence can be selected from the group listed in Table 6 in combination with one or more gRNA sequences from the group listed in Tables 2 and 4. In some aspects, the target sequence can be selected from one or more of the sequences listed in Table 5. In some aspects, the target sequence can be selected from one or more of the sequences listed in Table 5 in combination with one or more of the sequences listed in Table 1 and Table 3. In some aspects, the pharmaceutical compositions comprise the any one of the CRISPR-Cas system disclosed herein. In some aspects, the pharmaceutical composition comprises the nucleic acid sequence of any of the vectors or CRISPR-Cas systems disclosed herein. In some aspects, the pharmaceutical compositions further comprise a pharmaceutically acceptable carrier.

As used herein, the term "pharmaceutically acceptable carrier" refers to solvents, dispersion media, coatings, antibacterial, isotonic and absorption delaying agents, buffers, excipients, binders, lubricants, gels, surfactants that can be used as media for a pharmaceutically acceptable substance. The pharmaceutically acceptable carriers can be lipid-based or a polymer-based colloid. Examples of colloids include liposomes, hydrogels, microparticles, nanoparticles and micelles. The compositions can be formulated for administration by any of a variety of routes of administration, and can include one or more physiologically acceptable excipients, which can vary depending on the route of administration. Any of the nucleic acids and vectors and gRNAs described herein can be administered in the form of a pharmaceutical composition.

As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed. The compositions can also include additional agents (e.g., preservatives).

The pharmaceutical compositions as disclosed herein can be prepared for oral or parenteral administration. Pharmaceutical compositions prepared for parenteral administration include those prepared for intravenous (or intra-arterial), intramuscular, intervertebral subcutaneous, facet joint, dorsal root ganglion, intrathecal or intraperitoneal administration. Paternal administration can be in the form of a single bolus dose, or may be, for example, by a continuous pump. In some aspects, the compositions can be prepared for parenteral administration that includes dissolving or suspending the CRISPR-Cas systems, nucleic acids, polypeptide sequences or vectors in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

In some aspects, the CRISPR-Cas system disclosed herein can be directly injected via a lentivirus into the IVD without a carrier or with a biomaterial carrier. Any hydrogel or biomaterial designed for viral vector delivery can be used.

In some aspects, the cells can be administered to a desired location with or without a biomaterial carrier.

In some aspects, a virus comprising one or more vectors disclosed herein or the CRISPR-Cas system disclosed herein can be administered with or without a carrier to one or more peripheral nerves. In some aspects, the one or more peripheral nerves can be innervating the disc. Thus, the administration of the virus comprising any one of the compositions disclosed herein can be delivered (e.g., injected) to the disc site or dorsal root ganglion (DRG).

In some aspects, the compositions disclosed herein are formulated for intervertebral administration.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment. The compositions can also be formulated as powders, elixirs, suspensions, emulsions, solutions, syrups, aerosols, lotions, creams, ointments, gels, suppositories, sterile injectable solutions and sterile packaged powders. The active ingredient can be nucleic acids or vectors described herein in combination with one or more pharmaceutically acceptable carriers. As used herein "pharmaceutically acceptable" means molecules and compositions that do not produce or lead to an untoward reaction (i.e., adverse, negative or allergic reaction) when administered to a subject as intended (i.e., as appropriate).

In some aspects, the CRISPR-Cas system, vectors, gRNAs and nucleic acid sequences as disclosed herein can be delivered to a cell of the subject. In some aspects, such action can be achieved, for example, by using polymeric, biodegradable microparticle or microcapsule delivery vehicle, sized to optimize phagocytosis by phagocytic cells (e.g., macrophages).

In some aspects, the formulations include any that are suitable for the delivery of a virus (e.g., lentivirus) and cells. In some aspects, the route of administration includes but is not limited to injection into the disc, adjacent to the disc, or directly to the DRG for peripheral neuron transduction. Such administration can be done without surgery, or with surgery.

Kits

The kits described herein can include any combination of the compositions (e.g., CRISPR-Cas system or vectors) described above and suitable instructions (e.g., written and/ or provided as audio-, visual-, or audiovisual material). In some aspects, the kit comprises a predetermined amount of a composition comprising any one of the CRISPR-Cas or vectors disclosed herein. The kit can further comprise one or more of the following: instructions, sterile fluid, syringes, a sterile container, delivery devices, and buffers or other control reagents.

EXAMPLES

Example 1: CRISPR Epigenomic Editing of AKAP 150 in DRG Neurons Abolished Degenerative IVD Induced Sensitization of Sensory Neurons Materials and Methods Experimental overview. A set of four experiments was conducted in the degenerative IVD environment (e.g., inflammatory cytokines and low pH) on the sensitization of DRG neurons to noxious stimuli and to elucidate the factors and mechanisms mediating this sensitization. In the Degenerative IVD Conditioned Media Exposure experiments, rat DRG neurons were subjected to a range of temperatures during human degenerative and healthy IVD conditioned media exposure to determine the ability of factors released from degenerative IVD tissue to sensitize neurons and the magnitude of that sensitization. Following the degenerative IVD conditioned media exposure experiment, the IL-6 Blocking Experiments were performed to determine the role of IL-6 in the degenerative IVD sensitization of peripheral neurons. Once IL-6 was implicated as a mediator of neuron sensitization, the AKAP Inhibition Experiments were conducted to determine the mechanism by which IL-6 sensitizes DRG neurons. Following TRPV1 involvement in DRG sensitization, the Acidic pH-Degenerative IVD Conditioned Media Exposure experiments were conducted to determine the role of pH in DRG neuron sensitization and its ability to interact with the observed inflammation driven sensitization.

Once the IL-6/AKAP/TRPV1 pathway was identified as the main pathway for degenerative IVD induced neuron sensitization, the potential of CRISPR epigenome editing of neurons to regulate degenerative IVD induced sensitization via the targeting of AKAP in this pathway was investigated. Lentiviral constructs carrying the CRISPR epigenome editing system that targeted the AKAP gene promoter were designed, built, and validated for their ability to regulate AKAP expression in peripheral neurons. Validated CRISPR AKAP targeting epigenome editing vectors were selected, and delivered to DRG neurons prior to exposure to degenerative IVD sensitization model and tested for an ability to regulate previously demonstrated sensitization via IL-6/ AKAP/TRPV1 pathway.

Degenerative intervertebral disc (IVD) conditioned media. IVD tissue was obtained from five patients undergoing surgical intervention for axial back pain, degenerative disc disease, and lumbar spondylosis. IVD tissue was extracted from lumbar discs for all patients. Patients showed signs of degenerative disc disease on magnetic resonance imaging (MRI) and reported axial back pain. Additionally, non-degenerative IVD tissue was obtained from three trauma patients with no prior history of axial back or neck pain. IVD tissue was transferred into a glass petri dish, washed twice in washing medium (DMEM-HG (Life Technologies) supplemented with 1% gentamycin (Gibco), 1% kanamycin (Sigma) and 1% fungizone (Gibco)) and cut into small pieces (~3 mm$^2$). Next, the IVD tissue was weighed, transferred to a 75 cm$^2$ tissue culture flask, and cultured in DMEM-HG supplemented with 50 µg/ml ascorbic acid (Life Technologies), 5 µg/ml gentamicin, and 0.125 µg/ml fungizone at a media to tissue ratio of 3.5 ml/g for 48 hours (37° C. and 5% $CO_2$) (Krock E, Rosenzweig D H, Chabot-Dore A J, Jarzem P, Weber M H, Ouellet J A, Stone L S, Haglund L. J. Cell. Mol. Med. 2014; 18:1213-25). After incubation, IVD conditioned media was collected, and stored at −80° C. until needed.

Dorsal root ganglion (DRG) neuron cell culture. Postnatal (p1-p4) Sprague Dawley rat DRGs were explanted, placed in L-15 medium (Gibco), and cleaned of anterior and posterior roots and connective tissue. Ganglia were dissociated in 2 mL of L-15 medium supplemented with 500 µL of collagenase IV (1.33%, Worthington Biochemical) for 30 minutes at 37° C. The cell suspension was centrifuged at 1000 RPM for 5 minutes after which the supernatant was aspirated and the cells were incubated in 4 mL of DMEM/F-12 supplemented with 1 mL of 1% trypsin (Worthington Biochemical) plus 50 µL of 1% DNase I (Worthington Biochemical) for 20 minutes at 37° C. Following incubation, 1 mL of soybean trypsin inhibitor (SBTI) (Worthington Biochemical) was added to the cell suspension and the cell suspension was centrifuged at 1000 RPM for 5 minutes. Next, the supernatant was aspirated, cells were resuspended in 1 mL of DMEM/F-12 plus 50 µL of 1% DNase and triturated through a fire polished Pasteur pipette. Rat DRG neurons were seeded onto laminin (Life Technologies) coated 35 mm tissue culture dishes at a density of 50,000 cells per dish and cultured in 1.5 mL of SATO$^-$ medium (DMEM/F12 supplemented with 2.2% SATO-mix, 1% transferrin (Sigma), 2% insulin (Sigma), 1% Glutamax (Invitrogen), 0.5% gentamicin, and 2.5 S NGF (10 ng/ml, Worthington Biochemical) for 2-6 days until experiment.

Calcium imaging of action potentials. Rat DRG neurons were loaded with the calcium indicator dye Fluo-4AM (Molecular Probes, 3 µM) and incubated in the dark at 37° C. for 1 hour. Fluorescent measurements of calcium were performed using a multi-photon microscope (Bruker/Prairie View, excitation 810 nm, emission 545 nm, 0.5 Hz). Neurons were incubated at 37° C. for 15 minutes to establish the baseline calcium signal and then exposed to heat stimuli for two minutes while imaging. Cells were returned to the baseline temperature for 5 minutes between exposures to elevated temperatures. 100 DRG neurons were imaged and analyzed for each treatment group.

Figures 1A, 1B, 1C, 1D, 1E:
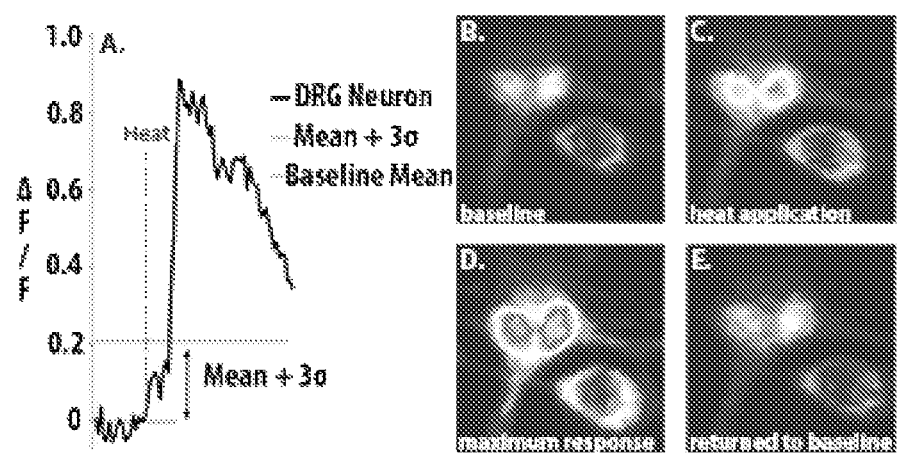
FIGS. 1A-E show DRG neuron imaging.

Image analysis was conducted using Fiji software (Schindelin J, Arganda-Carreras I, Frise E, Kaynig V, Longair M, Pietzsch T, Preibisch S, Rueden C, Saalfeld S, Schmid B, Tinevez J Y, White D J, Hartenstein V, Eliceiri K, Tomancak P, Cardona A. Nat. Methods 2012; 9:676-82). The background signal was subtracted from each cell and the mean baseline ($F_0(t)$) was calculated at 37° C.

$$\frac{\Delta F}{F} = \frac{(F(t) - F_0(t))}{F_0(t)} \quad [1]$$

was calculated for each cell across the entire experiment. The baseline mean and standard deviation of $\Delta F/F$ was calculated for all cells at 37° C. Neurons were considered to be firing (generating an action potential) in response to heat stimuli if the $\Delta F/F$ for the cell was 3 standard deviations greater than the mean baseline value (Greffrath W, Kirschstein T, Nawrath H, Treede R D. Neuroscience 2001; 104:539-550) at 37° C. (FIG. 1) in response to heat stimulation.

Degenerative IVD Conditioned Media Exposure. Media were replaced with fresh SATO-media and 0.75 ml of unconditioned DMEM (control media, n=5), degenerative IVD conditioned (n=5 patients), or healthy IVD conditioned media (n=3 patients) and cultured for 24 hours (37° C., 5% $CO_2$). Following incubation, neurons were loaded with the calcium indicating dye Fluo-4AM as described in the Calcium Imaging of Action Potentials section. Neurons were incubated at 37° C. for 15 minutes to establish a baseline calcium signal and then exposed to heat of 38, 39, 40, 42, and 44° C. for two minutes while imaging. Cells were returned to the baseline temperature for 5 minutes between exposures to elevated temperatures.

IL-6 blocking experiments. Mouse monoclonal anti-human IL-6 antibody (Life Technologies, 20 µg/mL) or mouse isotype control antibody (Life Technologies, 20 µg/mL) were added to degenerative IVD conditioned media and incubated at 37° C. for three hours prior to addition to neurons as described in the Degenerative IVD Conditioned Media Exposure section (n=5 patients). Degenerative IVD conditioned media not receiving antibody treatment and control media (DMEM supplemented with 5 µg/ml gentamicin and 0.125 µg/ml fungizone) were incubated at 37° C. for three hours prior to addition to neurons as described in the Degenerative IVD Conditioned Media Exposure section (n=5). Neurons were incubated at 37° C. for 15 minutes to establish a baseline calcium signal and then exposed to heat stimulation of 38, 39, 40, 42, and 44° C. for two minutes while imaging. Cells were returned to the baseline temperature for 5 minutes between exposures to elevated temperatures.

AKAP inhibition experiments. DRG neurons were loaded with the calcium dye Fluo-4AM (3 µM) and incubated in the dark at 37° C. for 1 hour. The AKAP inhibitor peptide St-Ht31 (Promega, 50 µM) or the control peptide St-Ht31P (Promega, 50 µM) were added to the DRG neurons and incubated at 37° C. for 15 minutes. Following incubation, degenerative IVD conditioned media (n=3 patients) or control media were added to the peptide exposed neurons and incubated for 15 minutes (n=3). Additionally, separate groups of neurons were exposed to control media or degenerative IVD conditioned media without peptide exposure under the same conditions (n=3 patients). Following this incubation, a 15 minute baseline calcium signal at 37° C. was established and cells were exposed to heat stimulation of 39° C. while imaging.

Acidic pH-degenerative IVD conditioned media exposure. Experiments were conducted as described in the Degenerative IVD Conditioned Media Exposure section (n=4 patients) with the following experimental treatment groups: normal pH (7.4) control media (DMEM), normal pH (7.4) IVD conditioned media, low pH (6.5) control media, and low pH (6.5) IVD conditioned media. Control media (DMEM) or degenerative IVD conditioned media were equilibrated in an incubator for 24 hours (37° C., 5% $CO_2$). Following incubation, the pH of the acidic pH groups was lowered to a pH of 6.5 by the addition of HCL (1 M, Sigma-Aldrich) and the normal pH groups maintained at a pH of 7.4.

Lentiviral CRISPR epigenome editing vector construction. CRISPR epigenome editing vectors were created that co-expresses dCAS-KRAB-T2A-GFP and gRNAs that target AKAP 150. First, the promoter region of rat AKAP 150 are screened for gRNA target sequences with the necessary adjacent protospacer adjacent motif (PAM: -NGG) and selected based on minimizing off-target binding sites using a publically available algorithm (Hsu P D, Scott D A, Weinstein J A, Ran F A, Konermann S, Agarwala V, Li Y, Fine E J, Wu X, Shalem O, Cradick T J, Marraffini L A, Bao G, Zhang F. Nat. Biotechnol. 2013; 31:827-32). Four guides are screened per promoter region that target every ~250 bp (data and sequences obtained from the UCSC genome browser (Kent W J, Sugnet C W, Furey T S, Roskin K M, Pringle T H, Zahler A M, Haussler D. Genome Res. 2002; 12:996-1006). The non-target guide oligonucleotide was designed as a scramble DNA sequence that does not match the rat genome. Oligonucleotides are obtained (University of Utah DNA/Peptide Synthesis Core), hybridized, phosphorylated and cloned into gRNA expressing plasmids (addgene plasmid 47108) using BbsI sites. To produce a lentiviral vector that co-expresses dCAS-KRAB-T2A-GFP and gRNA, gRNA cassette are cloned via PCR and inserted into $3^{rd}$ generation lentiviral transfer vector that expresses dCas-KRAB-T2A-GFP under the control of the human UbC promoter via BsmBI sites. To produce transduction media (DMEM), epigenome editing vector constructs were produced in HEK 293T cells using a previously reported method (Salmon P, Trono D. Curr. Protoc. Neurosci. 2006; Chapter 4: Unit 4.21) and stored at −80° C. until use. For transduction of rat DRG neurons, media were removed and replaced with transduction media supplemented with polybrene (8 µg/ml) and cells were cultured for 24 hours. The next day, viral media was removed replaced with fresh SATO-medium. Transduced DRG neurons were cultured in SATO-medium under standard cell culture conditions until experiments were performed.

AKAP5 quantitative reverse-transcription PCR. Four days following transduction, cells were harvested for total RNA using the PureLink RNA microscale kit (LifeTech). cDNA synthesis was conducted using the High Capacity cDNA RT kit (Lifetech). qRT-PCR using Taqman Universal PCR Master Mix (LifeTech) was performed with the TaqMan Gene Expression Detection Assay (LifeTech) with oligonucleotide primers for AKAP 150 and GAPDH. Results are expressed as fold increase in mRNA expression of AKAP 150 normalized to GAPDH expression using the $\Delta\Delta C_t$ method.

AKAP epigenome edited neuron sensitization. DRG neurons were transduced with epigenome editing lentiviral constructs targeting the AKAP 150 gene promoter region or a non-target gRNA, as described above, and cultured in SATO-medium for 4 days following removal of lentivirus. Successful transduction was verified via fluorescent imaging of GFP in transduced neurons. Following the culture period, transduced and naïve (non-transduced) DRG neurons were exposed to degenerative IVD conditioned media or control media (DMEM) and incubated for 24 hours. Following incubation, neurons were loaded with the calcium indicator dye rhod-2AM (Molecular Probes, 3 µM) and incubated in the dark at 37° C. for 1 hour. Fluorescent measurements of calcium were performed using a multi-photon microscope (Bruker/Prairie View, excitation 1105 nm, emission 585 nm, 0.5 Hz). Neurons were incubated at 37° C. for 15 minutes to establish a baseline calcium signal and then exposed to heat stimuli of 38, 39, 40, 42, and 44° C. for two minutes while imaging. Cells were returned to the baseline temperature for 5 minutes between exposures to elevated temperatures.

Curve Fitting of Neuron Firing. Data from the conditioned media and IL-6 blocking experiments were fit to the sigmoidal Boltzmann equation:

$$y = \min + \frac{(\max - \min)}{1 + \exp\left(\frac{T_{50} - x}{\text{slope}}\right)} \quad [2]$$

with the percentage of neurons firing plotted as a function of temperature. Each trial was individually fit to produce values for T50 and max. T50 was defined as the temperature at which 50 percent of the maximum response occurs. The max was defined as the maximum percentage of neurons firing predicted by the curve fitting.

Statistical analysis. Degenerative IVD conditioned media exposure and IL-6 blocking experiment data were analyzed by two-way analysis of variance (ANOVA) on repeated measures with Tukey's post hoc test, treating media condition and temperature as factors. AKAP inhibitor experiment data, T50 and maximum response data from IL-6 blocking experiments were analyzed by one-way ANOVA with Tukey's post hoc test, treating media condition as the factor. Degenerative IVD pH level experiment data were analyzed by two-way ANOVA with Tukey's post hoc test, treating media condition and temperature as factors. Significance was tested at $\alpha=0.05$ for all statistical analyses.

Figures 2A, 2B, 2C:
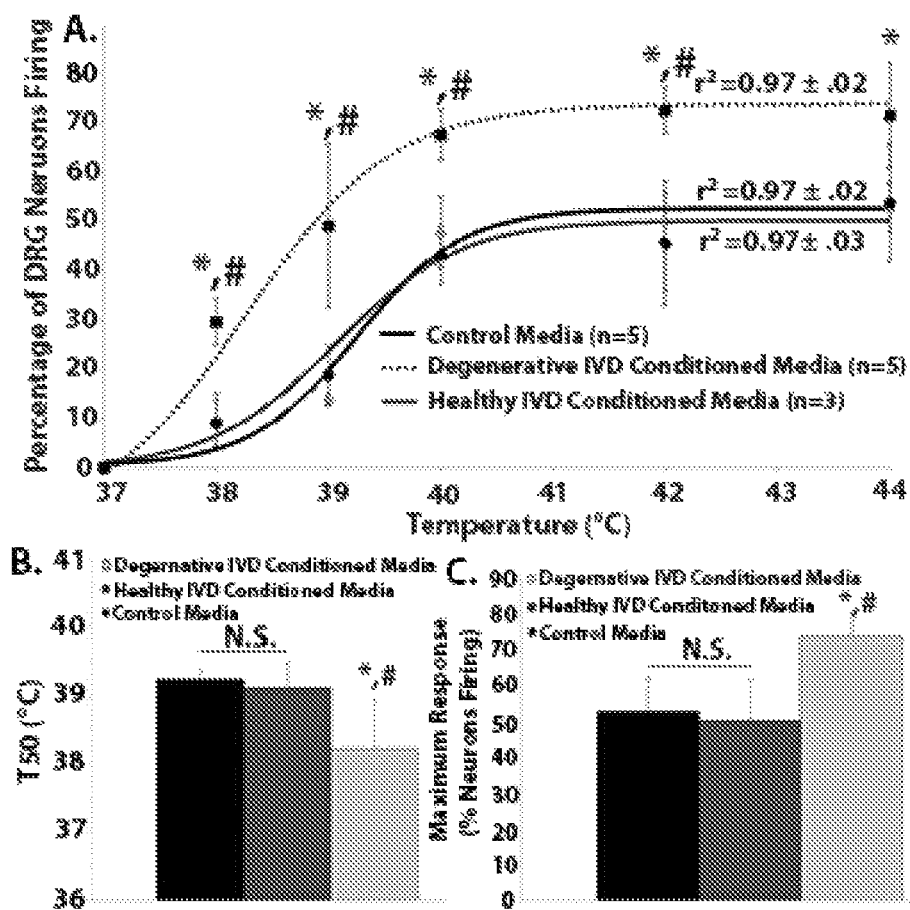
FIGS. 2A-C show degenerative IVDs sensitize peripheral neurons to heating.

Results. Degenerative IVD conditioned media triggers sensitization of DRG neurons to heat stimuli. The percentage of rat DRG neurons firing when exposed to degenerative IVD conditioned media was significantly elevated over the neurons firing in the control media group (p<0.05) and healthy IVD conditioned media group (p<0.05) at temperatures as low as 38° C. (FIG. 2A). In addition, the percentage of neurons firing when exposed to healthy IVD conditioned media was similar to the percentage of neurons firing in the control media group at all temperatures tested (FIG. 2A).

The percentage of neurons firing as a function of temperature was well defined by curve fitting the data to the Boltzmann equation for the control media ($r^2=0.97\pm0.02$), healthy IVD conditioned media ($r^2=0.97\pm0.03$), and degenerative IVD conditioned media ($r^2=0.97\pm0.02$) treatment groups (FIG. 2A). The T50, the temperature at which half the maximum firing response occurs, and maximum firing response were calculated via Boltzmann equation fits to each trial. The T50 value of neurons exposed to thermal stimuli in the presence of degenerative IVD conditioned media (38.25° C.±0.77) was significantly lower than the T50 values in both the control media (39.25° C.±0.13, p<0.05) and the healthy IVD conditioned media treatment groups (39.12° C.±0.38, p<0.05)(FIG. 2B). In addition, the maximum firing response of neurons exposed to thermal stimuli in the presence of degenerative IVD conditioned media (73.69%±6.5) was significantly greater than the maximum response in the control media (52.69%±9.42, p<0.05) and healthy IVD conditioned media treatment groups (51.25%±11.58, p<0.05)(FIG. 2C).

Figures 3A, 3B, 3C, 3D:
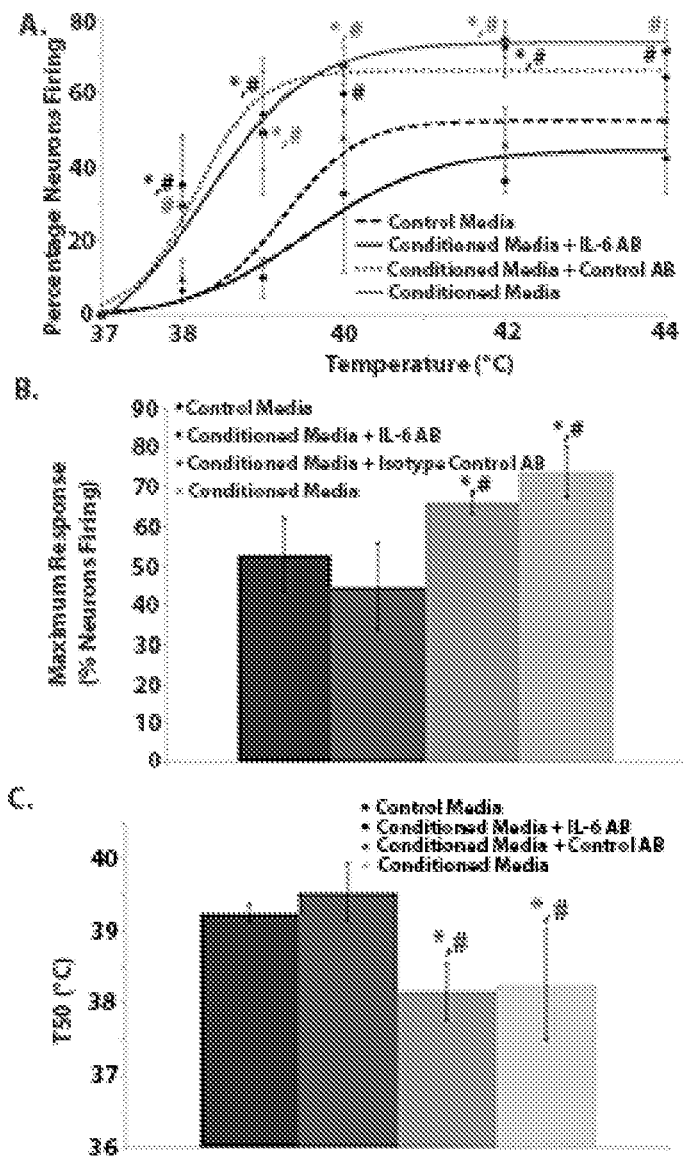
FIGS. 3A-D show that IL-6 is the primary mediator of peripheral neuron sensitization in the degenerative IVD.

IL-6 is the primary mediator of sensitization of DRG neurons by degenerative IVD conditioned media. The results from the original sensitization experiments were repeated and confirmed as the percentage of rat DRG neurons firing when exposed to heat stimuli in the presence of degenerative IVD conditioned media was significantly elevated (p<0.05) when compared to the percentage of neurons firing in the control media group at temperatures as low as 38° C. (FIG. 3A). When rat DRG neurons were exposed to heating in the presence of degenerative IVD conditioned media supplemented with IL-6 blocking antibody, the firing response returned to control media levels (p=1.0) for all temperatures tested (FIG. 3A) and was significantly less (p<0.05) than the percentage of neurons firing in the degenerative IVD conditioned media group at all temperatures above 38° C. (FIG. 3A). In contrast, addition of the isotype control antibody had no effect on firing response compared to degenerative IVD conditioned media group (p=0.895) (FIG. 3A). Furthermore, the IL-6 sensitization effect was seen in all patients tested, as all patients showed a decreased (p<0.05) firing response after IL-6 blocking antibody exposure (FIGS. 3A, D).

The number of neurons firing as a function of temperature was well defined by curve fitting the data to the Boltzmann equation for the control media ($r^2=0.97\pm0.02$), degenerative IVD conditioned media ($r^2=0.97\pm0.02$), IL-6 blocking antibody ($r^2=0.98\pm0.02$), and isotype control antibody ($r^2=0.94\pm0.04$) treatment groups (FIG. 3A). The T50 and maximum firing response were calculated via Boltzmann equation fits to each trial. The T50 value of neurons exposed to heat stimuli in the presence of conditioned media supplemented with IL-6 blocking antibody (39.53° C.±0.4) returned to control media levels (39.25° C.±0.13, p=0.993) and was significantly greater than the T50 values of neurons in both the conditioned media (38.25° C.±0.77, p=0.004) and isotype control antibody groups (38.16° C.±0.4, p=0.003) (FIG. 3B). In addition, the maximum firing response of DRG neurons exposed to heat stimuli in the presence of conditioned media supplemented with IL-6 blocking antibody (44.6%±11%) returned to control media levels (52.7%±9.4%, p=0.534) and is significantly less than the maximum firing response of neurons in the conditioned media (73.7%±6.5%, p<0.0001) and isotype control antibody groups (66%±2.8%, p=0.001) (FIG. 3C).

Inhibition of AKAP abolishes IL-6 mediated sensitization of rat DRG neurons by degenerative IVD conditioned media. Sensitization by degenerative IVD conditioned media was once again confirmed as the percentage of DRG neurons firing at 39° C. exposed to degenerative IVD conditioned media (59.72%±18.9%) was significantly greater (p=0.007) than the percentage of neurons firing in the control group (14.36%±2.3%, FIG. 4). When neurons were exposed to degenerative IVD conditioned media in the presence of the AKAP inhibitor St-Ht31, the percentage of neurons firing returned to baseline levels (15.51%±2.7%) and was not significantly different from the control media group (p=0.998, FIG. 4). In addition, the percentage of neurons firing in the degenerative IVD conditioned media supplemented with the control peptide St-Ht31P (61.91%±13.9%) was significantly greater than the control media (p=0.006) and the St-Ht31 groups (p=0.006), but not significantly different from the degenerative IVD conditioned media group (p=0.996, FIG. 4).

Figure 4:
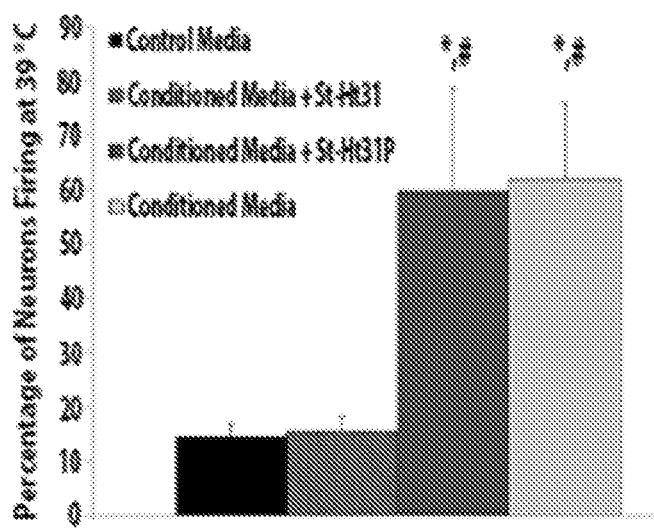
FIG. 4 shows that AKAP mediates sensitization of DRG neurons to heating in the degenerative IVD. Values are the mean±standard deviations. *=p<0.01 compared to the control media group. #=p<0.01 when compared to the degenerative IVD conditioned media plus St-Ht31P group.

FIG. 4 shows the results of the experiments described above as a percentage of rat DRG neurons firing exposed to 39° C. in the presence of control media, degenerative IVD conditioned media, degenerative IVD conditioned media supplemented with the AKAP inhibitor peptide St-Ht31 (50 µM) or degenerative IVD conditioned media supplemented with the control peptide St-Ht31P (50 µM). n=3 for all groups tested.

Degenerative IVD conditioned Media and pathological acidic pH levels synergistically enhance sensitization of rat DRG neurons to heat stimuli and trigger spontaneous neuron firing. The percentage of rat DRG neurons firing when exposed to pH 6.5 degenerative IVD conditioned media was significantly elevated (p<0.05) over all other media conditions tested at 37° C., 38° C., and 39° C. At 37° C., spontaneous neuron firing occurred in neurons in the pH 6.5 degenerative IVD conditioned media group (13±4.2%, FIG. 5), which had not been observed in any other experiment or group tested.

Figure 5:
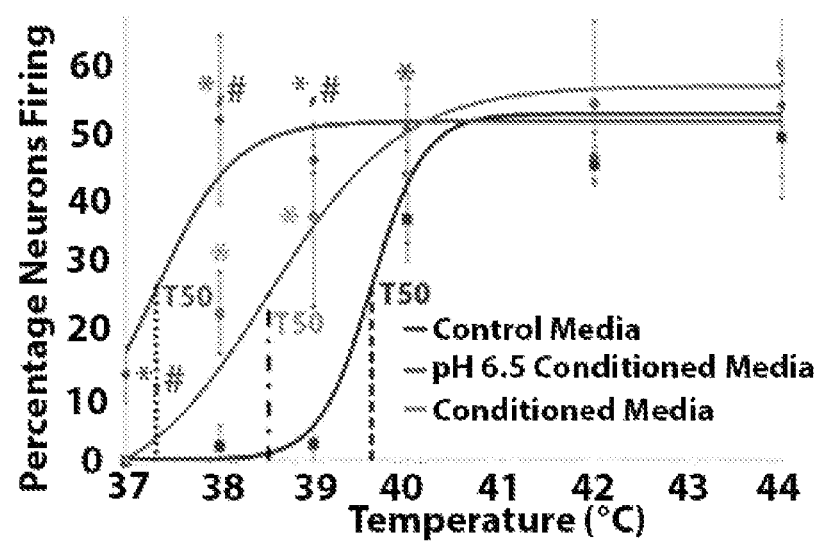
FIG. 5 shows degenerative IVD conditioned media and acidic pH synergistically enhance sensory neuron desensitization to heating and trigger spontaneous firing.

The T50 values of neurons in the pH 6.5 degenerative IVD conditioned media group (37.32±0.39° C., p=0.02, FIG. 5B) was significantly decreased compared to the degenerative IVD conditioned media (38.48±0.28° C.), the pH 6.5 control media (39.76±0.76° C., p=0.01), and the control media (39.62±0.24° C., p=0.02) groups (FIG. 5).

FIG. 5 shows the results from the experiments described above as the percentage of rat DRG neurons firing exposed to heat stimuli in the presence of control media (pH 7.4 degenerative IVD conditioned media (pH 7.4), or pH 6.5 degenerative IVD conditioned media (n=4) *=p<0.05 when compared to the control media group, #=p<0.05 when comparing pH 6.5 degenerative IVD conditioned media group to degenerative IVD conditioned media group (pH 7.4).

Epigenome editing of AKAP promoter in rat DRG neurons abolishes degenerative IVD mediated sensitization of rat DRG neurons. Transduction of DRG neurons with CRISPR epigenetic editing lentiviral vectors targeting AKAP 150 (FIG. 6C) regulated expression of AKAP 150 (FIG. 6D) with AKAP guide 4 exhibiting maximum downregulation when compared to DRG neurons transduced with non-target lentiviral vectors (21.03% of non-target expression, p<0.05).

Figures 6A, 6B, 6C, 6D, 6E, 6F, 6G:
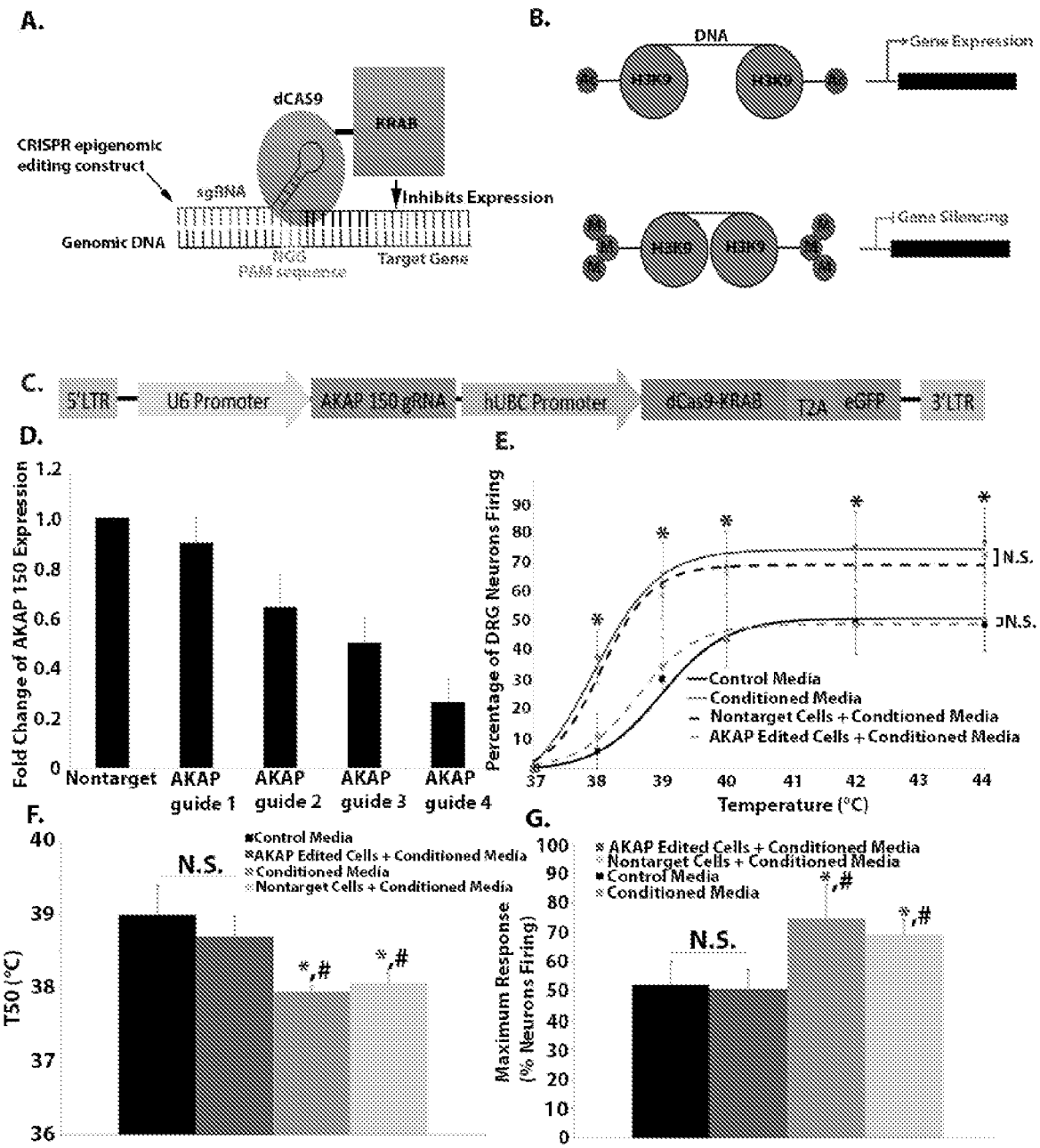
FIGS. 6A-G show epigenomic editing of AKAP 150 expression in DRG Neurons abolishes degenerative IVD induced neuron sensitization to heating.

The percentage of neurons firing in naïve (non-transduced) neurons and neurons receiving non-targeting lentiviral vectors subjected to thermal stimuli in the presence of degenerative IVD conditioned media were significantly elevated when compared to the control media group (p<0.05) at all temperatures tested. When AKAP 150 epigenome edited neurons were exposed to degenerative IVD conditioned media, the percentage of neurons firing returned to baseline levels (FIG. 6E) and were not significantly different from control media levels. From the curve fitting, the T50 value of AKAP egigenomically edited neurons exposed to degenerative IVD conditioned media (38.7±0.29° C.) was significantly lower than T50 value of naïve (37.94±0.07° C., p=0.003) and non-target epigenomically edited neurons (38.7±0.29° C., p=0.01), yet not significantly different from the control media group (38.99±0.39° C., p=0.3298)(FIG. 6F). The maximum response of AKAP epigenomically edited neurons exposed to degenerative IVD conditioned media (50.63±6.59%) returned to control levels (51.12±8.02%, p=0.9959) and was significantly decreased compared to the maximum response of naïve (74.48±11.06%, p=0.001) and non-target epigen-omically edited neurons (69.14±4.93%, p=0.001) exposed to degenerative IVD conditioned media (FIG. 6G).

Discussion. The interactions between the degenerative IVD environment (inflammatory cytokines and pH) and peripheral neurons were modeled and investigated to provide insight into the underlying mechanisms of discogenic back pain. The data presented herein demonstrates that degenerative IVD produces specific factors/cytokines capable of directly sensitizing DRG neurons to heat stimuli and that sensitization is enhanced at pH levels experienced by neurons in the degenerative IVD. This sensitization led to spontaneous firing of neurons and a T50 firing threshold (37.32±0.39° C.) near resting core body temperature, but was not observed in unconditioned media or media conditioned with healthy IVD. Blocking IL-6 in the conditioned media abolished the entirety of this sensitization, and sensitization was also abolished after inhibiting AKAP 150, indicating sensitization occurs through the IL-6/AKAP/TRPV1 pathway. Once the IL-6/AKAP/TRPV1 pathway was established as mediating sensitization, the ability of CRISPR epigenome editing of peripheral neurons to regulate sensitization was investigated. This data demonstrates that epigenome editing of AKAP 150 expression in rat DRG neurons abolishes degenerative IVD sensitization of neurons to thermal stimuli while these neurons maintain their non-pathological firing response. Together, these results implicate the synergistic effects of acidic pH and the activation of the IL-6/AKAP/TRPV1 as the underlying mechanism for degenerative IVD induced neuron sensitization, demonstrates CRISPR epigenomic editing of AKAP expression regulates neuron sensitization and establishes CRISPR epigenome editing of nociceptive neurons as a possible treatment strategy for discogenic pain.

Factors released from degenerative IVDs sensitize DRG neurons to noxious stimuli, particularly heating were demonstrated. Previous studies have demonstrated increased cytokine levels (e.g. TNF-α, IL-1β, IL-6, and IL-8) in painful IVDs (Burke J G, Watson R W G, McCormack D, Dowling F E, Walsh M G, Fitzpatrick J M. J. bone Jt. Surg. Br. Vol. 2002; 84:196-201; Le Maitre C L, Pockert A, Buttle D J, Freemont A J, Hoyland J A. Biochem. Soc. Trans. 2007; 35:652-5; Le Maitre C L, Richardson S M A, Baird P, Freemont A J, Hoyland J A. J. Pathol. 2005; 207:445-52; Shamji M F, Setton L A, Jarvis W, So S, Chen J, Jing L, Bullock R, Isaacs R E, Brown C, Richardson W J. 2010; 62:1974-82; and Specchia N, Pagnotta A, Toesca A, Greco F. Eur. Spine J. 2002; 11:145-51) and that inflammatory cytokines are capable of sensitizing rodents to thermal and mechanical stimuli in the paw in models of radiculopathy and peripheral neuropathy (Bowles R D, Karikari I O, VanDerwerken D N, Sinclair M S, Bell R D, Riebe K J, Huebner J L, Kraus V B, Sempowski G D, Setton L A. Eur. J. Pain 2015; Obreja O, Schmelz M, Poole S, Kress M. Pain 2002; 96:57-62; and Opree A, Kress M. J. Neurosci. 2000; 20:6289-93). The findings disclosed herein demonstrate an ability for the degenerative IVD conditions, but not healthy IVD tissue, to directly lead to afferent neuron sensitization. These findings support the hypothesis that inflammation driven sensitization of nociceptive neurons in the degenerative IVD could contribute to discogenic back pain via sensitization and establish an in vitro model, which can be used to study these interactions and screen novel therapeutics.

In this study, the degenerative IVD conditioned media combined with acidic pH was capable of inducing spontaneous neuron firing and sensitizing afferent neurons to noxious stimuli at temperatures as low as 37° C. Under these sensitized conditions, the T50 value (37.3° C.) falls within the normal core body temperature range (36.1-37.8° C.) and the maximum response is observed just above this range (38° C.), with 13% of neurons spontaneously firing at the mean core temperature of 37° C. Since the majority of neurons innervating the IVD are nociceptive neurons that co-express CGRP and TRPV1, a pathological ability for TRPV1 channels to fire at sub 38° C. temperatures would provide a mechanism for nociceptive signaling in the degenerative IVD. This data suggests that TRPV1 in the disc may play a role in discogenic back pain due to synergistic pH and inflammatory cytokine mediated sensitization.

This data indicates that IL-6 is the main mediator of the neuron sensitization observed after exposure to degenerative IVD conditioned media. Multiple inflammatory cytokines have been observed in the pathological IVD, which includes TNF-α, IL-1β, IL-6, and IL-8 (Burke J G, Watson R W G, McCormack D, Dowling F E, Walsh M G, Fitzpatrick J M. J. bone Jt. Surg. Br. Vol. 2002; 84:196-201; Le Maitre C L, Pockert A, Buttle D J, Freemont A J, Hoyland J A. 2007; 35:652-5; Le Maitre C L, Richardson S M A, Baird P, Freemont A J, Hoyland J A. J. Pathol. 2005; 207:445-52; Shamji M F, Setton L A, Jarvis W, So S, Chen J, Jing L, Bullock R, Isaacs R E, Brown C, Richardson W J. Arthritis Rheum. 2010; 62:1974-82; and Specchia N, Pagnotta A, Toesca A, Greco F. Eur. Spine J. 2002; 11:145-51). IL-1β and TNF-α (Le Maitre C L, Hoyland J A, Freemont A J. Arthritis Res. Ther. 2007; 9:R77; Le Maitre C L, Pockert A, Buttle D J, Freemont A J, Hoyland J A. Biochem. Soc. Trans. 2007; 35:652-5; and Shamji M F, Setton L A, Jarvis W, So S, Chen J, Jing L, Bullock R, Isaacs E, Brown C, Richardson W J, Carolina N, Hospital T O. 2011; 62:1974-1982) are the most common cytokines investigated in disc pathology due to their role in extracellular matrix breakdown and implication in rodent models of radiculopathy. TNF-α, IL-1β and IL-6 have all been hypothesized to contribute to discogenic back pain; however, this data demonstrates that blocking IL-6 action in the degenerative conditioned media abolished the thermal sensitivity and demonstrated IL-6 as a main mediator of inflammatory sensitization of neurons in these experiments and not TNF-α or IL-1β. Furthermore, IL-6 dependent sensitization was observed in neurons exposed to conditioned media from all patients tested suggesting the same mechanism may exist in the larger patient population. It's important to note that DRG neurons do not express membrane bound IL-6 receptor but rather IL-6 signals via trans-signaling through a complex formed by IL-6, soluble IL-6 receptor and gp130 (Andratsch M, Mair N, Constantin C E, Scherbakov N, Benetti C, Quarta S, Vogl C, Sailer C A, Uceyler N, Brockhaus J, Martini R, Sommer C, Zeilhofer H U, Müller W, Kuner R, Davis J B, Rose-John S, Kress M. J. Neurosci. 2009; 29:13473-83; and Obreja O, Schmelz M, Poole S, Kress M. Pain 2002; 96:57-62). This implicates trans-signaling as a possible contributor to discogenic back pain and may indicate the IL-6/sIL-6R/gp130 complex as a primary target for therapeutic development for the treatment of discogenic back pain.

IL-6 induced sensitization in peripheral neuropathy and arthritis models has been observed due to increased phosphorylation of heat-sensitive ion channels, which causes channel activation at lower temperatures, an increased expression of heat-sensitive ion channels in sensitized neurons, or a combination of the two mechanisms. TRPV1 is a heat sensitive ion channel (Caterina M J, Schumacher M A, Tominaga M, Rosen T A, Levine J D, Julius D. Nature 1997; 389:816-24) expressed in nociceptive DRG neurons (Brandao K E, Dell'Acqua M L, Levinson S R. A-kinase anchoring protein 150 expression in a specific subset of TRPV1- and CaV 1.2-positive nociceptive rat dorsal root ganglion neurons. J. Comp. Neurol. 2012; 520:81-99) that has demonstrated involvement in IL-6 induced thermal hyperalgesia in neuropathy models and can be sensitized via phosphorylation by Protein Kinase A (PKA) or Protein Kinase C (PKC) (Jeske N A, Diogenes A, Ruparel N B, Fehrenbacher J C, Henry M, Akopian A N, Hargreaves K M. Pain 2008; 138:604-616; and Jeske N A, Patwardhan A M, Ruparel N B, Akopian A N, Shapiro M S, Henry M A. Pain 2009; 146:301-307). The phosphorylation of TRPV1 by PKA/PKC is regulated by AKAP 150/79 (79 is human and 150 is the rodent analog) (Jeske N A, Diogenes A, Ruparel N B, Fehrenbacher J C, Henry M, Akopian A N, Hargreaves K M. Pain 2008; 138:604-616; and Jeske N A, Patwardhan A M, Ruparel N B, Akopian A N, Shapiro M S, Henry M A. Pain 2009; 146:301-307), a scaffolding protein, that is co-expressed and co-localized with TRPV1 in DRG neurons (Btesh J, Fischer M J M, Stott K, McNaughton P A. J. Neurosci. 2013; 33:9184-93; and Jeske N A, Diogenes A, Ruparel N B, Fehrenbacher J C, Henry M, Akopian A N, Hargreaves K M. Pain 2008; 138:604-616) and mediates TRPV1 phosphorylation by facilitating interactions between PKA/PKC and TRPV1. As a result, the role of TRPV1 sensitization was investigated via phosphorylation by inhibiting AKAP 150 via the inhibitor peptide St-HT31 (Jeske N A, Patwardhan A M, Ruparel N B, Akopian A N, Shapiro M S, Henry M A. Pain 2009; 146:301-307). When blocking the PKA/PKC binding site on AKAP 150 with the inhibitor peptide St-HT31, the observed neuronal thermal sensitivity induced by degenerative IVD was abolished. These results indicated that AKAP150/TRPV1 interaction was required for thermal sensitization of neurons and was the primary mechanism for IL-6 induced sensitization by degenerative IVD. Additionally, the abolition of IL-6 induced thermal sensitization by inhibiting AKAP 150/TRPV1 interaction establishes AKAP 150/79 as a potential therapeutic target in discogenic back pain.

The results show that lentiviral CRISPR epigenome editing of nociceptive neurons inhibits degenerative IVD sensitization to noxious stimuli, particularly heating. CRISPR based epigenome editing allows for the local, long-term, stable site directed gene repression by H3K9 histone methylation. It was hypothesized that degenerative IVD induced sensitization of neurons could be regulated by epigenome editing pain sensitization pathway genes in nociceptive neurons. The data demonstrate that sensory neurons with epigenome modification of AKAP 150 expression in sensory neurons maintained a normal firing response under conditions that sensitize non-edited neurons to noxious stimuli. These results demonstrate epigenome editing of pain related genes in nociceptive neurons regulates sensitization and establishes epigenome modification of pain pathway genes in nociceptive neurons as a therapeutic strategy for discogenic back pain treatment.

In this study, it was demonstrated that pH, at degenerative IVD levels, and degenerative IVD released factors (IL-6) synergistically sensitize TRPV1 channels to fire at sub 38° C. temperatures through the IL6/AKAP/TRPV1 signaling pathway, which would provide a mechanism for nociceptor firing in the degenerative IVD environment. In addition, it was demonstrated that epigenome editing of AKAP expression in sensory neurons prevented degenerative disc environment triggered neuron sensitization to noxious stimuli. These results elucidate a therapeutic target and establish epigenome editing of nociceptive neurons as a treatment strategy for discogenic back pain.

Example 2: CRISPR Based Epigenome Editing of Inflammatory Receptors for the Promotion of Cell Survival and Tissue Deposition in Inflammatory Environments Materials and Methods Plasmids, guide design and cloning. Using the UCSC genome browser (GRCh37/hg19), the 5-UTR and the promoter region, 1000 base pairs upstream were selected and input into the CRISPR design tool (crispr.mit.edu). This tool outputs 20 bp gRNAs that are followed on their 3' end by the PAM sequence NGG, which is specific to the CRISPR-Cas9 system derived from *Streptococcus Pyogenes*. Additionally, the CRISPR design tool scores the potential gRNA sequences based on the number of off-target sites they have and how many are within genes (e.g., higher score means less off-target sites). From this list, the highest scoring gRNAs were input into the BLAT tool of the UCSC genome browser to inspect for overlap of gRNAs with DNAse hypersensitivity peaks, therefore narrowing down potential gRNAs. With these criteria, 5-6 gRNAs were selected for TNFR1 and IL1R1 (Table 3. These selected gRNAs were synthesized (University of Utah peptide synthesis core), annealed, phosphorylated and ligated into hU6-gRNA plasmids at the BbsI sites. For each gene two high performing U6-gRNA cassettes were PCR amplified and transferred into the *S. Pyogenes* dCas9 expressing repression lentiviral vector (hUbC-dCas9-KRAB-T2A-GFP) upstream of the hUbC promoter at the Esp3I sites. An NF-kB reporter plasmid was obtained from Addgene (49343) for experiments assaying NF-kB activity.

TABLE 3

Target sequences for each gene and the control.

| Target Gene | Name | Sequence | SEQ ID NO. |
|---|---|---|---|
| TNFR1 | gRNA 1 | 5'-CAGTGTTGCAACAGCGGGAC-3' | 1 |
| TNFR1 | gRNA 2 | 5'-AGACTCGGGCATAGAGATCA-3' | 2 |
| TNFR1 | gRNA 3 | 5'-GAATGGCAGGCACCCAGTCA-3' | 3 |
| TNFR1 | gRNA 4 | 5'-ATAAGCGTCCGACACATGAT-3' | 4 |
| TNFR1 | gRNA 5 | 5'-GCAAGGGGCTTATTGCCCCT-3' | 5 |
| IL1R1 | gRNA 1 | 5'-GGAGTCGCCAACTCAATTCG-3' | 6 |
| IL1R1 | gRNA 2 | 5'-TGGGGTCCTTGGGCGACTGC-3' | 7 |
| IL1R1 | gRNA 3 | 5'-AGAGGCATTTCCCGGACTCG-3' | 8 |
| IL1R1 | gRNA 4 | 5'-AGCACAAAGTTGGCTGCGCC-3' | 9 |
| IL1R1 | gRNA 5 | 5'-GGGAGGTGACACCCAGTTTA-3' | 10 |
| IL1R1 | gRNA 6 | 5'-AAAGTAGCCTGACGTATCCG-3' | 11 |
| N/A | Nontarget gRNA | 5'-TTTTTAATACAAGGTAATCT-3' | 12 |

TABLE 4

Guide RNA sequences for each gene and the control.

| Target Gene | Name | Sequence | SEQ ID NO. |
|---|---|---|---|
| TNFR1 | gRNA 1 | 5'-CAGUGUUGCAACAGCGGGAC-3' | 79 |
| TNFR1 | gRNA 2 | 5'-AGACUCGGGCAUAGAGAUCA-3' | 80 |
| TNFR1 | gRNA 3 | 5'-GAAUGGCAGGCACCCAGUCA-3' | 81 |
| TNFR1 | gRNA 4 | 5'-AUAAGCGUCCGACACAUGAU-3' | 82 |
| TNFR1 | gRNA 5 | 5'-GCAAGGGGCUUAUUGCCCCU-3' | 83 |
| IL1R1 | gRNA 1 | 5'-GGAGUCGCCAACUCAAUUCG-3' | 84 |
| IL1R1 | gRNA 2 | 5'-UGGGGUCCUUGGGCGACUGC-3' | 85 |
| IL1R1 | gRNA 3 | 5'-AGAGGCAUUUCCCGGACUCG-3' | 86 |
| IL1R1 | gRNA 4 | 5'-AGCACAAAGUUGGCUGCGCC-3' | 87 |
| IL1R1 | gRNA 5 | 5'-GGGAGGUGACACCCAGUUUA-3' | 88 |
| IL1R1 | gRNA 6 | 5'-AAAGUAGCCUGACGUAUCCG-3' | 89 |
| N/A | Nontarget gRNA | 5'-UUUUUAAUACAAGGUAAUCU-3' | 90 |

Cell Culture. HEK293T cells and immortalized hADMSCs were obtained from the American Tissue Collection Center (ATCC). HEK293T cells were cultured in high glucose DMEM (Gibco) supplemented with 10% FBS (Hyclone) and 5 μg/mL gentamicin and subcultured according to manufacturer's instructions. Human ADMSCs were cultured in mesenchymal stem cell basal medium (ATCC, PCS-500-300), supplemented with the ADMSC growth kit (ATCC, PCS-500-40) and 25 μg/mL gentamicin and subcultured according to manufacturer's instructions. All cell cultures were maintained at 37° C. with 5% $CO_2$ with media changed every 2-3 days.

Lentivirus production. Production of lentivirus was performed in HEK293T cells. Prior to plating cells, 6-well culture dishes were pretreated with 0.001% poly-1-lysine for one hour, rinsed 2× with PBS and air dried. Once pretreated dishes were ready, HEK293T cells were plated at a density of 600,000 cells/well in high glucose DMEM (Gibco) supplemented with 10% FBS in 6-well plates. The next day cells were cotransfected with 4 μg of the appropriate lentiviral vector, 3 μg of the packaging plasmid psPAX2 (Addgene, 12260), and 1.2 μg of the envelope plasmid pMD2.G (Addgene, 12259) using lipofectamine 2000. After 16-20 hours the transfection medium was removed and replaced with 2 mL of fresh medium. Supernatant containing lentivirus was collected 24 and 48 hours after removal of transfection medium and filtered through a 0.45 μm PVDF filter. Virus was immediately aliquoted and frozen at −80° C. after filtration until use.

Measurement of regulation of gene expression. Production of stable cell lines. Cells were plated at a density of either 400,000 cells/well (HEK293T cells) or 200,000 cells/well (hADMSCs) in 6-well plates in respective expansion media and allowed to adhere overnight. The next day 1 mL of lentivirus, supplemented with polybrene at a concentration of 8 μg/mL, was placed on cells. After 24 hours virus was removed and washed with PBS 5 times to remove remains of lentivirus. Cells were cultured or frozen down until use. Regarding dCas9-KRAB expressing cells, cells were sorted via flow cytometry using a FACS Aria Cell Sorter to select for GFP positive cells. Cells were cultured or frozen down until use.

Quantitative reverse transcriptase PCR. Total RNA was harvested from cells using Purelink RNA mini kit (Ambion). Purified RNA subsequently digested with amplification grade DNAse I (applied biosystems) according to the manufacturer's protocol and then cDNA synthesis was performed with DNAse I digested RNA using the High-Capacity cDNA Reverse Transcription Kit with RNase Inhibitor (Applied Biosystems, 4374966). Following cDNA synthesis qPCR was formed using Taqman gene expression assays using best coverage primers for each gene (Hs01042313_m1, Hs00991002_m1). Changes in gene expression were expressed as fold changes in mRNA expression relative to the nontarget control, and normalized to GAPDH mRNA expression, using the $\Delta\Delta C_t$ method.

Guide RNA Screening in HEK293T cells. HEK293T cells stably expressing dCas9-KRAB GFP were seeded in 6-well plates at a density of 600,000 cells/well in DMEM-HG with 10% FBS. The following day 2 µg of each gRNA plasmid (one gRNA per well, n=3) was transfected into the cells using lipofectamine 2000 according to manufacturer's instructions. Forty-eight hours post transfection RNA was isolated, DNase I digested and used for cDNA synthesis. Subsequently each sample was then run through taqman qPCR using primers for TNFRSF1A or IL1R1 and housekeeping gene GAPDH to quantify downregulation of each gene by each guide. Gene downregulation was quantified using the $\Delta\Delta$Ct method to characterize fold change relative to non-target gRNA expressing cells.

Measurement of functional effects of epigenome editing based gene downregulation. NE-κB activity assays. HEK293T cells and hADMSCs were transduced with the earlier mentioned NF-κB reporter vector and analyzed for changes in NF-κB activity in response to dosing cells with TNF-α/IL-1β (RnD systems, ProSpec). To further describe, cells expressing the NF-κB reporter were plated in white 96-well plates (HEK293T cells at 25,000 cells/well and hADMSCs at 5000 cells/well) and allowed to attach overnight. The next day cells were dosed with the appropriate amounts of inflammatory cytokines (0, 150, 1, and/or 10 ng/mL of TNF-α/IL-1β) for 24 hours. At 24 hours luminescence corresponding to NF-κB activity was measured in one set of cells using the bright glo assay (Promega) and cell number was measured on another set of cells under the same treatment using the real-time glo assay (Promega). Changes in NF-κB activity were quantified as a fold change in luminescence relative to the no dose control for each cell type, with NF-κB activity normalized to cell number.

Three dimensional culture under inflammatory conditions. Human ADMSCs were cultured in pellet cultures within the presence of TNF-α/IL-1β to observe matrix production and cell proliferation under inflammatory conditions. Three dimensional culture media consisted of DMEM-HG (thermofisher), insulin (5 µg/mL), transferrin (5 µg/mL), selenous acid (5 ng/mL), 1.25 mg/mL BSA, 0.17 mM ascorbic acid 2-phosphate, 0.35 mM proline, 0.1 m dexamethasone, 10 ng/mL TGFβ-3 (ProSpec) and 1% antibiotic/antimycotic (unless specified all reagents were purchased from Sigma). To create cell pellets, cells were trypsinized, resuspended at a density of $1\times10^6$ cells/mL, and 200 µL aliquots were placed in single wells within a polypropylene v-bottom plate and spun at 1000 g for five minutes to create pellets at the bottom of each well. Pellets formed and lifted after 24 hours at which media was replaced and dosing with TNF-α/IL-1β was begun. Pellets were cultured for 28 days with media changed every 3 days after which pellets were either fixed in 10% NBF or frozen at −80° C. until analysis.

Size analysis. Prior to pulling pellets for analysis, pellets were imaged while still in wells. Images were used to perform cross sectional area analysis of pellets in ImageJ (imagej.nih.gov/ij/). Cross sectional area measurements were converted from pixel$^2$ to mm$^2$ using a reference object of known size.

Chondrogenesis under Inflammatory Conditions. Human ADMSCs were differentiated in pellet cultures dosed with TNF-α or IL-1β to investigate ability to undergo chondrogenesis under inflammatory conditions. Basal chondrogenic media consisted of DMEM-HG (thermofisher), 1×ITS+ premix (Corning), 0.1 µM dexamethasone, 0.17 mM, 0.35 mM ascorbic acid 2-phosphate, 1× antibiotic antimycotic solution (unless specified all reagents were purchased from Sigma). To create complete differentiation media, basal chondrogenic media was supplemented with 10 ng/mL of TGFβ-3 and BMP-6 (Peprotech). To create chondrogenic pellets, cells were trypsinized, resuspended in basal chondrogenic media at density of $1.25\times10^6$ cells/mL and 200 µL aliquots (250,000 cells) were placed in single wells within a polypropylene v-bottom plate (Corning) and spun at 1000 g for five minutes to create pellets at the bottom of each well. Pellets formed and lifted after 24 hours after which media was replaced with complete chondrogenic media with added TNF-α/IL-1β to respective wells. Pellets were cultured for 21 days with media replaced every 3 days after which pellets were either fixed in 10% NBF or lyophilized and frozen at −80° C. until analysis. Spent media was collected at each media change for analysis of glycosaminoglycan (GAG) content released.

DNA and Glycosaminoglycan Quantification. Pellet cultures were analyzed for DNA and GAG content. Prior to analysis samples were papain digested at 60° C. for 12-16 hours in 0.125 µg/mL papain in 0.10 M Na$_2$HPO$_4$, 0.010 M Na$_2$EDTA, and 0.01 M L-cysteine hydrochloride (pH 6.5). DNA content was then measured using the Hoechst 33258 assay. Briefly, digested sample was added to Hoechst dye solution (0.1 µg/mL of Hoechst 33258 in 10 mM Tris, 1 mM disodium EDTA, and 0.1 mM NaCl at pH 7.4) and fluorescence was measured on a Biotek Synergy HTX plate reader. DNA concentration was based on standard curves made using calf thymus DNA (Sigma). Glycosaminoglycan content of the papain digested pellets was analyzed using the DMMB assay as previously described (Zheng and Levenston, 2015). Briefly samples were added to DMMB solution (pH 1.5) and the absorbance was measured at 525 and 595 nm and the OD$_{525-595}$ was used to determine concentration. Concentration was based on standard curves were made using shark chondroitin-6-sulfate (Sigma).

Histology. Samples were fixed in 10% NBF for 48 hours and then transferred to 70% EtOH and taken to the University of Utah histology core for further processing and embedding. Samples were paraffin embedded and 5 µm sections were mounted onto charged slides. Samples were rehydrated and stained with H & E to characterize matrix production. Slides were imaged using light microscopy (Nikon Eclipse E400, Olympus UC50 Camera) to visualize sample variability under multiple conditions.

Characterization of Immunomodulatory Properties of Engineered ADMSCs. To investigate immunomodulatory properties of engineered hADMSC lines, their suppressive effect on phytohemagglutinin (PHA) activated PBMCs in co-culture was characterized. Prior to co-culture hADMSCs were Mitomycin C treated (10 µg/mL) for 2 hours at 37° C.

After treatment hADMSCs were rinsed 2× with PBS, trypsinized and plated at a density of 12,800 cells/well in a 96-well plate in RPMI1640 media (thermofisher) supplemented with 10% FBS and 100 U/mL penicillin, and 0.1 mg/mL streptomycin. The following day PBMCs (ATCC) were added at a density of 102,400 cells/well (1:8 hADMSC:PBMC ratio) and active with 5 μg/mL PHA. After two days of coculture EdU was added at a concentration of 10 μM and after 18 hours PBMCs were harvested for analysis. To analyze proliferation PBMCs were CD45 stained (BD biosciences) and EdU labeled with the Click-iT EdU flow cytometry kit (thermofisher) according to manufacturer's instructions. The amount of EdU positive CD45 labeled PBMCs were characterized by flow cytometry to provide a quantitative measurement of proliferation compared to the control of PBMCs cultured alone.

Statistical analysis. Experiments characterizing efficiency of gRNAs in downregulating gene expression were analyzed by one-way analysis of variance (ANOVA) with Tukey's post hoc test, treating different gRNAs as factors. Experiments looking at changes in NF-κB activity, pellet size, DNA content and GAG content were analyzed by two-way ANOVA with Tukey's post hoc test, treating different cell types and cytokine dose as factors. Experiments investigating immunosuppressive effects were analyzed by one-way analysis of variance (ANOVA) on repeated measures with Tukey's post hoc test, treating different types of hADMSCs as factors.

Results. Epigenome editing of TNFR1 in HEK293T cells efficiently downregulates NF-κB activity. Designed gRNAs were initially tested in HEK293T cells to screen for the most efficient gRNAs and provide proof of concept in signaling regulation. Screening of 5-6 gRNAs for both TNFR1 and IL1R1 demonstrated efficient gene downregulation by multiple gRNAs (FIG. 7) with up to 87% gene downregulation by gRNA 1 for TNFR1 and 67% gene downregulation by gRNA 1 for IL1R1. Downregulation of TNFR1 signaling by gRNA 1, measured after 24 hours of dosing with 0, 0.15, 1, and 10 ng/mL of TNF-α demonstrated effective inhibition of TNFR1 signaling. This was noted by significant decreases in NF-κB activity (up to 95%) with no significant increase in NF-κB activity at the lowest most physiologically relevant dose of 0.15 ng/mL.

Epigenome Editing of TNFR1 and IL1R1 in hADMSCs Downregulates NF-κB Activity. Testing for gene downregulation by two gRNAs, verified to be efficient in HEK293T cells, in hADMSCs demonstrated up to 90% and 88% gene downregulation of TNFR1 and IL1R1, respectively, thus, demonstrating efficient epigenome editing across multiple cell types (FIG. 8). Of note, efficiency by gRNAs flipped for IL1R1 in comparison to data shown in HEK293T cells; therefore, demonstrating how small genetic differences in the promoter sites can have a large effect on the efficacy of gene regulation.

Measurement of NF-κB activity post cytokine dosing in hADMSCs demonstrated potent downregulation of TNFR1 signaling, with no significant increase in NF-κB activity noted at both doses of TNF-α (FIG. 8). Downregulation in signaling of IL1R1 was present but not as potent, while significant NF-κB activity was decreased at the 0.15 ng/mL dose of IL-1β (40% decrease, FIG. 8). Overall regulation of signaling was present in these cells, therefore, demonstrating regulation of TNFR1 and IL1R1 at signaling level and not just at the gene level.

TNFR1 IL1R1 epigenome editing protects hADMSCs from an inflammatory environment. Three dimensional culture of hADMSCs in the presence of TNF-α and IL-1β, demonstrated overall cell protection when the cytokine's respective receptor was downregulated. Measurement of cell pellet cross sectional area demonstrated the maintenance of size in TNFR1/IL1R1 edited vs non-target edit cells, therefore, indicating protection from matrix breakdown (FIG. 9). H & E staining of cell pellets further demonstrated this with lighter background staining in non-target edit control hADMSCs pellets dosed with IL-1β/TNF-α (FIG. 9). Additionally, examining DNA content relative to control, TNFR1 edited cells demonstrated significantly improved maintenance of DNA content compared to nontarget edit cells (FIG. 9).

When induced to undergo chondrogenic differentiation by TGFβ3 and BMP-6, both edited and unedited cells underwent chondrogenic differentiation as noted by significant amounts of measured GAG content. When dosed with either TNF-α or IL-1 in chondrogenic media, chondrogenesis was inhibited in naïve and non-target edit control hADMSCs as noted by significant decreases in GAG content relative to undosed controls (FIG. 10). Looking specifically at GAG/pellet, significant decreases were seen in all samples but the decrease was less in TNFR1 edited cells. When observing GAG within spent media TNFR1 edited cells did not show a significant decrease in GAG released while all other cell types did. Observing total GAG content, TNFR1 edited cells showed no significant decrease in overall GAG content whereas all other cell types did. Therefore this data indicates that epigenome editing based downregulation TNFR1 expression allows hADMSCs to differentiate in an environment with elevated levels of TNF-α while IL1R1 downregulation still allows IL-1β to have an inhibitory effect on chondrogenesis.

Immunomodulatory properties of hADMSCs are maintained post epigenome editing. Co-culture of hADMSCs with PBMCs demonstrated that therapeutic immunomodulatory properties of these stem cells are maintained after epigenome editing (FIG. 11). Relative to naïve untransduced hADMSCs, PBMCs cultured with TNFR1 edited hADMSCs showed no significant increase in proliferation therefore indicating that immunomodulatory properties are well maintained. PBMCs cultured with IL1R1 edited hADMSCs showed a slight but significant decrease in suppression of PBMC proliferation therefore indicating a decrease in immunomodulation. Overall, there was still a 40% decrease in PBMC proliferation by IL1R1 edited hADMSCs relative to PBMCs alone; therefore, beneficial immunomodulatory properties are still present.

Example 3: Investigating CRISPi Cell-Engineering Methods for Treatment of Intervertebral Disc Degeneration Methods. CRISPRi Vector Design. Sequences for gRNAs for the TNFR1 and IL1R1 promoter region of each gene were selected along with an adjacent protospacer adjacent motif (crispr.mit.edu). A non-targeting gRNA was chosen as a control. Each gRNA was cloned into a plasmid under the control of the U6 promoter. To screen the gRNAs for the best knockdown, gRNA plasmids were transfected into a Human Embryonic Kidney (HEK293T) cell line stably expressing dCas9-KRAB (Lipofectamine 2000, n=3 per guide). Forty-eight hours post-transfection, RNA was isolated and quantitative reverse transcriptase PCR (qRT-PCR) was performed for TNFR1, IL1R1, and GAPDH. For TNFR1, the gRNA showing the greatest knockdown was cloned into two different lentiviral vectors, resulting in the co-expression of the gRNA with dCas9-T2A-GFP or dCas9-KRAB-T2AGFP from a single lentiviral vector.

Human NP Cell CRISPRi. Human nucleus pulposus (NP) cells were obtained from a 51-year-old male discectomy patient and transduced with the TNFR1 lentiviral CRISPRi vectors along with a control lentiviral vector that did not express a gRNA. Quantitative RT-PCR was performed to identify TNFR1 knockdown in these primary human NP cells. Additionally, flow-cytometry was performed to determine transduction efficiency in human NP cells.

Functional TNFRJ Knockdown. Functional knockdown of TNFR1 was studied by quantifying TNF-α induced NF-KB activity after CRISPRi knockdown. NF-KB activity was quantified using a firefly luciferase NF-KB reporter vector that was transduced into HEK293T cells (Bowles R D, Karikari I O, VanDerwerken D N, Sinclair M S, Bell R D, Riebe K J, Huebner J L, Kraus V B, Sempowski G D, Setton L A. In vivo luminescent imaging of NF-κB activity and NF-κB-related serum cytokine levels predict pain sensitivities in a rodent model of peripheral neuropathy. Eur. J. Pain 2015). NF-KB reporter expressing HEK293T cells were also transduced with the developed TNFR1 lentiviral CRISPRi vector and cell sorted for GFP to produce a cell line expressing the TNFR1 CRISPRi system. These cells along with the non-knockdown cells were seeded at 25,000 cells/well in white opaque plates and treated with either 0 ng/ml, 150 µg/ml, 1 ng/ml, and 10 ng/ml rhTNF-α, for 24 hours (n=5 per treatment). NF-KB activity was then measured using a firefly luciferase luminescence assay (Bright-Glo, Promega). Additionally, cell number was assayed (RealTime-Glo, Promega) on a separate plate with the same experimental conditions, therefore allowing for normalization of each NF-KB luminescence signal to the number of viable cells. Luminescence for both assays was measured using a synergy HTX biotek plate reader. Activity of NF-KB is reported as a fold change relative to control and normalized by cell viability.

Statistical Analysis. To determine if knockdown of IL1R1 and TNFR1 in HEK293T cells was statistically significant, a one-way ANOVA was conducted with Tukey post hoc. For statistical analysis of NF-KB activity, a two-way ANOVA with Tukey post hoc was conducted and a p<0.05 was considered statistically significant.

Results. CRISPRi Vector Design. Quantitative reverse transcriptase PCR studies for both TNFR1 and IL1R1 in HEK293T cells show significant knockdown in four out of five guides for TNFR1 and two out of seven guides for IL1R1. Maximum knockdown in the guides screened was 82% for TNFR1 and 67% for IL1R1 (FIG. 12A-B). Using gRNA 4 for TNFR1 with dCas9-KRAB, 55% TNFR1 knockdown was observed in NP cells but no knockdown with dCas9 alone (FIG. 13B). Transduction efficiency of TNFR1 lentiviral CRISPRi vector in human NP cells was 42%.

Functional TNFR1 Knockdown. Fold change in NF-KB activity was significantly decreased in response to TNF-α after TNFR1 CRISPRi knockdown at each TNF-α dose, demonstrating a decrease in TNFR1 induced signaling (FIG. 13). The decrease in activity was on the order of −95% for the two highest doses and returned the lowest dose to baseline levels. These results indicate a complete elimination of this deleterious signaling pathway at the most physiologically relevant dose.

Discussion. These studies show that CRISPRi knockdown of inflammatory receptors can be used to modulate the inflammatory response relevant to disc pathology. These results also show that CRISPRi can be used to significantly reduce gene expression of TNFR1 and IL1R1 in HEK293T cells and TNFR1 gene expression in human NP cells (FIGS. 12 and 13). The results also show that this measured reduction in TNFR1 gene expression also results in a loss of TNFR1 signaling, as demonstrated by the significantly lower fold change in NF-KB activity in TNFR1 knockdown versus number of knockdown cells for each TNF-α dose (FIG. 14). This finding relates to disc pathology, as NF-KB signaling has been identified as a component in the degenerative process and antagonizing NF-KB activity has shown therapeutic effects in preclinical animal models. The data also shows that TNFR1 CRISPRi was able to return the physiologically relevant dose (150 µg/ml) to baseline levels. Despite the 42% transduction efficiency, the CRISPRi system showed expression and activity in human primary NP cells, making their application to the disc a possibility. Methods to improve transduction efficiency in the primary human NP cells and the ability of this system to promote viable tissue formation in the inflammatory environment in the degenerative IVD can also be investigated. These data show a step in developing and applying the CRISPRi dCas9 system to disc pathology, which can be used for both gene therapy applications and tissue engineering applications targeting DOD.

REFERENCES

Kokubo Y, Uchida K, Kobayashi S, Yayama T, Sato R, Nakajima H, Takamura T, Mwaka E, Orwotho N, Bangirana A, Baba H. Herniated and spondylotic intervertebral discs of the human cervical spine: histological and immunohistological findings in 500 en bloc surgical samples. Laboratory investigation. J. Neurosurg. Spine 2008; 9:285-95.

Cabal-Hierro L, Lazo P S. 2012, Signal transduction by tumor necrosis factor receptors, *Cell Signal*, 24: 1297-305.

Chun H J, Kim Y S, Kim B K, Kim E H, Kim J H, Do B R, Hwang S J, Hwang J Y, Lee Y K. 2012, Transplantation of human adipose-derived stem cells in a rabbit model of traumatic degeneration of lumbar discs, *World Neurosurg*, 78: 364-71.

Gilbert L A, Horlbeck M A, Adamson B, Villalta J E, Chen Y, Whitehead E H, Guimaraes C, Panning B, Ploegh H L, Bassik M C, Qi L S, Kampmann M, Weissman J S. 2014, Genome-Scale CRISPR-Mediated Control of Gene Repression and Activation, *Cell*, 159: 647-661.

Heldens G T H, Blaney Davidson E N, Vitters E L, Schreurs B W, Piek E, van den Berg W B, van der Kraan P M. 2012, Catabolic factors and osteoarthritis-conditioned medium inhibit chondrogenesis of human mesenchymal stem cells, *Tissue Eng Part A*, 18: 45-54.

Hoy D, Bain C, Williams G, March L, Brooks P, Blyth F, Woolf A, Vos T, Buchbinder R. 2012, A systematic review of the global prevalence of low back pain, *Arthritis Rheum*, 64: 2028-2037.

Von Korff M, Saunders K. 1996, The course of back pain in primary care, *Spine (Phila Pa.* 1976), 21: 2833-7; discussion 2838-9.

Larson M H, Gilbert L A, Wang X, Lim W A, Weissman J S, Qi L S. 2013, CRISPR interference (CRISPRi) for sequence-specific control of gene expression, *Nat Protoc*, 8: 2180-96.

Liang C, Li H, Tao Y, Zhou X, Li F, Chen G, Chen Q. 2012, Responses of human adipose-derived mesenchymal stem cells to chemical microenvironment of the intervertebral disc, *J Transl Med*, 10: 49.

Luoma K, Riihimäki H, Luukkonen R, Raininko R, Viikari-Juntura E, Lamminen A. 2000, Low back pain in relation to lumbar disc degeneration, *Spine (Phila Pa. 1976)*, 25: 487-92.

Le Maitre C L, Hoyland J A, Freemont A J. 2007, Catabolic cytokine expression in degenerate and herniated human intervertebral discs: IL-1beta and TNFalpha expression profile, *Arthritis Res Ther*, 9: R77.

Marfia G, Campanella R, Navone S E, Zucca I, Scotti A, Figini M, Di Vito C, Alessandri G, Riboni L, Parati E. 2014, Potential use of human adipose mesenchymal stromal cells for intervertebral disc regeneration: a preliminary study on biglycan-deficient murine model of chronic disc degeneration, *Arthritis Res Ther*, 16: 457.

Millward-Sadler S J, Costello P W, Freemont A J, Hoyland J A. 2009, Regulation of catabolic gene expression in normal and degenerate human intervertebral disc cells: implications for the pathogenesis of intervertebral disc degeneration, *Arthritis Res Ther*, 11: R65.

Murray C J L, Lopez A D. 2013, Measuring the global burden of disease, *N Engl J Med*, 369: 448-57.

Orozco L, Soler R, Morera C, Alberca M, Sánchez A, García-Sancho J. 2011, Intervertebral disc repair by autologous mesenchymal bone marrow cells: a pilot study, *Transplantation*, 92: 822-8.

Pettine K, Suzuki R, Sand T, Murphy M. 2016, Treatment of discogenic back pain with autologous bone marrow concentrate injection with minimum two year follow-up, *Int Orthop*, 40: 135-40.

Purmessur D, Walter B A, Roughley P J, Laudier D M, Hecht A C, Iatridis J. 2013, A role for TNFα in intervertebral disc degeneration: a non-recoverable catabolic shift, *Biochem Biophys Res Commun*, 433: 151-6.

Strassburg S, Richardson S M, Freemont A J, Hoyland J A. 2010, Co-culture induces mesenchymal stem cell differentiation and modulation of the degenerate human nucleus pulposus cell phenotype, *Regen Med*, 5: 701-11.

Studer R K, Vo N, Sowa G, Ondeck C, Kang J. 2011, Human nucleus pulposus cells react to IL-6: independent actions and amplification of response to IL-1 and TNF-α, *Spine (Phila Pa. 1976)*, 36: 593-9.

Tam V, Rogers I, Chan D, Leung V Y L, Cheung K M C. 2014, A comparison of intravenous and intradiscal delivery of multipotential stem cells on the healing of injured intervertebral disk, *J Orthop Res*, 32: 819-25.

Thakore P I, D'Ippolito A M, Song L, Safi A, Shivakumar N K, Kabadi A M, Reddy T E, Crawford G E, Gersbach C A. 2015, Highly specific epigenome editing by CRISPR-Cas9 repressors for silencing of distal regulatory elements, *Nat Methods*, 12: 1143-1149.

Wang Y, Chen X, Cao W, Shi Y. 2014, Plasticity of mesenchymal stem cells in immunomodulation: pathological and therapeutic implications, *Nat Immunol*, 15: 1009-16.

Wehling N, Palmer G D, Pilapil C, Liu F, Wells J W, Müller P E, Evans C H, Porter R M. 2009, Interleukin-1beta and tumor necrosis factor alpha inhibit chondrogenesis by human mesenchymal stem cells through NF-kappaB-dependent pathways, *Arthritis Rheum*, 60: 801-12.

Weiler C, Nerlich A G, Bachmeier B E, Boos N. 2005, Expression and distribution of tumor necrosis factor alpha in human lumbar intervertebral discs: a study in surgical specimen and autopsy controls, *Spine (Phila Pa. 1976)*, 30: 44-53; discussion 54.

Wuertz K, Godburn K, Neidlinger-Wilke C, Urban J, Iatridis J C. 2008, Behavior of mesenchymal stem cells in the chemical microenvironment of the intervertebral disc, *Spine (Phila Pa. 1976)*, 33: 1843-9.

Zheng C H, Levenston M E. 2015, Fact versus artifact: avoiding erroneous estimates of sulfated glycosaminoglycan content using the dimethylmethylene blue colorimetric assay for tissue-engineered constructs, *Eur Cell Mater*, 29: 224-36; discussion 236.

Example 4: Regulating Stem Cell Phenotype Using CRISPR Epigenome Editing

Introduction: There is interest in stem cell application to musculoskeletal tissue engineering and cell therapies. However, the success of these strategies is limited, as stem cells implanted into challenging disease environments struggle to maintain an exemplary phenotype. Regulating the phenotype of stem cells has largely been accomplished by controlled growth factor treatment. Disclosed herein is a method for controlling cell phenotype without growth factors by utilizing targeted CRISPR epigenome editing. These CRISPR-Cas systems perform specific gene upregulation through targeted histone acetylation at regulatory elements via a guide RNA (gRNA)/dCas9-p300 core complex. Using this system, genes specific to desired phenotypes can be regulated. In this study this system is used to upregulate aggrecan (ACAN), type II collagen (COL2A1), interleukin 10 (IL-10), and indoleamine 2,3-dioxygenase 1 (IDO1) to engineer stem cells with enhanced musculoskeletal tissue regenerative/anti-inflammatory properties that allow them to better thrive in their applied disease environments.

Methods: Guide RNAs targeting promoters for genes of interest (ACAN, COL2A1, IL10, IDO1; see, Tables 5 and 6) and a scrambled nontarget gRNA control were designed and cloned into lentiviral vectors. Subsequently, each gRNA vector, a tetracycline-inducible dCas9-p300 core vector, and a reverse tetracycline-controlled transactivator vector, were transduced into human adipose-derived stem cells (hADSCs) to deliver a complete tetracycline-inducible CRISPR epigenome-editing system. To test the ability of this system to upregulate target genes, hADSCs were dosed with tetracycline (doxycycline hyclate, 3 µg/mL) for 7 days and target gene expression was measured by qRT-PCR (n=3, One-way ANOVA, Dunnett's post hoc). Cells containing the best-performing gRNAs for ACAN were then cultured in chondrogenic pellet cultures with or without TGFβ3 and BMP-6 for 21 days, to investigate the ability of this gene regulation to enhance chondrogenesis. These cultures were qualitatively analyzed for sulfated glycosaminoglycan (sGAG) content by Alcian Blue staining (n=3) and quantitatively analyzed for sGAG content by the dimethyl methylene blue (DMMB) assay (n=5-9, two-way ANOVA, Tukey post-hoc).

TABLE 5

Examples of Target Sequences

| Target Gene | Name | Sequence | SEQ ID NO. |
|---|---|---|---|
| IDO1 | gRNA 1 | 5'-TTATGACTACATGATTCATG-3' | 91 |
| IDO1 | gRNA 2 | 5'-AATTAAATTGTGATAGCATA-3' | 92 |
| IDO1 | gRNA 3 | 5'-TTCTCCTTTTGATCATCTAG-3' | 93 |
| IDO1 | gRNA 4 | 5'-ATAACACAGGTTGTGTTTCC-3' | 94 |
| IDO1 | gRNA 5 | 5'-TAAAGTAAAATGTTCTTCTC-3' | 95 |
| IDO1 | gRNA 6 | 5'-GATGCACAGAGATGCTTTTG-3' | 96 |

TABLE 5-continued

Examples of Target Sequences

| Target Gene | Name | Sequence | SEQ ID NO. |
|---|---|---|---|
| IL10 | gRNA 1 | 5'-GTGCCGGGAAACCTTGATTG-3' | 97 |
| IL10 | gRNA 2 | 5'-CAATCAAGGTTTCCCGGCAC-3' | 98 |
| IL10 | gRNA 3 | 5'-GAAAACTAAGTTTATTAGAG-3' | 99 |
| IL10 | gRNA 4 | 5'-GCATCGTAAGCAAAAATGAT-3' | 100 |
| IL10 | gRNA 5 | 5'-ATTACAGCTATTTTTAGGAT-3' | 101 |
| ACAN | gRNA 1 | 5'-CGGGTCTCGCTGCGTAGCGA-3' | 102 |
| ACAN | gRNA 2 | 5'-GACGCGCGCAGCGCTGCTCA-3' | 103 |
| ACAN | gRNA 3 | 5'-ACATACATAGGGACGGGCGG-3' | 104 |
| ACAN | gRNA 4 | 5'-GACCGAGGGGCGGCCGACAG-3' | 105 |
| ACAN | gRNA 5 | 5'-CTCCGGACCGGCGCGCCGAT-3' | 106 |
| ACAN | gRNA 6 | 5'-GCCCGCATCTGCATTGCGGT-3' | 107 |
| ACAN | gRNA 7 | 5'-GGCCACGACGCGATCTAAGG-3' | 108 |
| ACAN | gRNA 8 | 5'-TTTTTGGGGTGGCGTACAC-3' | 109 |
| ACAN | gRNA 9 | 5'-TTGGCTCAGTCACCGCCGGC-3' | 110 |
| ACAN | gRNA 10 | 5'-ATTTCAGCAACTCTCGCCCG-3' | 111 |
| COL2A1 | gRNA 1 | 5'-CGCTCCCTAGCACGTGGTGC-3' | 112 |
| COL2A1 | gRNA 2 | 5'-CATTGGGAGATTGGCAGCGA-3' | 113 |
| COL2A1 | gRNA 3 | 5'-GTCAGCAGCACCAGCGTCTG-3' | 114 |
| COL2A1 | gRNA 4 | 5'-GCGGAGCGCAGCGAAACGGC-3' | 115 |
| COL2A1 | gRNA 5 | 5'-CTACCGCGCCCTCATGCAGG-3' | 116 |
| COL2A1 | gRNA 6 | 5'-GGGTCCGGCTTGGGCAGGTG-3' | 117 |
| COL2A1 | gRNA 7 | 5'-AACTCCGGCAGAACTCCGAG-3' | 118 |
| COL2A1 | gRNA 8 | 5'-GCGGTAGAAAGGAGCAGCGG-3' | 119 |

TABLE 6

Examples of Guide RNA Sequences (gRNAs)

| Target Gene | Name | Sequence | SEQ ID NO. |
|---|---|---|---|
| IDO1 | gRNA 1 | 5'-UUAUGACUACAUGAUUCAUG-3' | 120 |
| IDO1 | gRNA 2 | 5'-AAUUAAAUUGUGAUAGCAUA-3' | 121 |
| IDO1 | gRNA 3 | 5'-UUCUCCUUUUGAUCAUCUAG-3' | 122 |
| IDO1 | gRNA 4 | 5'-AUAACACAGGUUGUGUUCC-3' | 123 |
| IDO1 | gRNA 5 | 5'-UAAAGUAAAAUGUUCUUCUC-3' | 124 |
| IDO1 | gRNA 6 | 5'-GAUGCACAGAGAUGCUUUUG-3' | 125 |
| IL10 | gRNA 1 | 5'-GUGCCGGGAAACCUUGAUUG-3' | 126 |
| IL10 | gRNA 2 | 5'-CAAUCAAGGUUUCCCGGCAC-3' | 127 |
| IL10 | gRNA 3 | 5'-GAAAACUAAGUUUAUUAGAG-3' | 128 |
| IL10 | gRNA 4 | 5'-GCAUCGUAAGCAAAAAUGAU-3' | 129 |
| IL10 | gRNA 5 | 5'-AUUACAGCUAUUUUUAGGAU-3' | 130 |
| ACAN | gRNA 1 | 5'-CGGGUCUCGCUGCGUAGCGA-3' | 131 |
| ACAN | gRNA 2 | 5'-GACGCGCGCAGCGCUGCUCA-3' | 132 |
| ACAN | gRNA 3 | 5'-ACAUACAUAGGGACGGGCGG-3' | 133 |
| ACAN | gRNA 4 | 5'-GACCGAGGGGCGGCCGACAG-3' | 134 |
| ACAN | gRNA 5 | 5'-CUCCGGACCGGCGCGCCGAU-3' | 135 |
| ACAN | gRNA 6 | 5'-GCCCGCAUCUGCAUUGCGGU-3' | 136 |
| ACAN | gRNA 7 | 5'-GGCCACGACGCGAUCUAAGG-3' | 137 |
| ACAN | gRNA 8 | 5'-UUUUUGGGGUGGCGUACAC-3' | 138 |
| ACAN | gRNA 9 | 5'-UUGGCUCAGUCACCGCCGGC-3' | 139 |
| ACAN | gRNA 10 | 5'-AUUUCAGCAACUCUCGCCCG-3' | 140 |
| COL2A1 | gRNA 1 | 5'-CGCUCCCUAGCACGUGGUGC-3' | 141 |
| COL2A1 | gRNA 2 | 5'-CAUUGGGAGAUUGGCAGCGA-3' | 142 |
| COL2A1 | gRNA 3 | 5'-GUCAGCAGCACCAGCGUCUG-3' | 143 |
| COL2A1 | gRNA 4 | 5'-GCGGAGCGCAGCGAAACGGC-3' | 144 |
| COL2A1 | gRNA 5 | 5'-CUACCGCGCCCUCAUGCAGG-3' | 145 |
| COL2A1 | gRNA 6 | 5'-GGGUCCGGCUUGGGCAGGUG-3' | 146 |
| COL2A1 | gRNA 7 | 5'-AACUCCGGCAGAACUCCGAG-3' | 147 |
| COL2A1 | gRNA 8 | 5'-GCGGUAGAAAGGAGCAGCGG-3' | 148 |

Results: These CRISPR epigenome-editing systems (e.g., CRISPR-Cas systems) were used to robustly upregulate the targeted genes with up to 606, 3.5, 376, and 112 fold increases in IL10, IDO1, COL2A1, and ACAN respectively (FIGS. 20 and 21). Alcian blue staining and DMMB assay of ACAN-edited cultures (FIG. 24 and FIG. 23, left) demonstrate enhanced sGAG production with and without growth factors. ACAN-edited groups showed up to a 14-fold increase in sGAG over traditional growth factor dosed pellets. Interestingly, it was observed in the histology and measurements of percent sGAG retained within the pellet (FIG. 25 and FIG. 23, right), to drive a better chondrogenic phenotype (lacunae and sGAG retention) in ACAN edited pellets, growth factors were still needed.

Discussion: These results indicate that CRISPR epigenome editing can upregulate genes beneficial to cell function within the pathological musculoskeletal tissue they are to be implanted into. These CRISPR-Cas systems were able to upregulate genes relevant to cartilaginous tissue generation (ACAN and Col2A1), and immunomodulation (IL10 and IDO1) therefore demonstrating an ability to modulate genes that are useful for enhancing extracellular matrix production and resistance to inflammatory environments. These pellet cultures verified that ACAN edits can enhance sGAG deposition without exogenous growth factors and can induce sGAG deposition better than traditional growth factor differentiation. This signifies that this ACAN gene upregulation can potentially regulate and enhance the phenotype of stem cells without the use of growth factors and in challenging environments. However, addition of growth factors did improve chondrogenic phenotype and pellet sGAG retention.

Significance/Clinical Relevance: Overall this data indicates an ability to regulate cell phenotype through tetracycline-inducible CRISPR epigenome-editing systems in hADSCs to improve chondrogenic potential and anti-inflammatory properties in these cells. Multiplex gene regulation using these systems will provide a wide range of control over these cells to enhance stem cell therapies.

Example 5: CRISPRa-Driven Collagen II & Aggrecan Deposition Drives a Chondrogenic Phenotype without Exogenous Growth Factors Abstract. Stem cell therapies have come about as a regenerative approach to treating musculoskeletal conditions but their success is mixed. To enhance regenerative effects, growth factors are utilized to induce differentiation into native cell types, but uncontrollable in vivo conditions inhibit this differentiation and precise control of expressed matrix proteins isn't achieved. To address these issues, a method of enhancing regenerative phenotype through direct upregulation of major cartilaginous tissue proteins, aggrecan (ACAN) and collagen II (COL2A1) using dCas9-VPR CRISPR gene activation systems was developed and investigated. The results demonstrate increased expression and deposition of targeted proteins independent of exogenous growth factors in pellet culture. Singular upregulation of COL2A1/ACAN surprisingly indicated that COL2A1 upregulation mediates highest sGAG deposition in addition to expected collagen II deposition. Through RNA-seq analysis this was indicated to occur due to COL2A1 upregulation mediating broader gene expression changes in pellet culture. Upregulation COL2A1 and ACAN together resulted in highest sGAG and collagen II deposition, with levels comparable to those seen in chondrogenic growth factor differentiated pellets. Overall, this work indicates dCas9-VPR systems can robustly upregulate COL2A1 and ACAN deposition independent of growth factors, to provide a precise method of controlling stem cell phenotype and enhancing their regenerative capability.

Introduction. Musculoskeletal disease ranks second in years lived with disability, making it a major healthcare concern (Vos, T. et al. The Lancet 390, (2017)). The most common musculoskeletal diseases are osteoarthritis and low back pain (LBP) and current treatments for these are palliative (Von Korff, M. & Saunders, K. Spine (Phila. Pa. 1976). 21, 2833-7; discussion 2838-9 (1996); Rosemann, T. et al. BMC Musculoskelet. Disord. 7, 48 (2006); and Yazdany, J. & MacLean, C. H. Curr. Opin. Rheumatol. 20, 159-166 (2008)). One major characteristic that describes musculoskeletal tissue degeneration is a loss of tissue components which support tissue mechanical function. Major ECM proteins which decrease include aggrecan and type II collagen (Maldonado, M. & Nam, J. BioMed Research International 2013, 284873 (2013); and Adams, M. A. & Roughley, P. J. What is intervertebral disc degeneration, and what causes it? Spine (Phila. Pa. 1976). 31, 2151-61 (2006)). In an effort restore and regenerate musculoskeletal tissue, cell therapies are being developed (Jevotovsky, D. S., Alfonso, A. R., Einhorn, T. A. & Chiu, E. S. Osteoarthr. Cartil. 26, 711-729 (2018); and Wang, F., Shi, R., Cai, F., Wang, Y. T. & Wu, X. T. Stem Cells Dev. 24, 2479-2495 (2015)). Several cell therapy treatments have been developed for treatment of osteoarthritis and LBP and are being used and/or tested clinically (Jevotovsky, D. S., Alfonso, A. R., Einhorn, T. A. & Chiu, E. S. Osteoarthr. Cartil. 26, 711-729 (2018); and Schol, J. & Sakai, D. Int. Orthop. 43, 1011-1025 (2019)). These cell therapies have mixed results and those with best regenerative effects utilize cells derived from tissues types they are being implanted into, or similar tissues (Schol, J. & Sakai, D. Int. Orthop. 43, 1011-1025 (2019); and De Bari, C. & Roelofs, A. J. Current Opinion in Pharmacology 40, 74-80 (2018)). Thus, their phenotype is already designed to survive in the harsh musculoskeletal microenvironments. Deriving cells from articular cartilage and intervertebral disc (IVD) is non-trivial due to low cellularity of these tissues (Maroudas, A., Stockwell, R. A., Nachemson, A. & Urban, A. J. J. Anat 120, 113-130 (1975); and Stockwell, R. A. J. Anat 101, (1967)) and the need for cell extraction from healthy tissue, which compromises donor site tissue or requires limited cadaver tissue. An ability to more reliably utilize stem cells is an improvement, as stem cells can be extracted from sources which repair themselves such as fat and bone marrow.

To make stem cell therapies more consistently regenerative, previous work has attempted to match stem cell phenotype to native musculoskeletal cells by promoting their differentiation often using growth factors (Puetzer, J. L., Petitte, J. N. & Loboa, E. G. Tissue Eng. Part B. Rev. 16, 435-44 (2010)), biomaterials with growth factors (Liu, Z., Tang, M., Zhao, J., Chai, R. & Kang, J. Adv. Mater. 30, 1705388 (2018)) or gene therapies that introduce growth factors (Frisch, J., Venkatesan, J. K., Rey-Rico, A., Madry, H. & Cucchiarini, M. Curr. Stem Cell Res. Ther. 10, 121-31 (2015)). These approaches have shown some success but they do have issues. One issue is growth factors effects are inhibited by the hostile inflammatory microenvironments within pathological musculoskeletal tissues (Krock, E., Rosenzweig, D. & Haglund, L. Curr. Stem Cell Res. Ther. 10, 317-328 (2015); and Diekman, B. O. & Guilak, F. Curr. Opin. Rheumatol. 25, 119-126 (2013)). Another is these approaches do not provide precise control over levels of expressed matrix proteins, which is needed to best mimic, native tissue. For example, articular cartilage has a type II collagen to aggrecan ratio of about 2:1, whereas the nucleus pulposus of the IVD has a ratio of about 27:1 (Mwale, F., Roughley, P. & Antoniou, J. Eur. Cells a¨nd Mater. 8, 58-64 (2004)). Previous work directly regulating ECM protein expression is limited. This is likely as delivery of these genes is non-trivial due to their large size (Kreiss, P. et al. Nucleic Acids Res. 27, 3792-3798 (1999)), and endogenous gene activation techniques prior to CRISPR gene activation (CRISPRa) (i.e., TALENs) are difficult to design due to need for protein engineering (Gersbach, C. A. & Perez-Pinera, P. Expert Opin. Ther. Targets 18, 835-9 (2014)). One study has attempted to directly regulate production of type II collagen and aggrecan (Shi, S. et al. Cartilage 10, 102-110 (2019)). This work by Shi et al introduced transcripts for type II collagen subunit, COL2A1, and the gene for aggrecan, ACAN, into bovine articular chondrocytes but demonstrated no increase in these proteins. This may be due to these proteins having complex biosynthesis pathways which require numerous chaperone proteins and post-translational modifications (Sorushanova, A. et al. Adv. Mater. 31, 1801651 (2019); and Vertel, B. M. Trends in Cell Biology 5, 458-464 (1995)).

Described herein is an alternative method of directly regulating expression of ACAN and COL2A1 in human adipose derived stem cells (hADSCs) using a CRISPRa technique. CRISPRa systems provide the ability to target and upregulate endogenous genes with relative ease as compared to previous systems with similar function (Gersbach, C. A. & Perez-Pinera, P. *Expert Opin. Ther. Targets* 18, 835-9 (2014); Gilbert, L. A. et al. *Cell* 159, 647-61 (2014); and Chavez, A. et al. *Nat. Methods* 12, 326-328 (2015)). The dCas9-VPR CRISPRa system (Chavez, A. et al. *Nat. Methods* 12, 326-328 (2015)) was used to activate genes of interest in hADSCs and demonstrated an ability to robustly upregulate both target proteins singularly and together without the addition of exogenous growth factors. Furthermore, these results indicated COL2A1 upregulation more robustly drove a chondrogenic phenotype by driving broader gene expression changes. Nonetheless, multiplex upregulation of ACAN and COL2A1 induced a phenotype that most closely mimicked that induced by chondrogenic growth factors. Overall, this work indicates dCas9-VPR CRISPRa system can be utilized as a method to robustly upregulate specific endogenous ECM proteins to regulate cell phenotype independent of growth factors, providing a platform to more precisely and directly regulate ECM deposition.

Results. Singular ACAN and COL2A1 Upregulation. Measurement ECM Gene Upregulation by qRT-PCR. Lentivirally delivered dCas9-VPR systems are able to significantly upregulate target genes. Increases of target genes relative to NTC cells are $2^{2.61}$ and $2^{4.75}$-fold for ACAN ($p<0.0001$) and $2^{12.38}$ and $2^{15.28}$-fold for COL2A1 ($p<0.0001$) (FIGS. 26C and D). While gene expression increases for ACAN are lower, the actual amount of gene expression achieved is actually similar to that of COL2A1 as seen when evaluating fold changes in expression relative to COL2A1 upregulated cells (FIG. 26E). This effect is seen as baseline levels of ACAN are higher than that of COL2A1.

Verification of Relevant ECM Deposition in 3D Pellet Culture. Morphological Analysis, Histology and IHC. Gross morphological analysis of pellets indicates visible differences in pellet morphology between cell groups (FIG. 27A). The cell pellet with ACAN upregulated cells has a less dense gel like appearance, akin to the nucleus pulposus tissue of the intervertebral disc which has high rations of aggrecan to collagen content. The pellet with COL2A1 upregulated cells has a more contracted appearance and looks most similar to the growth factor differentiated pellet. Histological analysis of sGAG deposition by alcian blue staining qualitatively demonstrates that sGAG content is enhanced in ACAN and COL2A1 upregulated cells (FIG. 27B). Surprisingly, it can be seen that the increase in sGAG deposition is much more drastic in COL2A1 upregulated cells and staining appears similar to that of growth factor differentiated cells. Examining IHC analysis of collagen II indicates collagen II deposition increases in COL2A1 upregulated cells, although these levels are still below what is seen in growth factor differentiated cells (FIG. 27C).

Figure 28A:
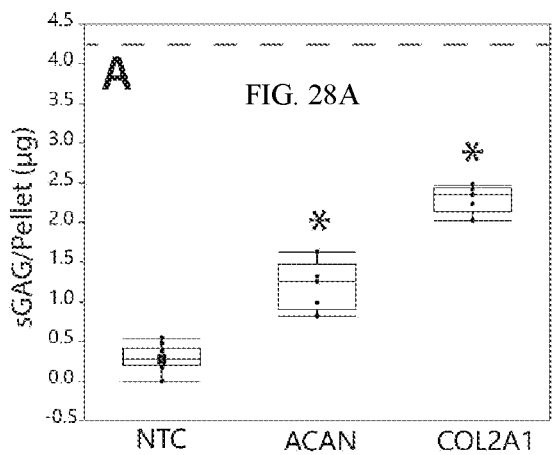
Figure 28B:
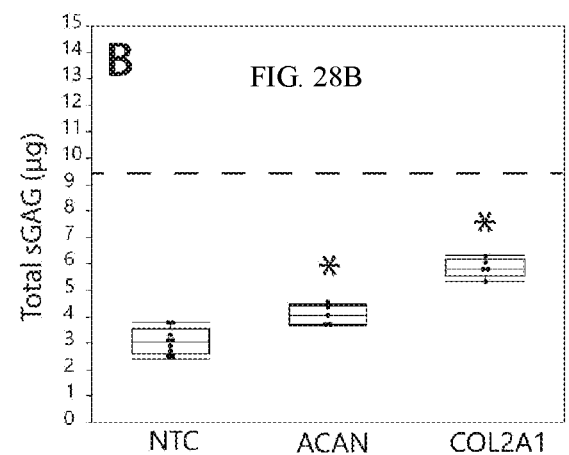
Figure 28C:
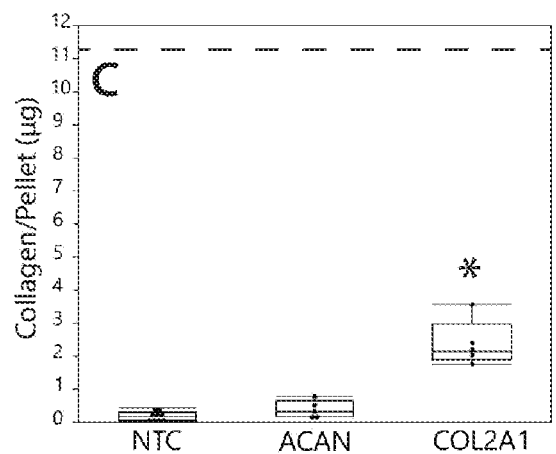
Figure 28D:
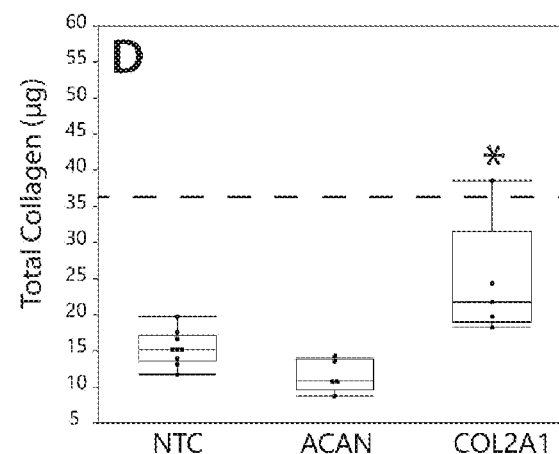

Analysis of sGAG and Collagen Content. Quantitative measurement of sGAG content within pellet cultures demonstrates that sGAG deposition is significantly increased by ACAN or COL2A1 upregulation without exogenous growth factors (FIGS. 28A and B). The pellet (ACAN: $p<0.0001$, COL2A1: $p<0.0001$) and total sGAG content (ACAN: $p=0.0121$, COL2A1: $p<0.0001$) significantly increased for both ACAN and COL2A1 upregulated cells. The sGAG content was surprisingly higher in COL2A1 upregulated cells compared to ACAN (pellet: $p<0.0001$, total: $p=0.0001$). Measurement of collagen content demonstrates that collagen deposition is significantly increased in COL2A1 upregulated cells as expected (pellet: $p=0.001$, total: $p=0.0024$ relative to NTC group) (FIGS. 28C and D). Both the pellet and total collagen content in ACAN upregulated cells do not significantly change compared to NTC cells (pellet: $p=0.972$, total: $p=0.354$). Overall, COL2A1 demonstrated the highest deposition of sGAG and collagen but these levels were still significantly below that of growth factor differentiated cell pellets (sGAG (pellet and total: $p<0.0001$), collagen (pellet: $p<0.0001$, total: $p=0.0002$)).

RNA-seq Analysis. Analysis of cell pellets cultured for one week indicate that COL2A1 upregulation more broadly changes gene expression and that these gene expression change aid in driving a chondrogenic phenotype. A heatmap of the different cell groups shows that the ACAN upregulated cells expression profile is not very different from NTC cells while the COL2A1 expression profile is visibly different (FIG. 29A). This is confirmed in differential expression plots where it can be seen a larger number of genes are differentially expressed in COL2A1 upregulated cells relative to NTC cells (2,532 genes), compared to ACAN upregulated cells relative to NTC cells (38 genes) (FIGS. 29B and C). Interestingly, ACAN was not upregulated during pellet culture as expected in COL2A1 upregulated cells, therefore genes associated with proteoglycans and GAG synthesis were examined to seek why sGAG content was enhanced in these cells. This revealed that proteoglycans Lumican and Biglycan are upregulated along with enzymes associated with GAG synthesis, explaining the increase in sGAG content (FIG. 29D). Gene enrichment analysis revealed several biological processes significantly associated with genes upregulated in COL2A1 upregulated cells, whereas no biological processes were significantly associated with genes upregulated in ACAN upregulated cells (FIG. 94E). Aside from the expected biological processes associated with ECM organization, biological processes associated endoplasmic reticulum (ER) stress responses are also significantly associated with genes upregulated in COL2A1 upregulated cells. This makes sense as the ER stress response has previously been associated with chondrogenic differentiation (Hino, K. et al. *J. Biol. Chem.* 289, 13810-13820 (2014); Saito, A. et al. *Nat. Cell Biol.* 11, 1197-1204 (2009); and Shen, C. et al. *J. Biol. Eng.* 12, 26 (2018)).

Multiplex ACAN and COL2A1 Upregulation. Verification of ACAN & COL2A1 Gene Upregulation by qRT-PCR. Multiplex delivery ACAN and COL2A1 along with dCas9-VPR systems is able to significantly upregulate both COL2A1 and ACAN. Increase of ACAN relative to NTC cells are $2^4$-fold ($p=0.0008$) (FIG. 30B). Increase of COL2A1 relative to NTC cells are $2^{17.66}$-fold ($p<0.0001$) (FIG. 30C). This demonstrates multiplex gene upregulation can provide similar gene upregulation results to singular gene upregulation.

Verification of Relevant Protein Deposition in 3D Pellet Culture. Morphological Analysis, Histology and IHC. Gross morphological analysis of pellets indicates visible differences in pellet morphology between cell groups (FIG. 31A). The cell pellet with multiplex ACAN and COL2A1 upregulated cells has a contracted appearance similar to that of the growth factor differentiated pellet. Histological analysis of sGAG deposition by alcian blue staining qualitatively demonstrates that sGAG content is increases in multiplex ACAN and COL2A1 upregulated cells relative to NTC cells as expected, and staining appears similar to that of growth factor differentiated cells (FIG. 31B). Examining IHC analysis of collagen II indicates collagen II deposition is drastically higher in multiplex ACAN and COL2A1 upregulated cells compared to NTC cells and that levels are close to and even appear a little higher that seen in growth factor differentiated pellets (FIG. 31C).

Analysis of sGAG and Collagen Content. Quantitative measurement of sGAG content within pellet cultures demonstrates that sGAG deposition is significantly increased by multiplex ACAN and COL2A1 upregulation without exogenous growth factors relative to NTC cells (pellet and total: p<0.0001) (FIGS. 32A and B). The sGAG content within the pellet is still lower than that seen in growth factor differentiated pellets (p<0.0001) but the total sGAG content reaches slightly higher levels (p=0.0049). Measurement of collagen content demonstrates that collagen deposition is significantly increased in multiplex ACAN and COL2A1 upregulated cells relative to NTC cells (pellet and total: p<0.0001) (FIGS. 32C and D). Additionally, it can be noted that pellet levels are close to and total collagen levels are at those seen within growth factor differentiated pellets (pellet: p=0.0079, total: p=0.834).

Discussion Stem cell therapies are useful for cell supplementation within degenerative musculoskeletal tissue which have degenerated and lost many of their cells (Adams, M. A. & Roughley, P. J. *Spine (Phila. Pa.* 1976). 31, 2151-61 (2006); and Sandell, L. J. & Aigner, T. *Arthritis Res.* 3, 107 (2001)). Although their regenerative results, even with help of differentiation enhancing growth factors, are mixed due to microenvironmental challenges inhibiting differentiation (Maldonado, M. & Nam, J. *BioMed Research International* 2013, 284873 (2013); Krock, E., Rosenzweig, D. & Haglund, L. *Curr. Stem Cell Res. Ther.* 10, 317-328 (2015); Diekman, B. O. & Guilak, F. *Curr. Opin. Rheumatol.* 25, 119-126 (2013); and Vadala, G., Ambrosio, L., Russo, F., Papalia, R. & Denaro, V. *Stem Cells Int.* 2019, 1-15 (2019)). Control of stem cell phenotype through direct modulation of ECM expression can provide a method to more consistently enhance regenerative effects within pathological musculoskeletal tissue and allows for more precise control of phenotype depending on the desired application. As described herein, the dCas9-VPR CRISPRa system was utilized to upregulate ECM proteins relevant to musculoskeletal tissue, aggrecan and collagen II, to achieve a more direct control of cell phenotype.

CRISPRa systems were able to successfully singularly upregulate expression of ACAN and COL2A1 in hADSCs (FIG. 26). The overall level of expression reached is slightly higher for COL2A1 but similar between COL2A1 and ACAN. Once these systems were verified to perform successful gene upregulation, their effects on ECM production in pellet culture without exogenous growth factors was analyzed. This was to determine if this ECM targeted gene upregulation could independently enhance deposition of targeted ECM proteins. From this experiment, the results show that ECM expression can be modulated and that COL2A1 upregulation had broader effects on cell phenotype (FIGS. 27 and 28). This was characterized by elevated sGAG deposition in addition to expected elevated collagen II deposition seen both qualitatively and quantitatively. While collagen and sGAG deposition are enhanced in COL2A1 upregulated cells, they do not reach levels seen with added growth factors.

To further investigate these effects of COL2A1 upregulation, RNA-seq analysis of pellets from cell groups cultured for 1-week were performed to capture active gene expression changes occurring during 3D culture. From this analysis, the results showed that COL2A1 upregulation was creating much broader gene expression changes than ACAN, with 2,532 genes differentially expressed in COL2A1 upregulated cells compared to 38 genes in ACAN upregulated cells (FIG. 29). Gene enrichment analysis of differentially expressed genes indicates there are biological processes enriched in COL2A1 upregulated cells. Taking a closer look at the top 5 biological processes enriched, processes associated with ECM organization, and with ER stress were observed. Enrichment of biological processes associated with ER stress is notable as ER stress has been previously implicated in playing an important role in cell differentiation, including chondrogenic differentiation (Hino, K. et al. *J. Biol. Chem.* 289, 13810-13820 (2014); Saito, A. et al. *Nat. Cell Biol.* 11, 1197-1204 (2009); Shen, C. et al. *J. Biol. Eng.* 12, 26 (2018); and Matsuzaki, S. et al. *PLoS One* 10, e0123578 (2015)). To help explain increases in sGAG deposition, genes associated with proteoglycans and enzymes involved in sGAG synthesis were examined. Surprisingly, ACAN was not upregulated in COL2A1 cells in 3D culture but other proteoglycans and enzymes associated sGAG synthesis were, helping explain why sGAG deposition increased. Overall this data further supports that COL2A1 upregulation has broader desired effects by inducing differentiation in 3D culture without growth factors. Although major gene expression changes associated with differentiation into chondrogenic cells of cartilage or disc, including ACAN upregulation (Sekiya, I., Vuoristo, J. T., Larson, B. L. & Prockop, D. J. *Proc. Natl. Acad. Sci. U.S.A* 99, 4397-402 (2002); and Risbud, M. V et al. *J Orthop Res* 33, 283-293 (2015)), do not occur, helping explain why sGAG and collagen deposition levels don't reach that of growth factor differentiated cells.

To better promote the desired chondrogenic phenotype, both ACAN and COL2A1 were upregulated in the hADSCs. Prior to performing pellet cultures, it was verified that both genes were upregulated to similar levels achieved singularly via qPCR. Once this was verified, these cells were analyzed in pellet culture and it was found that a chondrogenic phenotype with this multiplex ECM gene upregulation can be better promoted. This was seen by total sGAG and collagen deposition reaching levels achieved by growth factors as well as drastic increases in collagen II IHC staining (FIGS. 31 and 32). These results indicate that collagen II and aggrecan deposition together, synergistically drive chondrogenic ECM deposition, at levels similar to growth factor differentiated cells.

It is interesting to note that COL2A1 upregulation, even by itself, caused such drastic changes and ACAN did not. This may be due to structural changes in the environment COL2A1 upregulation induces that ACAN upregulation does not. Images of the pellet culture morphology show that the pellet with COL2A1 upregulated cells has a more contracted and dense appearance, like that of the growth factor treated pellet (FIG. 27A). It is known that the structural properties of a cell's environment like tissue density and stiffness do influence stem cell phenotype (Engler, A. J., Sen, S., Sweeney, H. L. & Discher, D. E. *Cell* 126, 677-689 (2006); Matsiko, A., Gleeson, J. P. & O'Brien, F. J. *Tissue Eng. Part A* 21, 486-97 (2015); and Lee, B. L. P. et al. *Acta Biomater.* 9, 7264-75 (2013)). The pellet contraction in COL2A1 upregulated pellets creates an environment with a structure more like that of the growth factor treated pellets. It is also known that ECM content influences cell phenotype (Lin, X. et al. *Oncotarget* 7, 12121-36 (2016); Illien-Jünger, S. et al. *J. Orthop. Res.* 34, 876-88 (2016); and Tamaddon, M. et al. *Sci. Rep.* 7, 43519 (2017)) therefore the changes in surrounding structure and ECM content likely work together to induce phenotypic changes in the hADSCs. This is also likely why multiplexing ACAN upregulation with COL2A1 upregulation most robustly induces cartilaginous tissue formation. It is still unclear why the differences in mechanical environment and ECM content caused by ACAN upregulation did not induce phenotypic changes that more drastically increase sGAG content. Lack of collagen II could be cause, as there wasn't really any collagen II produced by these cells (FIG. 27) and although it is known that there is lower but still some collagen II present, even within more sGAG rich tissues like nucleus pulposus (Mwale, F., Roughley, P. & Antoniou, J. *Eur. Cells a¨nd Mater.* 8, 58-64 (2004)).

Taken together, these results provide a platform for utilizing dCas9-VPR systems to upregulate major musculoskeletal ECM proteins Aggrecan and Collagen II to improve regenerative properties of stem cell therapies. While hADSCs were used, these lentiviral CRISPRa systems can be applied to other stem cells types as lentivirus to perform gene delivery to a broad range of cell types (Cronin, J., Zhang, X. Y. & Reiser, *J. Curr. Gene Ther.* 5, 387-98 (2005)). The delivery of the dCas9-VPR system can also be done non-virally to improve the safety profile of this approach, although this would have the drawback of reducing the longevity of the effects of ECM gene upregulation and less efficient gene delivery as non-viral gene delivery is transient and less efficient (Ramamoorth, M. & Narvekar, A. *J. Clin. Diagn. Res.* 9, GE01-6 (2015)). Nonetheless either approach is clinically feasible in terms of safety, as lentivirus is extensively used in ex vivo engineered cells therapies currently being clinically tested (White, M., Whittaker, R., Gándara, C. & Stoll, E. A. *Human Gene Therapy Methods* 28, 163-176 (2017); and Milone, M. C. & O'Doherty, U. *Leukemia* 32, 1529-1541 (2018)).

Conclusion. As described herein, CRISPRa systems were used to upregulate Aggrecan and Collagen II to effectively modulate stem cell phenotype without exogenous growth factors. The results demonstrated that both ECM genes can be effectively upregulated at a transcriptional and translational level. Additionally, the results demonstrated that COL2A1 upregulation has broader effects on cell phenotype in 3D pellet culture and that multiplexing COL2A1 with ACAN upregulation induces stem cells to produce tissue that most closely resembles that produced by cells in chondrogenic growth factor treated pellets. In summary, these results demonstrate the ability to use the systems disclosed herein to robustly upregulate these ECM genes in stem cells. Thereby these systems provide a platform to upregulate aggrecan and collagen II at varying levels to best recapitulate phenotype of cells of different musculoskeletal tissues when engineering improved stem cell therapies for musculoskeletal disease.

Methods. Experimental Overview. Lentiviral vectors were built to upregulate genes ACAN and COL2A1 using the dCas9-VPR CRISPRa system. These lentiviral vectors were transduced into hADSCs to test their ability to engineer stem cells with enhanced regenerative phenotype. Ability to upregulate target genes was verified by quantitative reverse transcriptase PCR (qRT-PCR). Once gene upregulation was verified the ability of these systems to upregulate relevant protein expression in 3D pellet culture was measured via histology, IHC and biochemical assays. Additionally, broader gene expression changes to these systems induce during 3D culture was assessed via RNA-seq. Both COL2A1 and ACAN upregulation provided desired positive effects but effects of COL2A1 upregulation were more robust. Therefore, COL2A1 and ACAN upregulation were multiplexed and effects were tested in pellet culture to explore how co-deposition of these proteins can further enhance desired phenotypes.

Vector Constructs, gRNA Design, and Cloning. Guide RNA design was performed using Genome Target Scan 2 (GT-Scan 2) (O'Brien, A. & Bailey, T. L. *Bioinformatics* 30, 2673-5 (2014)). The 5'-UTR and the promoter region up to 500 base pairs upstream of ACAN and COL2A1 were analyzed for gRNAs. Top gRNAs with the fewest off-target sites were further inspected using the BLAT tool of the UCSC genome browser (Kent, W. J. *Genome Res.* 12, 656-664 (2002)), to ensure gRNA sequences do not overlap and have at least 50 bp spacing. Two gRNAs per gene were selected along with a gRNA that does not target the human genome (nontarget control/NTC) (FIG. 26A). These gRNAs were synthesized, annealed, phosphorylated, and ligated into a vector for gRNA expression (Addgene, 83919). Insertion of gRNA sequences was verified by sanger sequencing. For dCas9-VPR expression, a previously made lentiviral vector was utilized (FIG. 26A, Addgene, 99373).

Lentivirus Production. Lentivirus production was performed (Farhang, N. et al. *Tissue Eng. PartA* 23, 738-749 (2017)). For gRNA lentivirus, supernatant containing lentivirus was directly diluted and utilized for transduction as described herein. For dCas9-VPR lentivirus, lentivirus containing supernatant was concentrated 100× by centrifuging at 20,000 g for 4 hours at 4° C. and then resuspending in appropriate amount of PBS(Cribbs, A. P., Kennedy, A., Gregory, B. & Brennan, F. M. *BMC Biotechnol.* 13, 98 (2013)). Virus was aliquoted, and frozen at −80° C. for later use.

Lentivirus Transduction. Lentiviral constructs were sequentially transduced into immortalized hADSCs (SRCR-4000, ATCC) as follows. Human ADSCs were plated at a density of 10,000 cells/cm$^2$ in 24-well plates in 500 μL of manufacture-recommended expansion media (PCS-500-040, ATCC), and allowed to adhere overnight. The next day, concentrated dCas9-VPR virus was diluted 1:10 with expansion media supplemented with 2 μg/mL polybrene and placed on cells (250 μl virus/well). After 24 hours, virus was removed and cells were washed 5× with PBS. Three days later, puromycin cell selection was performed using 1.25 μg/mL puromycin for 3 days, with media changes each day. Untransduced cells were puromycin treated alongside as a negative control to ensure selection of transduced cells. This process resulted in a population of hADSCs expressing dCas9-VPR. These cells were then transduced with gRNA virus using same transduction protocol above, with the modification of diluting the virus 1:4, and using 4 μg/mL polybrene. Transduced cells were not sorted for as transduction efficiency was at nearly 100%. Cells were cultured for at least 7 days to allow for transgene expression and generation of a sufficient number of cells for experiments.

Verification of ACAN and COL2A1 Upregulation. Transduced cells were analyzed for ACAN and/or COL2A1 gene expression by qRT-PCR as follows (n=3). RNA was harvested via Purelink RNA Micro Kit (Ambion). Complementary DNA (cDNA) synthesis was performed with purified RNA using the high-capacity cDNA reverse transcription kit with RNAse inhibitor (Applied Biosystems). This cDNA was then used for qPCR with TaqMan gene expression assays (thermofisher) for genes of interest (ACAN: Hs00153936_m1, COL2A1: Hs00264051_m1) as well as a housekeeping gene (GAPDH: Hs02758991_g1). Changes in ACAN or COL2A1 expression were normalized to GAPDH expression and fold change in mRNA expression relative to the NTC or COL2A1 upregulated cells was calculated using the ΔΔCt method.

Pellet Culture of hADSCs. Human ADSCs containing the best performing gRNAs for each gene were put through pellet culture to assess changes in ECM deposition induced by targeted gene upregulation. Pellet cultures were performed according to previous methods but without any growth factors added to basal media (Farhang, N. et al. *Tissue Eng. Part A* 23, 738-749 (2017)). Pellets were cultured for 21 days with media changed every 2-3 days. As a positive control, NTC cells were cultured in basal media with chondrogenic growth factors (10 ng/mL TGFβ3 and BMP-6 (peprotech)). Cell pellets were harvested after 21 days of culture for imaging, histology, collagen II immunohistochemistry (IHC) and biochemical analysis as described herein. Supernatant was collected and stored at −20° C. at each media change for future biochemical analysis.

Macroscopic Pellet Imaging. At the end of pellet culture, pellets were imaged (Pentax K5) in their respective wells for qualitative comparison of gross pellet phenotype.

Histology & Immunohistochemistry. To prepare pellets for staining, pellets (n=4) were fixed in 10% neutral-buffered formalin solution for 24 h. Pellets were then embedded in paraffin, and 5 μm sections were mounted on glass slides.

Sections for each sample were stained with Alcian Blue to qualitatively analyze sGAG. Sections were deparaffinized, hydrated in distilled water, and mordanted with 3% glacial acetic acid for 3 minutes. Alcian Blue (pH 2.5, Newcomer Supply) was then applied for 30 minutes. Sections were then washed in running tap water for 10 minutes, rinsed in distilled water and counterstained in Nuclear Fast Red (Newcomer Supply) for 5 minutes. Sections were washed in running tap water for 1 minute before being dehydrated, cleared in xylene, and cover-slipped.

For collagen II IHC staining, samples were processed using the following protocol. Sections were air-dried and melted in a 60° C. oven for 30 minutes. Slides were then loaded onto the Ventana ULTRA automated staining instrument for following steps. Slides were deparaffinized with EZ Prep solution (Ventana Medical systems (VMS)) and antigen retrieval was performed with Protease 2 enzyme (VMS) for 12 minutes at 37° C. Primary antibody (Polyclonal rabbit anti-collagen II, Leica) was applied at a concentration of 1:50 for 2 hours at room temperature. Subsequently an amplification kit (VMS) was applied to increase the antibody signal. Antibody staining was then visualized using the ultraView Universal DAB detection kit (VMS). Sections were counterstained with hematoxylin (VMS) for 8 minutes. The slides were gently washed in a mixture of 1% DAWN™ in distilled water solution, and then just distilled water until the wash mixture was removed. Slides were de-hydrated in graded ethanol solutions, cleared in xylene and cover-slipped.

Sulfated Glycosaminoglycan (sGAG) Quantification. Papain-digested pellet cultures (n=5-10) and supernatant from pellet cultures (n=5-10) were analyzed for sulfated GAG content (sGAG) using a Dimethylmethylene Blue (DMMB) assay (Zheng, C. H. & Levenston, M. E. *Eur. Cell. Mater.* 29, 224-36; discussion 236 (2015)).

Hydroxyproline Quantification. Papain-digested pellet cultures (n=5-10) and pellet culture supernatant (n=5-10) were analyzed for hydroxyproline content using a protocol adapted from a previously described hydroxyproline assay (Cissell, D. D., Link, J. M., Hu, J. C. & Athanasiou, K. A. *Tissue Eng. Part C. Methods* 23, 243-250 (2017)). Adaptations include increasing autoclaving for hydrolysis to 40 minutes and adjusting pH of oxidation buffer to 6.5 with glacial acetic acid.

RNA sequencing. Human ADSCs with or without ACAN or COL2A1 upregulation were put through pellet culture for one week and harvested for subsequent RNA-seq analysis (n=2 pellets/group). Pellets were cultured for 6 days before being harvested for RNA-seq analysis. Total RNA was harvested using Purelink RNA Micro kit (Thermofisher). Total RNA (100-500 ng) was hybridized with Ribo-Zero Gold to substantially deplete cytoplasmic and mitochondrial rRNA from the samples. Stranded RNA sequencing libraries were prepared using the Illumina TruSeq Stranded Total RNA Library Prep Gold kit with TruSeq RNA UD Indexes. Sequencing libraries (1.3 nM) were chemically denatured and applied to an Illumina NovaSeq flow cell using the NovaSeq XP chemistry workflow and a 2×51 cycle paired end sequence run was performed using a NovaSeq S1 reagent Kit.

Sequencing reads were aligned to the hg19 build of the human genome using HISAT2 (Kim, D., Langmead, B. & Salzberg, S. L. *Nat. Methods* 12, 357-60 (2015)). Sam files were converted to bam format and sorted using SAM-tools (Li, H. et al. *Bioinformatics* 25, 2078-9 (2009)). Reads mapping to UCSC known genes (Kent, W. J. et al. *Genome Res.* 12, 996-1006 (2002)) were counted using feature-Counts from the SubRead package (Liao, Y., Smyth, G. K. & Shi, W. *Bioinformatics* 30, 923-30 (2014)). Reads were normalized and differential analysis was done in a pairwise manner using DESeq2 (Love, M. I., Huber, W. & Anders, S. *Genome Biol.* 15, 550 (2014)). Heatmaps were generated using pheatmap package in R (Kolde, R. pheatmap: Pretty Heatmaps. R package version 1.0.12 (2019). Available at: cran.r-project.org/package=pheatmap). GO biological processes enriched were determined from genes significantly upregulated using Enrichr (Kuleshov, M. V. et al. *Nucleic Acids Res.* 44, W90-W97 (2016); Chen, E. Y. et al. *BMC Bioinformatics* 14, 128 (2013); and The Gene Ontology project in 2008. *Nucleic Acids Res.* 36, D440-D444 (2008)).

Multiplex Aggrecan and Collagen II Upregulation. To investigate if multiplexing COL2A1 and ACAN upregulation enhances desired phenotypic effects, hADSCs with collagen II upregulated were transduced with the gRNA that best upregulates ACAN (gRNA 2) using lentivirus transduction methods as described herein. This generated hADSCs with simultaneous COL2A1 and ACAN upregulation. To verify both genes were upregulated, qRT-PCR for ACAN and COL2A1 was performed on cells as described herein (n=3). Once simultaneous upregulation was verified, cells were then put through pellet culture as described herein. Pellets underwent the same imaging ("Macroscopic Pellet Imaging"), histological and IHC analysis ("Histology and Immunohistochemistry", n=4), and biochemical analysis ("sGAG Quantification" and "Hydroxyproline Quantification", n=5-6).

Statistics. Statistical analysis of qRT-PCR and biochemical data was performed using JMP pro 14 software (SAS). These data were analyzed by a one-way ANOVA, using Tukey's post hoc test, with the exception of qRT-PCR data for multiplex gene upregulation which had two experimental groups and was analyzed by a two-tailed student's t-test ($\alpha$=0.05 for tests). Statistical analysis of RNA-seq data was performed through data analysis tools utilized to analyze differential gene expression data (Enrichr, DESEQ2, $\alpha$=0.05).

What is claimed is:

1. A CRISPR-Cas system comprising one or more vectors comprising:
   a) a promoter operably linked to one or more nucleotide sequences encoding a CRISPR-Cas system guide RNA (gRNA), wherein the gRNA hybridizes with a target sequence of a DNA locus in a cell; and
   b) a regulatory element operably linked to a nucleotide sequence encoding a RNA-directed nuclease,
   wherein components a) and b) are located on the same or different vectors of the same system, wherein the gRNA targets and hybridizes with the target sequence and directs the RNA-directed nuclease to the DNA locus;
   wherein the gRNA comprises:
   a gRNA sequence having the sequence of SEQ ID NOs: 134, 131, 133, 135, 136, 137, 139, or 140; and
   a gRNA sequence having the sequence of SEQ ID NOs: 148, 141, 142, 143, 144, 146, or 147.

2. The CRISPR-Cas system of claim 1, wherein the RNA-directed nuclease is a dCas9 protein.

3. The CRISPR-Cas system of claim 2, wherein the sequence encoding the Cas9 protein is codon optimized for expression in the cell.

4. The CRISPR-Cas system of claim 1, wherein the cell is a mammalian cell.

5. The CRISPR-Cas system of claim 4, wherein the mammalian cell is a mesenchymal stem cell.

6. The CRISPR-Cas system of claim 4, wherein the mammalian cell is a human cell.

7. The CRISPR-Cas system of claim 6, wherein the human cell is a human mesenchymal stem cell.

8. The CRISPR-Cas system of claim 1, wherein the system is packaged into a single lentiviral, adenoviral or adeno-associated virus particle.

9. A pharmaceutical composition comprising the CRISPR-Cas system of claim 1, and a pharmaceutically acceptable carrier.

10. The pharmaceutical composition of claim 9, wherein the pharmaceutically acceptable carrier comprises a lipid-based or polymer-based colloid.

* * * * *

SEQUENCE LISTING

<160> NUMBER OF SEQ ID NOS: 148

<210> SEQ ID NO 1
<211> LENGTH: 20

```
<212> TYPE: DNA
<213> ORGANISM: Artificial Sequence
<220> FEATURE:
<223> OTHER INFORMATION: Synthetic construct

<400> SEQUENCE: 1
cagtgttgca acagcgggac                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
agactcgggc atagagatca                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
gaatggcagg cacccagtca                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
ataagcgtcc gacacatgat                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5 gcaagggggct tattgcccct                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
ggagtcgcca actcaattcg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic construct

<400> SEQUENCE: 7
``` tggggtccttgggcgactgc        20

<210> SEQ ID NO 8
<211> LENGTH: 20
<212> TYPE: DNA
<213> ORGANISM: Artificial Sequence
<220> FEATURE:
<223> OTHER INFORMATION: Synthetic construct

<400> SEQUENCE: 8 agaggcatttcccggactcg        20

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9 agcacaaagttggctgcgcc        20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10 gggaggtgacacccagttta        20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11 aaagtagcctgacgtatccg        20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12 tttttaatacaaggtaatct        20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13 gaaggctggatgcgtgttta        20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
tcaagtgatc ttcccgcctc					20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

<400> SEQUENCE: 15
gtgagggtga ggcactaatt					20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
cgggctttcg ctttcagtcg					20

<210> SEQ ID NO 17
<211> LENGTH: 20
<212> TYPE: DNA
<213> ORGANISM: Artificial Sequence
<220> FEATURE:
<223> OTHER INFORMATION: Synthetic construct

<400> SEQUENCE: 17
aggtatcggc ccagcgatgc					20

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
catgtcctaa aatcacgaac					20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
aattgtgata ctagcggtta					20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct

<400> SEQUENCE: 20
aggataaaac tagggcccat					20

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
caaggtttta cgctcccatt                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
gggaggtgac acccagttta                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic construct

<400> SEQUENCE: 23
taaacacctg acacacggtc                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
cggaagactc accaccgtaa                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
agggcgtatc agccaccagt                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
cggctttcgt aaccgcaccc                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

```
<400> SEQUENCE: 27
agagccgggc tcctgcggat                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic construct

<400> SEQUENCE: 28
aggctcgttt acgtaagtct                                                    20

<210> SEQ ID NO 29
<211> LENGTH: 20
<212> TYPE: DNA
<213> ORGANISM: Artificial Sequence
<220> FEATURE:
<223> OTHER INFORMATION: Synthetic construct

<400> SEQUENCE: 29
ggaataacgg ggtcatgaac                                                    20

<210> SEQ ID NO 30
<211> LENGTH: 20
<212> TYPE: DNA
<213> ORGANISM: Artificial Sequence
<220> FEATURE:
<223> OTHER INFORMATION: Synthetic construct

<400> SEQUENCE: 30
cagtggccgc ctgtcgacga                                                    20

<210> SEQ ID NO 31
<211> LENGTH: 20
<212> TYPE: DNA
<213> ORGANISM: Artificial Sequence
<220> FEATURE:
<223> OTHER INFORMATION: Synthetic construct

<400> SEQUENCE: 31
cgcacgaacc ccttggcgcc                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic construct

<400> SEQUENCE: 32
tcaacaggat cacgacctta                                                    20

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
atcgtggttc atcgccaaac                                                    20

<210> SEQ ID NO 34
```

```
<211> LENGTH: 20
<212> TYPE: DNA
<213> ORGANISM: Artificial Sequence
<220> FEATURE:
<223> OTHER INFORMATION: Guide RNA

<400> SEQUENCE: 34
gctgcatctc tatgcggaca                                                  20

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
ttagcgtctc agaaaacgcg                                                  20

<210> SEQ ID NO 36
<211> LENGTH: 20
<212> TYPE: DNA
<213> ORGANISM: Artificial Sequence
<220> FEATURE:
<223> OTHER INFORMATION: Synthetic construct

<400> SEQUENCE: 36
aaactgtgca tagaatagcg                                                  20

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37
aagatcaacg tagggcgtcg                                                  20

<210> SEQ ID NO 38
<211> LENGTH: 20
<212> TYPE: DNA
<213> ORGANISM: Artificial Sequence
<220> FEATURE:
<223> OTHER INFORMATION: Synthetic construct

<400> SEQUENCE: 38
ccttgctccg ggtgcgaccg                                                  20

<210> SEQ ID NO 39
<211> LENGTH: 20
<212> TYPE: DNA
<213> ORGANISM: Artificial Sequence
<220> FEATURE:
<223> OTHER INFORMATION: Synthetic construct

<400> SEQUENCE: 39
gcgcccgggc ggagcacgat                                                  20

<210> SEQ ID NO 40
<211> LENGTH: 20
<212> TYPE: DNA
<213> ORGANISM: Artificial Sequence
<220> FEATURE:
<223> OTHER INFORMATION: Synthetic construct

<400> SEQUENCE: 40
```
aattagctgg gcgcaatggc								20

<210> SEQ ID NO 41
<211> LENGTH: 20
<212> TYPE: DNA
<213> ORGANISM: Artificial Sequence
<220> FEATURE:
<223> OTHER INFORMATION: Synthetic construct

<400> SEQUENCE: 41
gagtaggggt tggcgtcgag								20

<210> SEQ ID NO 42
<211> LENGTH: 20
<212> TYPE: DNA
<213> ORGANISM: Artificial Sequence
<220> FEATURE:
<223> OTHER INFORMATION: Synthetic construct

<400> SEQUENCE: 42
gacgctagtt ttgacgtcgc								20

<210> SEQ ID NO 43
<211> LENGTH: 20
<212> TYPE: DNA
<213> ORGANISM: Artificial Sequence
<220> FEATURE:
<223> OTHER INFORMATION: Synthetic construct

<400> SEQUENCE: 43
gagtcgctgt ggacgccctt								20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct

<400> SEQUENCE: 44
tgaaggcggt tgctactcga								20

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
aaggcagctg cttgcatcgc								20

<210> SEQ ID NO 46
<211> LENGTH: 20
<212> TYPE: RNA
<213> ORGANISM: Artificial Sequence
<220> FEATURE:
<223> OTHER INFORMATION: Synthetic construct

<400> SEQUENCE: 46
gaaggcugga ugcguguuua								20

<210> SEQ ID NO 47
<211> LENGTH: 20
<212> TYPE: RNA

```
<213> ORGANISM: Artificial Sequence
<220> FEATURE:
<223> OTHER INFORMATION: Synthetic construct

<400> SEQUENCE: 47
ucaagugauc uucccgccuc                                               20

<210> SEQ ID NO 48
<211> LENGTH: 20
<212> TYPE: RNA
<213> ORGANISM: Artificial Sequence
<220> FEATURE:
<223> OTHER INFORMATION: Synethic construct

<400> SEQUENCE: 48
gugagggugu ggcacuaauu                                               20

<210> SEQ ID NO 49
<211> LENGTH: 20
<212> TYPE: RNA
<213> ORGANISM: Artificial Sequence
<220> FEATURE:
<223> OTHER INFORMATION: Synthetic construct

<400> SEQUENCE: 49
cgggcuuucg cuuucagucg                                               20

<210> SEQ ID NO 50
<211> LENGTH: 20
<212> TYPE: RNA
<213> ORGANISM: Artificial Sequence
<220> FEATURE:
<223> OTHER INFORMATION: Synthetic construct

<400> SEQUENCE: 50
agguaucggc ccagcgaugc                                               20

<210> SEQ ID NO 51
<211> LENGTH: 20
<212> TYPE: RNA
<213> ORGANISM: Artificial Sequence
<220> FEATURE:
<223> OTHER INFORMATION: Synthetic construct

<400> SEQUENCE: 51
cauguccuaa aaucacgaac                                               20

<210> SEQ ID NO 52
<211> LENGTH: 20
<212> TYPE: RNA
<213> ORGANISM: Artificial Sequence
<220> FEATURE:
<223> OTHER INFORMATION: Synthetic construct

<400> SEQUENCE: 52
aauugugaua cuagcgguua                                               20

<210> SEQ ID NO 53
<211> LENGTH: 20
<212> TYPE: RNA
<213> ORGANISM: Artificial Sequence
<220> FEATURE:
<223> OTHER INFORMATION: Synthetic construct

<400> SEQUENCE: 53
aggauaaaac uagggcccau                                               20
```

<210> SEQ ID NO 54
<211> LENGTH: 20
<212> TYPE: RNA
<213> ORGANISM: Artificial Sequence
<220> FEATURE:
<223> OTHER INFORMATION: Synthetic construct

<400> SEQUENCE: 54
caagguuuua cgcucccauu                                               20

<210> SEQ ID NO 55
<211> LENGTH: 20
<212> TYPE: RNA
<213> ORGANISM: Artificial Sequence
<220> FEATURE:
<223> OTHER INFORMATION: Synthetic construct

<400> SEQUENCE: 55
gggaggugac acccaguuua                                               20

<210> SEQ ID NO 56
<211> LENGTH: 20
<212> TYPE: RNA
<213> ORGANISM: Artificial Sequence
<220> FEATURE:
<223> OTHER INFORMATION: Synthetic construct

<400> SEQUENCE: 56
uaaacaccug acacacgguc                                               20

<210> SEQ ID NO 57
<211> LENGTH: 20
<212> TYPE: RNA
<213> ORGANISM: Artificial Sequence
<220> FEATURE:
<223> OTHER INFORMATION: Synthetic construct

<400> SEQUENCE: 57
cggaagacuc accaccguaa                                               20

<210> SEQ ID NO 58
<211> LENGTH: 20
<212> TYPE: RNA
<213> ORGANISM: Artificial Sequence
<220> FEATURE:
<223> OTHER INFORMATION: Synthetic construct

<400> SEQUENCE: 58
agggcguauc agccaccagu                                               20

<210> SEQ ID NO 59
<211> LENGTH: 20
<212> TYPE: RNA
<213> ORGANISM: Artificial Sequence
<220> FEATURE:
<223> OTHER INFORMATION: Synthetic construct

<400> SEQUENCE: 59
cggcuuucgu aaccgcaccc                                               20

<210> SEQ ID NO 60
<211> LENGTH: 20
<212> TYPE: RNA
<213> ORGANISM: Artificial Sequence
<220> FEATURE:

<223> OTHER INFORMATION: Synthetic construct

<400> SEQUENCE: 60
agagccgggc uccugcggau                                                         20

<210> SEQ ID NO 61
<211> LENGTH: 20
<212> TYPE: RNA
<213> ORGANISM: Artificial Sequence
<220> FEATURE:
<223> OTHER INFORMATION: Synthetic construct

<400> SEQUENCE: 61
aggcucguuu acguaagucu                                                         20

<210> SEQ ID NO 62
<211> LENGTH: 20
<212> TYPE: RNA
<213> ORGANISM: Artificial Sequence
<220> FEATURE:
<223> OTHER INFORMATION: Synthetic construct

<400> SEQUENCE: 62
ggaauaacgg ggucaugaac                                                         20

<210> SEQ ID NO 63
<211> LENGTH: 20
<212> TYPE: RNA
<213> ORGANISM: Artificial Sequence
<220> FEATURE:
<223> OTHER INFORMATION: Synthetic construct

<400> SEQUENCE: 63
caguggccgc cugucgacga                                                         20

<210> SEQ ID NO 64
<211> LENGTH: 20
<212> TYPE: RNA
<213> ORGANISM: Artificial Sequence
<220> FEATURE:
<223> OTHER INFORMATION: Synthetic construct

<400> SEQUENCE: 64
cgcacgaacc ccuuggcgcc                                                         20

<210> SEQ ID NO 65
<211> LENGTH: 20
<212> TYPE: RNA
<213> ORGANISM: Artificial Sequence
<220> FEATURE:
<223> OTHER INFORMATION: Synthetic construct

<400> SEQUENCE: 65
ucaacaggau cacgaccuua                                                         20

<210> SEQ ID NO 66
<211> LENGTH: 20
<212> TYPE: RNA
<213> ORGANISM: Artificial Sequence
<220> FEATURE:
<223> OTHER INFORMATION: Synthetic construct

<400> SEQUENCE: 66
aucgugguuc aucgccaaac                                                         20

```
<210> SEQ ID NO 67
<211> LENGTH: 20
<212> TYPE: RNA
<213> ORGANISM: Artificial Sequence
<220> FEATURE:
<223> OTHER INFORMATION: Synthetic construct

<400> SEQUENCE: 67
gcugcaucuc uaugcggaca                                               20

<210> SEQ ID NO 68
<211> LENGTH: 20
<212> TYPE: RNA
<213> ORGANISM: Artificial Sequence
<220> FEATURE:
<223> OTHER INFORMATION: Synthetic construct

<400> SEQUENCE: 68
uuagcgucuc agaaaacgcg                                               20

<210> SEQ ID NO 69
<211> LENGTH: 20
<212> TYPE: RNA
<213> ORGANISM: Artificial Sequence
<220> FEATURE:
<223> OTHER INFORMATION: Synthetic construct

<400> SEQUENCE: 69
aaacugugca uagaauagcg                                               20

<210> SEQ ID NO 70
<211> LENGTH: 20
<212> TYPE: RNA
<213> ORGANISM: Artificial Sequence
<220> FEATURE:
<223> OTHER INFORMATION: Synthetic construct

<400> SEQUENCE: 70
aagaucaacg uagggcgucg                                               20

<210> SEQ ID NO 71
<211> LENGTH: 20
<212> TYPE: RNA
<213> ORGANISM: Artificial Sequence
<220> FEATURE:
<223> OTHER INFORMATION: Synthetic construct

<400> SEQUENCE: 71
ccuugcuccg ggugcgaccg                                               20

<210> SEQ ID NO 72
<211> LENGTH: 20
<212> TYPE: RNA
<213> ORGANISM: Artificial Sequence
<220> FEATURE:
<223> OTHER INFORMATION: Synthetic construct

<400> SEQUENCE: 72
gcgcccgggc ggagcacgau                                               20

<210> SEQ ID NO 73
<211> LENGTH: 20
<212> TYPE: RNA
<213> ORGANISM: Artificial Sequence
<220> FEATURE:
<223> OTHER INFORMATION: Synthetic construct
```

<400> SEQUENCE: 73
aauuagcugg gcgcaauggc                                              20

<210> SEQ ID NO 74
<211> LENGTH: 20
<212> TYPE: RNA
<213> ORGANISM: Artificial Sequence
<220> FEATURE:
<223> OTHER INFORMATION: Synthetic construct

<400> SEQUENCE: 74
gaguaggggu uggcgucgag                                              20

<210> SEQ ID NO 75
<211> LENGTH: 20
<212> TYPE: RNA
<213> ORGANISM: Artificial Sequence
<220> FEATURE:
<223> OTHER INFORMATION: Synthetic construct

<400> SEQUENCE: 75
gacgcuaguu uugacgucgc                                              20

<210> SEQ ID NO 76
<211> LENGTH: 20
<212> TYPE: RNA
<213> ORGANISM: Artificial Sequence
<220> FEATURE:
<223> OTHER INFORMATION: Synthetic construct

<400> SEQUENCE: 76
gagucgcugu ggacgcccuu                                              20

<210> SEQ ID NO 77
<211> LENGTH: 20
<212> TYPE: RNA
<213> ORGANISM: Artificial Sequence
<220> FEATURE:
<223> OTHER INFORMATION: Synthetic construct

<400> SEQUENCE: 77
ugaaggcggu ugcuacucga                                              20

<210> SEQ ID NO 78
<211> LENGTH: 20
<212> TYPE: RNA
<213> ORGANISM: Artificial Sequence
<220> FEATURE:
<223> OTHER INFORMATION: Synthetic construct

<400> SEQUENCE: 78
aaggcagcug cuugcaucgc                                              20

<210> SEQ ID NO 79
<211> LENGTH: 20
<212> TYPE: RNA
<213> ORGANISM: Artificial Sequence
<220> FEATURE:
<223> OTHER INFORMATION: Synthetic construct

<400> SEQUENCE: 79
caguguugca acagcgggac                                              20

<210> SEQ ID NO 80
<211> LENGTH: 20

```
<212> TYPE: RNA
<213> ORGANISM: Artificial Sequence
<220> FEATURE:
<223> OTHER INFORMATION: Synthetic construct

<400> SEQUENCE: 80
agacucgggc auagagauca                                               20

<210> SEQ ID NO 81
<211> LENGTH: 20
<212> TYPE: RNA
<213> ORGANISM: Artificial Sequence
<220> FEATURE:
<223> OTHER INFORMATION: Synthetic construct

<400> SEQUENCE: 81
gaauggcagg cacccaguca                                               20

<210> SEQ ID NO 82
<211> LENGTH: 20
<212> TYPE: RNA
<213> ORGANISM: Artificial Sequence
<220> FEATURE:
<223> OTHER INFORMATION: Synthetic construct

<400> SEQUENCE: 82
auaagcgucc gacacaugau                                               20

<210> SEQ ID NO 83
<211> LENGTH: 20
<212> TYPE: RNA
<213> ORGANISM: Artificial Sequence
<220> FEATURE:
<223> OTHER INFORMATION: Synthetic construct

<400> SEQUENCE: 83
gcaaggggcu uauugcccu                                                20

<210> SEQ ID NO 84
<211> LENGTH: 20
<212> TYPE: RNA
<213> ORGANISM: Artificial Sequence
<220> FEATURE:
<223> OTHER INFORMATION: Synthetic construct

<400> SEQUENCE: 84
ggagucgcca acucaauucg                                               20

<210> SEQ ID NO 85
<211> LENGTH: 20
<212> TYPE: RNA
<213> ORGANISM: Artificial Sequence
<220> FEATURE:
<223> OTHER INFORMATION: Synthetic construct

<400> SEQUENCE: 85 uggggguccuu gggcgacugc                                              20

<210> SEQ ID NO 86
<211> LENGTH: 20
<212> TYPE: RNA
<213> ORGANISM: Artificial Sequence
<220> FEATURE:
<223> OTHER INFORMATION: Synthetic construct

<400> SEQUENCE: 86
```
agaggcauuu cccggacucg                                               20

<210> SEQ ID NO 87
<211> LENGTH: 20
<212> TYPE: RNA
<213> ORGANISM: Artificial Sequence
<220> FEATURE:
<223> OTHER INFORMATION: Synthetic construct

<400> SEQUENCE: 87
agcacaaagu uggcugcgcc                                               20

<210> SEQ ID NO 88
<211> LENGTH: 20
<212> TYPE: RNA
<213> ORGANISM: Artificial Sequence
<220> FEATURE:
<223> OTHER INFORMATION: Synthetic construct

<400> SEQUENCE: 88
gggaggugac acccaguuua                                               20

<210> SEQ ID NO 89
<211> LENGTH: 20
<212> TYPE: RNA
<213> ORGANISM: Artificial Sequence
<220> FEATURE:
<223> OTHER INFORMATION: Synthetic construct

<400> SEQUENCE: 89
aaaguagccu gacguauccg                                               20

<210> SEQ ID NO 90
<211> LENGTH: 20
<212> TYPE: RNA
<213> ORGANISM: Artificial Sequence
<220> FEATURE:
<223> OTHER INFORMATION: Synthetic construct

<400> SEQUENCE: 90
uuuuuaauac aagguaaucu                                               20

<210> SEQ ID NO 91
<211> LENGTH: 20
<212> TYPE: DNA
<213> ORGANISM: Artificial Sequence
<220> FEATURE:
<223> OTHER INFORMATION: Synthetic construct

<400> SEQUENCE: 91
ttatgactac atgattcatg                                               20

<210> SEQ ID NO 92
<211> LENGTH: 20
<212> TYPE: DNA
<213> ORGANISM: Artificial Sequence
<220> FEATURE:
<223> OTHER INFORMATION: Synthetic construct

<400> SEQUENCE: 92
aattaaattg tgatagcata                                               20

<210> SEQ ID NO 93
<211> LENGTH: 20
<212> TYPE: DNA
<213> ORGANISM: Artificial Sequence
<220> FEATURE:
<223> OTHER INFORMATION: Synthetic construct

<400> SEQUENCE: 93
ttctcctttt gatcatctag                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic construct

<400> SEQUENCE: 94
ataacacagg ttgtgtttcc                                               20

<210> SEQ ID NO 95
<211> LENGTH: 20
<212> TYPE: DNA
<213> ORGANISM: Artificial Sequence
<220> FEATURE:
<223> OTHER INFORMATION: Synthetic construct

<400> SEQUENCE: 95
taaagtaaaa tgttcttctc                                               20

<210> SEQ ID NO 96
<211> LENGTH: 20
<212> TYPE: DNA
<213> ORGANISM: Artificial Sequence
<220> FEATURE:
<223> OTHER INFORMATION: Synthetic construct

<400> SEQUENCE: 96
gatgcacaga gatgcttttg                                               20

<210> SEQ ID NO 97
<211> LENGTH: 20
<212> TYPE: DNA
<213> ORGANISM: Artificial Sequence
<220> FEATURE:
<223> OTHER INFORMATION: Synthetic construct

<400> SEQUENCE: 97
gtgccgggaa accttgattg                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic construct

<400> SEQUENCE: 98
caatcaaggt ttcccggcac                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic construct

<400> SEQUENCE: 99
gaaaactaag tttattagag                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic construct

<400> SEQUENCE: 100
gcatcgtaag caaaaatgat                                                    20

<210> SEQ ID NO 101
<211> LENGTH: 20
<212> TYPE: DNA
<213> ORGANISM: Artificial Sequence
<220> FEATURE:
<223> OTHER INFORMATION: Synthetic construct

<400> SEQUENCE: 101
attacagcta tttttaggat                                                    20

<210> SEQ ID NO 102
<211> LENGTH: 20
<212> TYPE: DNA
<213> ORGANISM: Artificial Sequence
<220> FEATURE:
<223> OTHER INFORMATION: Synthetic construct

<400> SEQUENCE: 102
cgggtctcgc tgcgtagcga                                                    20

<210> SEQ ID NO 103
<211> LENGTH: 20
<212> TYPE: DNA
<213> ORGANISM: Artificial Sequence
<220> FEATURE:
<223> OTHER INFORMATION: Synthetic construct

<400> SEQUENCE: 103
gacgcgcgca gcgctgctca                                                    20

<210> SEQ ID NO 104
<211> LENGTH: 20
<212> TYPE: DNA
<213> ORGANISM: Artificial Sequence
<220> FEATURE:
<223> OTHER INFORMATION: Synthetic construct

<400> SEQUENCE: 104
acatacatag ggacgggcgg                                                    20

<210> SEQ ID NO 105
<211> LENGTH: 20
<212> TYPE: DNA
<213> ORGANISM: Artificial Sequence
<220> FEATURE:
<223> OTHER INFORMATION: Synthetic construct

<400> SEQUENCE: 105
gaccgagggg cggccgacag                                                    20

<210> SEQ ID NO 106
<211> LENGTH: 20
<212> TYPE: DNA
<213> ORGANISM: Artificial Sequence
<220> FEATURE:
<223> OTHER INFORMATION: Synthetic construct

<400> SEQUENCE: 106
ctccggaccg gcgcgccgat                                                  20

<210> SEQ ID NO 107
<211> LENGTH: 20
<212> TYPE: DNA
<213> ORGANISM: Artificial Sequence
<220> FEATURE:
<223> OTHER INFORMATION: Synthetic construct

<400> SEQUENCE: 107
gcccgcatct gcattgcggt                                                  20

<210> SEQ ID NO 108
<211> LENGTH: 20
<212> TYPE: DNA
<213> ORGANISM: Artificial Sequence
<220> FEATURE:
<223> OTHER INFORMATION: Synthetic construct

<400> SEQUENCE: 108
ggccacgacg cgatctaagg                                                  20

<210> SEQ ID NO 109
<211> LENGTH: 20
<212> TYPE: DNA
<213> ORGANISM: Artificial Sequence
<220> FEATURE:
<223> OTHER INFORMATION: Synthetic construct

<400> SEQUENCE: 109 tttttgggggg tggcgtacac                                                 20

<210> SEQ ID NO 110
<211> LENGTH: 20
<212> TYPE: DNA
<213> ORGANISM: Artificial Sequence
<220> FEATURE:
<223> OTHER INFORMATION: Synthetic construct

<400> SEQUENCE: 110
ttggctcagt caccgccggc                                                  20

<210> SEQ ID NO 111
<211> LENGTH: 20
<212> TYPE: DNA
<213> ORGANISM: Artificial Sequence
<220> FEATURE:
<223> OTHER INFORMATION: Synthetic construct

<400> SEQUENCE: 111
atttcagcaa ctctcgcccg                                                  20

<210> SEQ ID NO 112
<211> LENGTH: 20
<212> TYPE: DNA
<213> ORGANISM: Artificial Sequence
<220> FEATURE:
<223> OTHER INFORMATION: Synthetic construct

<400> SEQUENCE: 112
cgctccctag cacgtggtgc                                                  20

<210> SEQ ID NO 113

```
<211> LENGTH: 20
<212> TYPE: DNA
<213> ORGANISM: Artificial Sequence
<220> FEATURE:
<223> OTHER INFORMATION: Synthetic construct

<400> SEQUENCE: 113
cattgggaga ttggcagcga                                               20

<210> SEQ ID NO 114
<211> LENGTH: 20
<212> TYPE: DNA
<213> ORGANISM: Artificial Sequence
<220> FEATURE:
<223> OTHER INFORMATION: Synthetic construct

<400> SEQUENCE: 114
gtcagcagca ccagcgtctg                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic construct

<400> SEQUENCE: 115
gcggagcgca gcgaaacggc                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic construct

<400> SEQUENCE: 116
ctaccgcgcc ctcatgcagg                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic construct

<400> SEQUENCE: 117
gggtccggct tgggcaggtg                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic construct

<400> SEQUENCE: 118
aactccggca gaactccgag                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic construct

<400> SEQUENCE: 119
```
gcggtagaaa ggagcagcgg                                              20

<210> SEQ ID NO 120
<211> LENGTH: 20
<212> TYPE: RNA
<213> ORGANISM: Artificial Sequence
<220> FEATURE:
<223> OTHER INFORMATION: Synthetic construct

<400> SEQUENCE: 120
uuaugacuac augauucaug                                              20

<210> SEQ ID NO 121
<211> LENGTH: 20
<212> TYPE: RNA
<213> ORGANISM: Artificial Sequence
<220> FEATURE:
<223> OTHER INFORMATION: Synthetic construct

<400> SEQUENCE: 121
aauuaaauug ugauagcaua                                              20

<210> SEQ ID NO 122
<211> LENGTH: 20
<212> TYPE: RNA
<213> ORGANISM: Artificial Sequence
<220> FEATURE:
<223> OTHER INFORMATION: Synthetic construct

<400> SEQUENCE: 122
uucuccuuuu gaucaucuag                                              20

<210> SEQ ID NO 123
<211> LENGTH: 20
<212> TYPE: RNA
<213> ORGANISM: Artificial Sequence
<220> FEATURE:
<223> OTHER INFORMATION: Synthetic construct

<400> SEQUENCE: 123
auaacacagg uuguguuucc                                              20

<210> SEQ ID NO 124
<211> LENGTH: 20
<212> TYPE: RNA
<213> ORGANISM: Artificial Sequence
<220> FEATURE:
<223> OTHER INFORMATION: Synthetic construct

<400> SEQUENCE: 124
uaaaguaaaa uguucuucuc                                              20

<210> SEQ ID NO 125
<211> LENGTH: 20
<212> TYPE: RNA
<213> ORGANISM: Artificial Sequence
<220> FEATURE:
<223> OTHER INFORMATION: Synthetic construct

<400> SEQUENCE: 125
gaugcacaga gaugcuuuug                                              20

<210> SEQ ID NO 126
<211> LENGTH: 20
<212> TYPE: RNA

```
<213> ORGANISM: Artificial Sequence
<220> FEATURE:
<223> OTHER INFORMATION: Synthetic construct

<400> SEQUENCE: 126
gugccgggaa accuugauug                                                    20

<210> SEQ ID NO 127
<211> LENGTH: 20
<212> TYPE: RNA
<213> ORGANISM: Artificial Sequence
<220> FEATURE:
<223> OTHER INFORMATION: Synthetic construct

<400> SEQUENCE: 127
caaucaaggu uucccggcac                                                    20

<210> SEQ ID NO 128
<211> LENGTH: 20
<212> TYPE: RNA
<213> ORGANISM: Artificial Sequence
<220> FEATURE:
<223> OTHER INFORMATION: Synthetic construct

<400> SEQUENCE: 128
gaaaacuaag uuuauuagag                                                    20

<210> SEQ ID NO 129
<211> LENGTH: 20
<212> TYPE: RNA
<213> ORGANISM: Artificial Sequence
<220> FEATURE:
<223> OTHER INFORMATION: Synthetic construct

<400> SEQUENCE: 129
gcaucguaag caaaaaugau                                                    20

<210> SEQ ID NO 130
<211> LENGTH: 20
<212> TYPE: RNA
<213> ORGANISM: Artificial Sequence
<220> FEATURE:
<223> OTHER INFORMATION: Synthetic construct

<400> SEQUENCE: 130
auuacagcua uuuuuaggau                                                    20

<210> SEQ ID NO 131
<211> LENGTH: 20
<212> TYPE: RNA
<213> ORGANISM: Artificial Sequence
<220> FEATURE:
<223> OTHER INFORMATION: Synthetic construct

<400> SEQUENCE: 131
cgggucucgc ugcguagcga                                                    20

<210> SEQ ID NO 132
<211> LENGTH: 20
<212> TYPE: RNA
<213> ORGANISM: Artificial Sequence
<220> FEATURE:
<223> OTHER INFORMATION: Synthetic construct

<400> SEQUENCE: 132
gacgcgcgca gcgcugcuca                                                    20
```

```
<210> SEQ ID NO 133
<211> LENGTH: 20
<212> TYPE: RNA
<213> ORGANISM: Artificial Sequence
<220> FEATURE:
<223> OTHER INFORMATION: Synthetic construct

<400> SEQUENCE: 133
acauacauag ggacgggcgg                                               20

<210> SEQ ID NO 134
<211> LENGTH: 20
<212> TYPE: RNA
<213> ORGANISM: Artificial Sequence
<220> FEATURE:
<223> OTHER INFORMATION: Synthetic construct

<400> SEQUENCE: 134
gaccgagggg cggccgacag                                               20

<210> SEQ ID NO 135
<211> LENGTH: 20
<212> TYPE: RNA
<213> ORGANISM: Artificial Sequence
<220> FEATURE:
<223> OTHER INFORMATION: Synthetic construct

<400> SEQUENCE: 135
cuccggaccg gcgcgccgau                                               20

<210> SEQ ID NO 136
<211> LENGTH: 20
<212> TYPE: RNA
<213> ORGANISM: Artificial Sequence
<220> FEATURE:
<223> OTHER INFORMATION: Synthetic construct

<400> SEQUENCE: 136
gcccgcaucu gcauugcggu                                               20

<210> SEQ ID NO 137
<211> LENGTH: 20
<212> TYPE: RNA
<213> ORGANISM: Artificial Sequence
<220> FEATURE:
<223> OTHER INFORMATION: Synthetic construct

<400> SEQUENCE: 137
ggccacgacg cgaucuaagg                                               20

<210> SEQ ID NO 138
<211> LENGTH: 20
<212> TYPE: RNA
<213> ORGANISM: Artificial Sequence
<220> FEATURE:
<223> OTHER INFORMATION: Synthetic construct

<400> SEQUENCE: 138
uuuuuggggg uggcguacac                                               20

<210> SEQ ID NO 139
<211> LENGTH: 20
<212> TYPE: RNA
<213> ORGANISM: Artificial Sequence
<220> FEATURE:
```

<223> OTHER INFORMATION: Synthetic construct

<400> SEQUENCE: 139
uuggcucagu caccgccggc                                               20

<210> SEQ ID NO 140
<211> LENGTH: 20
<212> TYPE: RNA
<213> ORGANISM: Artificial Sequence
<220> FEATURE:
<223> OTHER INFORMATION: Synthetic construct

<400> SEQUENCE: 140
auuucagcaa cucucgcccg                                               20

<210> SEQ ID NO 141
<211> LENGTH: 20
<212> TYPE: RNA
<213> ORGANISM: Artificial Sequence
<220> FEATURE:
<223> OTHER INFORMATION: Synthetic construct

<400> SEQUENCE: 141
cgcucccuag cacguggugc                                               20

<210> SEQ ID NO 142
<211> LENGTH: 20
<212> TYPE: RNA
<213> ORGANISM: Artificial Sequence
<220> FEATURE:
<223> OTHER INFORMATION: Synthetic construct

<400> SEQUENCE: 142
cauugggaga uuggcagcga                                               20

<210> SEQ ID NO 143
<211> LENGTH: 20
<212> TYPE: RNA
<213> ORGANISM: Artificial Sequence
<220> FEATURE:
<223> OTHER INFORMATION: Synthetic construct

<400> SEQUENCE: 143
gucagcagca ccagcgucug                                               20

<210> SEQ ID NO 144
<211> LENGTH: 20
<212> TYPE: RNA
<213> ORGANISM: Artificial Sequence
<220> FEATURE:
<223> OTHER INFORMATION: Synthetic construct

<400> SEQUENCE: 144
gcggagcgca gcgaaacggc                                               20

<210> SEQ ID NO 145
<211> LENGTH: 20
<212> TYPE: RNA
<213> ORGANISM: Artificial Sequence
<220> FEATURE:
<223> OTHER INFORMATION: Synthetic construct

<400> SEQUENCE: 145
cuaccgcgcc cucaugcagg                                               20

```
<210> SEQ ID NO 146
<211> LENGTH: 20
<212> TYPE: RNA
<213> ORGANISM: Artificial Sequence
<220> FEATURE:
<223> OTHER INFORMATION: Synthetic construct

<400> SEQUENCE: 146
ggguccggcu ugggcaggug                                                      20

<210> SEQ ID NO 147
<211> LENGTH: 20
<212> TYPE: RNA
<213> ORGANISM: Artificial Sequence
<220> FEATURE:
<223> OTHER INFORMATION: Synthetic construct

<400> SEQUENCE: 147
aacuccggca gaacuccgag                                                      20

<210> SEQ ID NO 148
<211> LENGTH: 20
<212> TYPE: RNA
<213> ORGANISM: Artificial Sequence
<220> FEATURE:
<223> OTHER INFORMATION: Synthetic construct

<400> SEQUENCE: 148
gcgguagaaa ggagcagcgg                                                      20
```